(12) United States Patent
Rieger et al.

(10) Patent No.: US 8,222,228 B2
(45) Date of Patent: Jul. 17, 2012

(54) SUBSTITUTED ARYL PIPERIDINYLALKYNYLADENOSINES AS A2AR AGONISTS

(75) Inventors: Jayson M. Rieger, Charlottesville, VA (US); Robert D. Thompson, Charlottesville, VA (US)

(73) Assignee: Forest Laboratories Holdings Limited, Hamilton (BM)

( * ) Notice: Subject to any disclaimer, the term of this patent is extended or adjusted under 35 U.S.C. 154(b) by 0 days.

(21) Appl. No.: 12/981,308

(22) Filed: Dec. 29, 2010

(65) Prior Publication Data

US 2011/0091385 A1 Apr. 21, 2011

Related U.S. Application Data

(63) Continuation of application No. 12/501,750, filed on Jul. 13, 2009, now Pat. No. 7,888,329, which is a continuation of application No. 11/804,165, filed on May 17, 2007, now Pat. No. 7,589,076.

(60) Provisional application No. 60/747,625, filed on May 18, 2006.

(51) Int. Cl.
*A01N 43/04* (2006.01)
*A61K 31/70* (2006.01)

(52) U.S. Cl. ............ 514/46; 514/47; 514/423
(58) Field of Classification Search ............ None
See application file for complete search history.

(56) References Cited

U.S. PATENT DOCUMENTS

| 7,214,665 | B2 * | 5/2007 | Linden et al. | 514/46 |
| 7,378,400 | B2 * | 5/2008 | Rieger et al. | 514/46 |
| 7,605,143 | B2 * | 10/2009 | Rieger et al. | 514/46 |

* cited by examiner

*Primary Examiner* — Patrick Lewis

(57) ABSTRACT

$A_{2A}$ agonists of formula (I) is provided, wherein $R^1$, $R^2$, $R^4$, $R^5$, X, Y, Z, n, p, and q are as described herein.

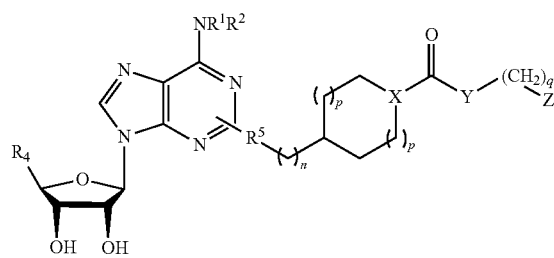

(I)

Also provided are compositions comprising and methods of using compounds of formula (I).

8 Claims, No Drawings

SUBSTITUTED ARYL PIPERIDINYLALKYNYLADENOSINES AS A2AR AGONISTS

RELATED APPLICATIONS

This application is a continuation of U.S. application Ser. No. 12/501,750, filed Jul. 13, 2009, which is a continuation of U.S. application Ser. No. 11/804,165, issued as U.S. Pat. No. 7,589,076 and filed May 17, 2007, which, in turn, claims the benefit of U.S. Provisional Application No. 60/747,625, filed May 18, 2006. Each of these applications is incorporated herein in its entirety by this reference.

BACKGROUND OF THE INVENTION

The inflammatory response serves the purpose of eliminating harmful agents from the body. A wide range of pathogenic insults can initiate an inflammatory response including infection, allergens, autoimmune stimuli, immune response to transplanted tissue, noxious chemicals, and toxins, ischemia/reperfusion, hypoxia, mechanical and thermal trauma. Inflammation normally is a very localized action, which serves in expulsion, attenuation by dilution, and isolation of the damaging agent and injured tissue. The body's response becomes an agent of disease when it results in inappropriate injury to host tissues in the process of eliminating the targeted agent, or responding to a traumatic insult.

The release of inflammatory cytokines such as tumor necrosis factor-alpha (TNFα) by leukocytes is a means by which the immune system combats pathogenic invasions, including infections. TNFα stimulates the expression and activation of adherence factors on leukocytes and endothelial cells, primes neutrophils for an enhanced inflammatory response to secondary stimuli and enhances adherent neutrophil oxidative activity. In addition, macrophages/dendritic cells act as accessory cells processing antigen for presentation to lymphocytes. The lymphocytes, in turn, become stimulated to act as pro-inflammatory cytotoxic cells.

Generally, cytokines stimulate neutrophils to enhance oxidative (e.g., superoxide and secondary products) and non-oxidative (e.g., myeloperoxidase and other enzymes) inflammatory activity. Inappropriate and over-release of cytokines can produce counterproductive exaggerated pathogenic effects through the release of tissue-damaging oxidative and non-oxidative products Although monocytes collect slowly at inflammatory foci, given favorable conditions, the monocytes develop into long-term resident accessory cells and macrophages. Upon stimulation with an inflammation trigger, monocytes/macrophages also produce and secrete an array of cytokines (including TNFα), complement, lipids, reactive oxygen species, proteases and growth factors that remodel tissue and regulate surrounding tissue functions.

For example, inflammatory cytokines have been shown to be pathogenic in: arthritis (C. A. Dinarello, Semin. Immunol., 4, 133 (1992)); ischemia (A. Seekamp et al., Agents-Actions-Supp., 41, 137 (1993)); septic shock (D. N. Mannel et al., Rev. Infect. Dis., 9 (suppl. 5), S602-S606 (1987)); asthma (N. M. Cembrzynska et al., Am. Rev. Respir. Dis., 147, 291 (1993)); organ transplant rejection (D. K. Imagawa et al., Transplantation, 51, 57 (1991); multiple sclerosis (H. P. Hartung, Ann. Neurol., 33, 591 (1993)); AIDS (T. Matsuyama et al., AIDS, 5, 1405 (1991)); and in alkali-burned eyes (F. Miyamoto et al., Opthalmic Res., 30, 168 (1997)). In addition, superoxide formation in leukocytes has been implicated in promoting replication of the human immunodeficiency virus (HW) (S. Legrand-Poels et al., AIDS Res. Hum. Retroviruses, 6, 1389 (1990)).

Sickle Cell Disease has historically been viewed as a disease of red cell abnormalities. Recently, it has been suggested that the wide spectrum of clinical manifestations of this disease result in part from chronic inflammation. This concept is supported by evidence that SCD patients demonstrate many clinical symptoms of chronic inflammation such as increased cytokine levels, the presence of circulating endothelial cells, increased white blood cell counts and an increase in cellular markers of leukocyte and endothelial activation.

It is well known that adenosine and some analogs of adenosine that non-selectively activate adenosine receptor subtypes decrease neutrophil production of inflammatory oxidative products (B. N. Cronstein et al., Ann. N.Y. Acad. Sci., 451, 291 (1985); P. A. Roberts et al., Biochem. J., 227, 669 (1985); D. J. Schrier et al., J. Immunol., 137, 3284 (1986); B. N. Cronstein et al., Clinical Immunol. and Immunopath., 42, 76 (1987); M. A. Iannone et al., in Topics and Perspective in Adenosine Research, E. Gerlach et al., eds., Springer-Verlag, Berlin, p. 286 (1987); S. T. McGarrity et al., J. Leukocyte Biol., 44, 411421 (1988); J. De La Harpe et al., J. Immunol., 143, 596 (1989); S. T. McGarrity et al., J. Immunol., 142, 1986 (1989); and C. P. Nielson et al., Br. J. Pharmacol., 97, 882 (1989)).

For example, adenosine has been shown to inhibit superoxide release from neutrophils stimulated by chemoattractants such as the synthetic mimic of bacterial peptides, f-met-leu-phe (fMLP), and the complement component $C_{5a}$ (B. N. Cronstein et al., J. Immunol., 135, 1366 (1985)). Adenosine can decrease the greatly enhanced oxidative burst of PMN (neutrophil) first primed with TNFα and then stimulated by a second stimulus such as f-met-leu-phe (G. W. Sullivan et al., Clin. Res., 41, 172A (1993)). Additionally, it has been reported that adenosine can decrease the rate of HIV replication in a T-cell line (S. Sipka et al., Acta. Biochim. Biopys. Hung., 23, 75 (1988)). However, there is no evidence that in vivo adenosine has anti-inflammatory activity (G. S. Firestein et al., Clin. Res., 41, 170A (1993); and B. N. Cronstein et al., Clin. Res., 41, 244A (1993)).

It has been suggested that there is more than one subtype of adenosine receptor on neutrophils that can have opposite effects on superoxide release (B. N. Cronstein et al., J. Clin. Invest., 85, 1150 (1990)). The existence of $A_{2A}$ receptor on neutrophils was originally demonstrated by Van Calker et al. (D. Van Calker et al., Eur. J. Pharmacology, 206, 285 (1991)).

There has been progressive development of compounds that are more and more potent and/or selective as agonists of $A_{2A}$ adenosine receptors (AR) based on radioligand binding assays and physiological responses. Initially, compounds with little or no selectivity for $A_{2A}$ receptors were developed, such as adenosine itself or 5'-carboxamides of adenosine, such as 5'-N-ethylcarboxamidoadenosine (NECA) (B. N. Cronstein et al., J. Immunol., 135, 1366 (1985)). Later, it was shown that addition of 2-alkylamino substituents increased potency and selectivity, e.g., CV1808 and CGS21680 (M. F. Jarvis et al., J. Pharmacol. Exp. Ther., 251, 888 (1989)). 2-Alkoxy-substituted adenosine derivatives such as WRC-0090 are even more potent and selective as agonists at the coronary artery $A_{2A}$ receptor (M. Ueeda et al., J. Med. Chem., 34, 1334 (1991)). The 2-alkylhydrazino adenosine derivatives, e.g., SHA 211 (also called WRC-0474) have also been evaluated as agonists at the coronary artery $A_{2A}$ receptor (K. Niiya et al., J. Med. Chem., 35, 4557 (1992)).

There is one report of the combination of relatively non-specific adenosine analogs, R-phenylisopropyladenosine (R-PIA) and 2-chloroadenosine (Cl-Ado) with a phosphodiesterase (PDE) inhibitor resulting in a lowering of neutrophil oxidative activity (M. A. Iannone et al., Topics and Perspectives in Adenosine Research, E. Garlach et al., eds., Springer-Verlag, Berlin, pp. 286-298 (1987)). However, R-PIA and Cl-Ado analogs are actually more potent activators of $A_1$ adenosine receptors than of $A_{2A}$ adenosine receptors and, thus, are likely to cause side effects due to activation of $A_1$ receptors on cardiac muscle and other tissues causing effects such as "heart block."

R. A. Olsson et al. (U.S. Pat. No. 5,278,150) disclose selective adenosine $A_2$ receptor agonists of the formula: wherein Rib is ribosyl, $R^1$ can be H and $R_2$ can be cycloalkyl. The compounds are disclosed to be useful for treating hypertension, atherosclerosis and as vasodilators.

Olsson et al. (U.S. Pat. No. 5,140,015) disclose certain adenosine $A_2$ receptor agonists of formula: wherein $C(X)BR_2$ can be $CH_2OH$ and $R^1$ can be alkyl- or alkoxyalkyl. The compounds are disclosed to be useful as vasodilators or an antihypertensives.

Linden et al. (U.S. Pat. No. 5,877,180) is based on the discovery that certain inflammatory diseases, such as arthritis and asthma, may be effectively treated by the administration of compounds which are selective agonists of $A_{2A}$ adenosine receptors, preferably in combination with a Type IV phosphodiesterase inhibitor. An embodiment of the Linden et al. invention provides a method for treating inflammatory diseases by administering an effective amount of an $A_{2A}$ adenosine receptor of the following formula: wherein R and X are as described in the patent.

In one embodiment, the Linden et al. invention involves the administration of a Type IV phosphodiesterase (PDE) inhibitor in combination with the $A_{2A}$ adenosine receptor agonist. The Type IV phosphodiesterase (PDE) inhibitor includes racemic and optically active 4-(polyalkoxyphenyl)-2-pyrrolidones of the following formula: wherein R', $R^{18}$, $R^{19}$ and X are as disclosed and described in U.S. Pat. No. 4,193,926. Rolipram is an example of a suitable Type IV PDE inhibitor included within the above formula.

G. Cristalli (U.S. Pat. No. 5,593,975) discloses 2-arylethynyl, 2-cycloalkylethynyl or 2-hydroxyalkylethynyl derivatives, wherein the riboside residue is substituted by carboxy amino, or substituted carboxy amino ($R_3HNC(O)$—). 2-Alkynylpurine derivatives have been disclosed in Miyasaka et al. (U.S. Pat. No. 4,956,345), wherein the 2-alkynyl group is substituted with ($C_3$-$C_{16}$) alkyl. The '975 compounds are disclosed to be vasodilators and to inhibit platelet aggregation, and thus to be useful as anti-ischemic, anti-atherosclerosis and anti-hypertensive agents.

However, a continuing need exists for selective $A_2$ adenosine receptor agonists useful for therapeutic applications, which have reduced side effects. In addition, a continuing need exists for selective A2 adenosine receptor agonists useful for use as pharmacological stressors in stress imaging or in other ventricular function imaging techniques, which preferably have reduced side effects, while being chemically stable and short-acting.

There also is a need for new therapies for treating disorders caused by Sickle Cell Disease. Current therapies are marginally effective and have undesirable side effects. Accordingly, there is a need for compounds and methods for treating and preventing a sickle cell crisis.

SUMMARY OF THE INVENTION

The present invention provides novel compounds and pharmaceutical compositions that act as adenosine $A_{2A}$ receptor agonists.

The present invention also provides novel pharmaceutical compositions, comprising a new compound and a pharmaceutically acceptable carrier.

The present invention provides novel methods of treatment and diagnosis using these new compounds and compositions.

In accomplishing these objects, there has been provided, in accordance with one aspect of the present invention, a compound of formula (I)

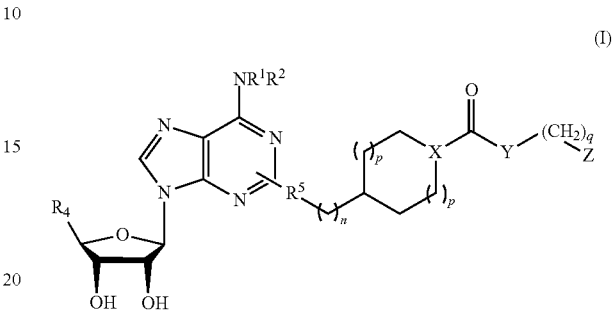

(I)

wherein the variables are defined below.

DETAILED DESCRIPTION OF THE INVENTION

The present invention provides novel compounds that act as agonists at the adenosine $A_{2A}$ receptor, and methods for using the compounds in methods of treating diseases and conditions in which the $A_{2A}$ receptor is implicated and for which agonism of the receptor provides therapeutic benefit. The compounds may be used, for example, for the treatment of inflammatory activity in mammalian tissue, or for the treatment of sickle cell disease. The inflammatory tissue activity can be due to pathological agents or can be due to physical, chemical or thermal trauma, or the trauma of medical procedures, such as organ, tissue or cell transplantation, angioplasty (PCTA), inflammation following ischemia/reperfusion, or grafting. The compounds of the inventions also may be used in conjunction with other anti-inflammatory treatments or in conjunction with anti-pathogenic agents.

In an embodiment, the present invention provides novel compounds of formula I or a stereoisomer or pharmaceutically acceptable salt thereof:

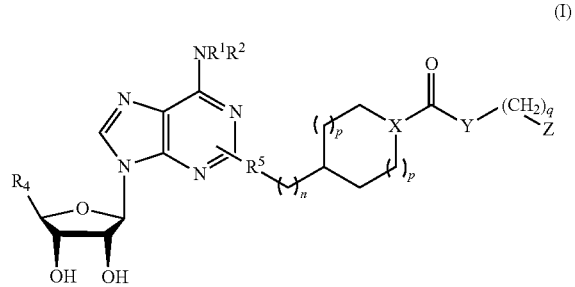

(I)

wherein:
$R^1$ and $R^2$ independently are selected from the group consisting of H, ($C_1$-$C_8$)alkyl, ($C_3$-$C_8$)cycloalkyl, ($C_3$-$C_8$)cycloalkyl($C_1$-$C_8$)alkylene, aryl, aryl($C_1$-$C_8$)alkylene, heteroaryl, heteroaryl($C_1$-$C_8$)alkylene-, diaryl($C_1$-$C_8$)alkylene, and diheteroaryl($C_1$-$C_8$)alkylene, wherein the aryl and heteroaryl rings are optionally substituted with 1-4 groups inde3pendently selected from fluoro, chloro, iodo, bromo, methyl, trifluoromethyl, and methoxy;

each R independently is selected from the group consisting of H, $C_1$-$C_4$ alkyl, cyclopropyl, cyclobutyl, and $(CH_2)_a$cyclopropyl;

X is CH or N, provided that when X is CH then Z cannot be substituted with halogen, $C_1$-$C_6$ alkyl, hydroxyl, amino, or mono- or di-($C_1$-$C_6$-alkyl)amino;

Y is selected from the group consisting of O, $NR^1$, —$(OCH_2CH_2O)_mCH_2$—, and —$(NR^1CH_2CH_2O)_mCH_2$—, provided that when Y is O or $NR^1$, then at least one substituent is present on Z;

Z is selected from the group consisting of 5-membered heteroaryl, 6-membered aryl, 6-membered heteroaryl, carbocyclic biaryl, and heterocyclic biaryl, wherein the point of attachment of Y to Z is a carbon atom on Z, wherein Z is substituted with 0-4 groups independently selected from the group consisting of F, Cl, Br, I, ($C_1$-$C_4$)alkyl, —$(CH_2)_aOR^3$, —$(CH_2)_aNR^3R^3$, —NHOH, —$NR^3NR^3R^3$, nitro, —$(CH_2)_a CO_2R^3$, —$(CH_2)_aCONR^3R^3$, trifluoromethyl, and trifluoromethoxy;

alternatively, Y and Z together form an indolyl, indolinyl, isoindolinyl, tetrahydroisoquinolinyl, or tetrahydroquinolinyl moiety wherein the point of attachment is via the ring nitrogen and wherein said indolyl, indolinyl, isoindolinyl, tetrahydroisoquinolinyl, or tetrahydroquinolinyl moiety, which is substituted with 0-4 groups independently selected from the group consisting of F, Cl, Br, I, $C_1$-$C_4$ alkyl, —$(CH_2)_aOR^3$, —$(CH_2)_aNR^3R^3$, —NHOH, —$NR^3NR^3R^3$, $NO_2$, —$(CH_2)_aCN$, —$(CH_2)_aCO_2R^3$, —$(CH_2)_aCONR^3R^3$, $CF_3$, and $OCF_3$;

$R^3$ is independently selected from the group consisting of H, ($C_1$-$C_6$)alkyl, cycloalkyl, aryl, and heteroaryl;

$R^4$ is selected from the group consisting of $CH_2OR$, C(O)NRR, and $CO_2R$;

$R^5$ is selected from the group consisting of $CH_2CH_2$, CH=CH, and C≡C a is selected from 0, 1, and 2;

m is selected from 1, 2, and 3;

n is selected from 0, 1, and 2;

each p independently is selected from 0, 1, and 2; and, q is selected from 0, 1, and 2.

In another embodiment, the present invention provides novel compounds of formula (Ia) or a pharmaceutically acceptable salt thereof:

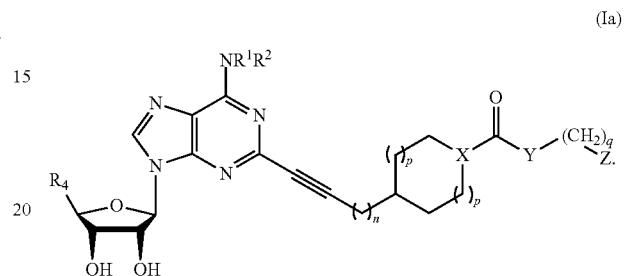

(Ia)

In another embodiment, the present invention provides novel compounds of formula (Ib) or a pharmaceutically acceptable salt thereof:

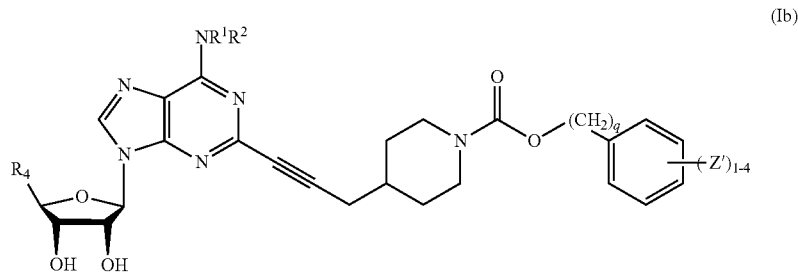

(Ib)

wherein:
each Z' is independently selected from the group consisting F, Cl, Br, I, $C_1$-$C_4$ alkyl, —$(CH_2)_aOR^3$, —$(CH_2)_aNR^3R^3$, —NHOH, —$NR^3NR^3R^3$, $NO_2$, —$(CH_2)_aCN$, —$(CH_2)_a CO_2R^3$, —$(CH_2)_aCONR^3R^3$, $CF_3$, and $OCF_3$.

In another embodiment, the present invention provides novel compounds, wherein R is selected from H, methyl, ethyl or cyclopropyl.

In another embodiment, the present invention provides novel compounds of formula (Ic) or a pharmaceutically acceptable salt thereof:

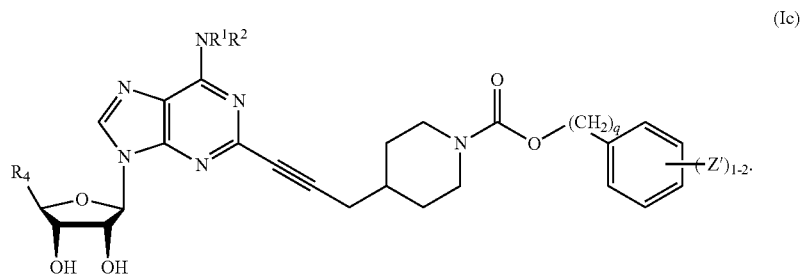

(Ic)

In another embodiment, the present invention provides novel compounds wherein Z' is selected from the group consisting of F, Cl, methyl, $OR^3$, $NO_2$, CN, $NR^3R^3$ and $CO_2R^3$.

In another embodiment, the present invention provides novel compounds wherein $R^3$ is methyl or hydrogen.

In another embodiment, the present invention provides novel compounds wherein the compound is selected from the group consisting of Compound Numbers 3, 5-31, and 33-57 shown in Table 1 (below).

The invention provides a compound of formula I for use in medical therapy, preferably for use in treating inflammation or protecting mammalian tissue from inflammation such as an inflammatory response, e.g., resulting from allergy, trauma or ischemia/reperfusion injury, as well as the use of a compound of formula I for the manufacture of a medicament for the treatment of an inflammatory response due to a pathological condition or symptom in a mammal which is associated with inflammation.

Mammal or subject includes human, equine, porcine, canine, and feline.

The invention also includes the use of a combination of these compounds with at least one anti-inflammatory compound. An example of such a compound is a type IV phosphodiesterase inhibitor, and the combination can be used to cause synergistic decreases in the inflammatory response mediated by leukocytes.

The invention also provides a pharmaceutical composition comprising an effective amount of the compound of Formula (I), or a pharmaceutically acceptable salt thereof, in combination with a pharmaceutically acceptable diluent or carrier, and optionally, in combination with an anti-inflammatory compound. Preferably, the composition is presented as a unit dosage form. The carrier may be a liquid carrier. The composition may be adapted for oral, intravenous, ocular, parenteral, aerosol or transdermal administration.

The compositions of the present invention may further include a Type IV phosphodiesterase inhibitor, or another anti-inflammatory compound (e.g., other than a PDE inhibitor). The Type IV phosphodiesterase inhibitor may be, for example, rolipram, cilomilast, or roflumilast.

Additionally, the invention provides a therapeutic method for treating a pathological condition or symptom in a mammal where the activity of $A_{2A}$ adenosine receptors is implicated and agonism of said receptors is desired, comprising administering to a mammal in need of such therapy, an effective amount of a compound of formula I, or a pharmaceutically acceptable salt thereof. It is believed that activation of $A_{2A}$ adenosine receptors inhibits inflammation by affecting neutrophils, mast cells, monocytes/macrophages, platelets T-cells and/or eosinophils. Inhibition of these inflammatory cells results in tissue protection following tissue insults.

In addition, the present invention provides a therapeutic method for treating biological diseases that includes the administration of an effective amount of a suitable antibiotic agent, antifungal agent or antiviral agent in conjunction with an $A_{2A}$ adenosine receptor agonist. If no anti-pathogenic agent is known the $A_{2A}$ agonist can be used alone to reduce inflammation, as may occur during infection with antibiotic resistant bacteria, or certain viruses such as those that cause SARS or Ebola. Optionally, the method includes administration of a type IV PDE inhibitor. The $A_{2A}$ adenosine receptor agonist can provide adjunctive therapy for treatment conditions such as, the inflammation, caused by sepsis, for example, human uremic syndrome when administered with antibiotics in the treatment of bio-terrorism weapons, such as anthrax, tularemia, *Escherichia coli*, plague and the like. The present invention also provides adjunctive therapy for treatment of lethal bacterial, fungal and viral infections such as anthrax, tularemia, *escherichia* and plague comprising administration of an antibacterial agent, an antifungal agent or an antiviral agent in conjunction with selective, $A_{2A}$ adenosine receptor agonists.

The present invention provides a therapeutic method for treating biological diseases that provoke inflammation either alone or in combination with a disease killing medicine. These include bacteria in combination with antibiotics, including but not limited to bacteria that cause anthrax, tularemia, plague, lyme disease and anthrax. Also included are viruses including but not limited to those that cause RSV, severe acute respiratory syndrome (SARS), influenza and Ebola with or without anti-viral therapy. Also included are yeast and fungal infections with or without anti-yeast or anti-fungal agents.

The antibacterial agent, antifungal agent or antiviral agent can be co-administered (e.g., simultaneously) with the $A_{2A}$ adenosine receptor agonist or they can be can be administered either simultaneously or as a mixture or they can be administered subsequently. The subsequent administration of the $A_{2A}$ adenosine receptor agonists can be prior to the agent, within minutes or up to about 48 hours after the administration of the agent. Preferably the administration of the $A_{2A}$ adenosine receptor agonists will be within about 24 hours and more preferably within about 12 hours.

The method of the invention will also be useful for treating patients with sepsis, severe sepsis, and potentially, the systemic inflammatory response syndrome, in addition to septic shock. The $A_{2A}$ adenosine receptor agonists exert multiple anti-inflammatory effects early in the inflammatory cascade, and thus a short course of such agonists can produce profound benefit in serious, life-threatening infectious and inflammatory disorders of humans, including inhalational anthrax, tularemia, *escherichia* and plague.

The anti-inflammatory effect of $A_{2A}$ receptor agonists has been documented in vivo, in experimental models of meningitis, peritonitis and arthritis. The potentially fatal syndrome of bacterial sepsis is an increasingly common problem in acute care units. Sepsis and septic shock, now the eleventh leading cause of death in the United States, are increasing in frequency. Current estimates indicate that about 900,000 new cases of sepsis (approximately 60% Gram negative) occur in the United States annually with an estimated crude mortality rate of 35%. Furthermore, the mortality rate, as assessed in recent clinical trials, is approximately 25%, while approximately 10% of patients die from their underlying disease. Shock develops in approximately 200,000 cases annually with an attributable mortality rate of 46% (92,000 deaths). Sepsis accounts for an estimated $5-10 billion annually in health care expenditures. It is now widely appreciated that among hospitalized patients in non-coronary intensive care units, sepsis is the most common cause of death. Sepsis syndrome is a public health problem of major importance. $A_{2A}AR$ agonists are anticipated to have use as a new and unique adjunctive therapeutic approach to reduce morbidity and mortality. It is believed that this treatment will improve the outcome in systemic anthrax, tularemia, *escherichia* and plague.

The agonists of $A_{2A}$ adenosine receptors of the invention can inhibit neutrophil, macrophage and T cell activation and thereby reduce inflammation caused by bacterial and viral infections. The compounds, in conjunction with antibiotics or antiviral agents can prevent or reduce mortality caused by sepsis or hemolytic uremic syndrome or other inflammatory conditions. The effects of adenosine $A_{2A}$ agonists are enhanced by type IV phosphodiesterase inhibitors such as rolipram.

The invention also provides a compound of formula I for use in medical therapy (e.g., for use as an adjunct in the treatment of potentially lethal bacterial infections, such as, anthrax, tularemia, *Escherichia*, plague, or other bacterial or viral infections, and treatment of systemic intoxification caused by bacterial and/or viral infections, as well as the use of a compound of formula I for the manufacture of a medicament for reducing inflammation caused by the bacteria or virus or the treatment thereof in a mammal, such as a human. The compounds of the invention are also useful for treatment of treating systemic intoxification wherein the bacterial or viral agents cause inflammation either directly or as a result of treatment, e.g., with an antibiotic or antiviral agent.

Sepsis is a severe illness caused by overwhelming infection of the bloodstream by toxin-producing bacteria or viruses. The infection, which can manifest as inflammation, can be caused by the bacteria or virus pathogens directly or from the treatment thereof, i.e., the death of the pathogens due to treatment with antibacterial or antiviral agents. Sepsis also can be viewed as the body's response to an infection. The infection can be caused by microorganisms or "germs" (usually bacteria) invade the body, can be limited to a particular body region (e.g., a tooth abscess) or can be widespread in the bloodstream (often referred to as "septicemia" or "blood poisoning")

The systemic intoxification or inflammatory shock is often referred to as Septic shock; Bacteremic shock; Endotoxic shock; Septicemic shock; or Warm shock.

Septic shock is a serious, abnormal condition that occurs when an overwhelming infection leads to low blood pressure and low blood flow. Vital organs, such as the brain, heart, kidneys, and liver may not function properly or may fail. Septic shock occurs most often in the very old and the very young. It also occurs in people with underlying illnesses. Any bacterial organism can cause septic shock. Fungi and viruses may also cause this condition. Toxins released by the bacteria, fungi or viruses may cause direct tissue damage, and may lead to low blood pressure and/or poor organ function. These toxins can also produce a vigorous inflammatory response from the body, which contributes to septic shock.

In another aspect, the present invention also provides a method to treat severe acute respiratory syndrome (SARS), comprising administering to a mammal in need of said therapy, an effective anti-inflammatory amount of an agonists of $A_{2A}$ adenosine receptor, optionally with a PDE-IV inhibitor, such as, rolipram.

The invention also provides methods of treating sickle cell disease by administering the $A_{2A}$ agonists described herein to a subject suffering from sickle cell disease.

The present invention provides compounds and methods of their use for detecting the presence of, and assessing the severity of, coronary artery stenoses in a mammal, such as a human or domestic animal. Preferably, the compounds of the invention are used as pharmacological stress-inducing agents or stressors that are useful in pharmacological stress imaging for the detection and assessment of coronary artery disease. The specific compounds of the invention useful as stress-inducing agents are potent and selective at $A_{2A}$ adenosine receptors, but are also short-acting, so that they are rapidly cleared by the body following the imaging process.

Thus, the present invention provides a method for detecting the presence and severity of coronary artery stenoses in a mammal, such as a human subject, comprising (1) administering an amount of one or more compounds of the general formula (I) and (2) performing a technique on said mammal to detect and/or determine the severity of said coronary artery stenoses.

The invention provides a compound of formula (I) for use in medical diagnostic procedures, preferably for use in detecting the presence of, and assessing the severity of, coronary artery stenoses in a human subject. The present invention provides the use of a compound of formula (I) for the manufacture of a pharmacologic vasodilator agent which could be used with clinical perfusion imaging techniques for diagnosing and assessing the extent of coronary artery disease. Preferred perfusion imaging techniques are planar or single photon emission computed tomography (SPECT) gamma camera scintigraphy, positron emission tomography (PET), nuclear magnetic resonance (NMR) imaging, magnetic resonance imaging (MRI) imaging, perfusion contrast echocardiography, digital subtraction angiography (DSA) and ultrafast X-ray computed tomography (CINE CT).

The invention also provides a pharmaceutical composition comprising an effective amount of the compound of formula (I), or a pharmaceutically acceptable salt thereof, in combination with a pharmaceutically acceptable diluent or carrier. Preferably, the composition is presented as a unit dosage form, and can be adapted for parenteral, e.g., intravenous infusion.

The following definitions are used, unless otherwise described.

Halo is fluoro, chloro, bromo, or iodo.

Alkyl, alkoxy, aralkyl, alkylaryl, etc. denote both straight and branched alkyl groups; but reference to an individual radical such as "propyl" embraces only the straight chain radical, a branched chain isomer such as "isopropyl" being specifically referred to.

Aryl denotes a phenyl radical or an ortho-fused bicyclic carbocyclic radical having about nine to ten ring atoms in which at least one ring is aromatic. Heteroaryl denotes a radical of a monocyclic aromatic ring containing five or six ring atoms consisting of carbon and 1, 2, 3, or 4 heteroatoms each selected from the group consisting of non-peroxide oxygen, sulfur, and N(Y) wherein Y is absent or is H, O, ($C_1$-$C_8$) alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

Heteroaryl encompasses a monocyclic aromatic ring having five or six ring atoms consisting of carbon and 1-4 heteroatoms each selected from the group consisting of non-peroxide oxygen, sulfur, and N(X) wherein X is absent, is H, O, ($C_1$-$C_4$)alkyl, phenyl or benzyl, or is a substituent defined elsewhere. Heteroaryl also encompasses a radical of an ortho-fused bicyclic heterocycle of 8-10 ring atoms, particularly a benz-derivative or one derived by fusing a propylene, trimethylene, or tetramethylene diradical thereto. Only one ring of the bicyclic heteroaryl need be aromatic.

The term "heterocycle" generally represents a non aromatic heterocyclic group, having from 3 to about 10 ring atoms, which can be saturated or partially unsaturated, containing at least one heteroatom (e.g., 1, 2, or 3) selected from the group consisting of oxygen, nitrogen, and sulfur. Specific, "heterocycle" groups include monocyclic, bicyclic, or tricyclic groups containing one or more heteroatoms selected from the group consisting of oxygen, nitrogen, and sulfur. A "heterocycle" group also can include one or more oxo groups (=O) attached to a ring atom. Non-limiting examples of heterocycle groups include 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuelidine, thiomorpholine, and the like.

The term carbocyclic biaryl refers to ortho-fused bicyclic moieties, typically containing 10 carbon atoms. An example is naphthalene. The term heterocyclic biaryl as used herein refers to ortho-fused bicyclic moieties containing 1-4 heteroatoms. Examples include indoles, isoindoles, quinolines, isoquinolines, benzofurans, isobenzofurans, benzothiophenes, benzo[c]thiophenes, benzimidazoles, purines, indazoles, benzoxazole, benzisoxazole, benzothiazole, quinoxalines, quinazolines, cinnolines, and the like.

The point of attachment of either the carbocyclic or heterocyclic biaryl can be to any ring atom permitted by the valency of that atom.

Specific and preferred values listed below for radicals, substituents, and ranges, are for illustration only; they do not exclude other defined values or other values within defined ranges for the radicals and substituents.

Carbon chains and their optionally substituted counterparts can be in any branched chain form permitted by the valencies and steric requirements of the atoms. Specifically, $(C_1-C_8)$alkyl can be methyl, ethyl, propyl, isopropyl, butyl, iso-butyl, sec-butyl, tert-butyl, pentyl, 3-pentyl, neopentyl, hexyl, heptyl, octyl, and the like, in any branched chain form.

As used herein, the term "cycloalkyl" encompasses bicycloalkyl (norbornyl, 2.2.2-bicyclooctyl, etc.) and tricycloalkyl (adamantyl, etc.), optionally comprising 1-2 N, O or S. Cycloalkyl also encompasses (cycloalkyl)alkyl. Thus, $(C_3-C_6)$cycloalkyl can be cyclopropyl, cyclobutyl, cyclopentyl, cyclohexyl and the like. $(C_1-C_8)$alkoxy can be methoxy, ethoxy, propoxy, isopropoxy, butoxy, iso-butoxy, sec-butoxy, pentoxy, 3-pentoxy, or hexyloxy, in any branched chain form.

$(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl.

$(C_1-C_6)$alkanoyl can be acetyl, propanoyl or butanoyl; halo $(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl.

$(C_1-C_6)$alkoxycarbonyl $(CO_2R^2)$ can be methoxycarbonyl, ethoxycarbonyl, propoxycarbonyl, isopropoxycarbonyl, butoxycarbonyl, pentoxycarbonyl, or hexyloxycarbonyl.

$(C_1-C_6)$alkylthio can be methylthio, ethylthio, propylthio, isopropylthio, butylthio, isobutylthio, pentylthio, or hexylthio.

$(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, puridyl (or its N-oxide), thienyl, pyrimidinyl (or its N-oxide), indolyl, isoquinolyl (or its N-oxide) or quinolyl (or its N-oxide).

The term "alkylene" refers to a divalent straight or branched hydrocarbon chain (e.g. ethylene —$CH_2CH_2$—).

The term "aryl$(C_1-C_8)$alkylene" for example includes benzyl, phenethyl, 3-phenylpropyl, naphthylmethyl and the like.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

As used herein the term "in conjunction with" refers to co-administration of an anti-rejection agent with the $A_{2A}$ adenosine receptor agonist. The co-administration of an agent and an $A_{2A}$ adenosine receptor agonists includes administration of the agent and agonist either simultaneously, as a mixture, or sequentially. The sequential administration of the $A_{2A}$ adenosine receptor agonists can be prior to administration of the agent, within minutes or up to about 48 hours either before the administration of the agent. The $A_{2A}$ adenosine receptor agonists can also be administered after the agent. Preferably the administration of the $A_{2A}$ adenosine receptor agonists will be within about 24 hours and more preferably within about 12 hours.

The carbon atom content of various hydrocarbon-containing moieties is indicated by a prefix designating the minimum and maximum number of carbon atoms in the moiety, i.e., the prefix $C_i-C_j$ indicates a moiety of the integer "i" to the integer "j" carbon atoms, inclusive. Thus, for example, $(C_1-C_8)$alkyl refers to alkyl of one to eight carbon atoms, inclusive.

The compounds of the present invention are generally named according to the IUPAC or CAS nomenclature system. Abbreviations which are well known to one of ordinary skill in the art may be used (e.g., "Ph" for phenyl, "Me" for methyl, "Et" for ethyl, "h" for hour or hours and "rt" for room temperature).

It will be appreciated by those skilled in the art that the compounds of formula (I) have more than one chiral center and may be isolated in optically active and racemic forms. Preferably, the riboside moiety of formula (I) is derived from D-ribose. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, or enzymatic techniques, by synthesis from optically-active starting materials, by chiral synthesis, or by chromatographic separation using a chiral stationary phase) and how to determine adenosine agonist activity using the tests described herein, or using other similar tests which are well known in the art.

Among the inflammatory responses that can be treated (including treated prophylactically) with a compound of formula I, optionally with a Type IV PDE inhibitor, are inflammation due to: (a) autoimmune stimulation (autoimmune diseases), such as lupus erythematosus, multiple sclerosis, infertility from endometriosis, type I diabetes mellitus including the destruction of pancreatic islets leading to diabetes and the inflammatory consequences of diabetes, including leg ulcers, Crohn's disease, ulcerative colitis, inflammatory bowel disease, osteoporosis and rheumatoid arthritis; (b) allergic diseases such as asthma, hay fever, rhinitis, poison ivy, vernal conjunctivitis and other eosinophil-mediated conditions; (c) skin diseases such as psoriasis, contact dermatitis, eczema, infectious skin ulcers, healing of open wounds, cellulitis; (d) infectious diseases including sepsis, septic shock, encephalitis, infectious arthritis, endotoxic shock, gram negative shock, Jarisch-Herxheimer reaction, anthrax, plague, tularemia, ebola, shingles, toxic shock, cerebral malaria, bacterial meningitis, acute respiratory distress syndrome (ARDS), chronic obstructive pulmonary disease (COPD), lyme disease, HIV infection, (TNFα-enhanced HIV replication, TNFα inhibition of reverse transcriptase inhibitor activity); (e) wasting diseases: cachexia secondary to cancer and HIV; (f) organ, tissue or cell transplantation (e.g., bone marrow, cornea, kidney, lung, liver, heart, skin, pancreatic islets) including transplant rejection, and graft versus host disease; (g) adverse effects from drug therapy, including adverse effects from amphotericin B treatment, adverse effects from immunosuppressive therapy, e.g., interleukin-2 treatment, adverse effects from OKT3 treatment, contrast dyes, antibiotics, adverse effects from GM-CSF treatment, adverse effects of cyclosporine treatment, and adverse effects of aminoglycoside treatment, stomatitis and mucositis due to immunosuppression; (h) cardiovascular conditions including circulatory diseases induced or exasperated by an inflammatory response, such as ischemia, atherosclerosis, peripheral vascular disease, restenosis following angioplasty, inflammatory aortic aneurysm, vasculitis, stroke, spinal cord injury, congestive heart failure, hemorrhagic shock, ischemia/reperfusion injury, vasospasm following subarachnoid hemorrhage, vasospasm following cerebrovascular accident, pleuritis, pericarditis, and the cardiovascular complications of diabetes; (i) dialysis, including pericarditis, due to peritoneal dialysis; (j) gout; and (k) chemical or thermal trauma due to burns, acid, alkali and the like.

Additional diseases include equine disorders such as laminitis and founder's disease.

Of particular interest and efficacy is the use of the present compounds to limit inflammatory responses where the ischemia/reperfusion injury is caused by angioplasty or throbolysis. Also of particular interest and efficacy is the use of the present compounds to limit inflammatory responses due to organ, tissue or cell transplantation, i.e., the transplantation of allogeneic or xenogeneic tissue into a mammalian recipient, autoimmune diseases and inflammatory conditions due to circulatory pathologies and the treatment thereof, including angioplasty, stent placement, shunt placement or grafting. Unexpectedly, it is found that administration of one or more compounds of formula (I) is effective after the onset of the inflammatory response, e.g., after the subject is afflicted with a pathology or trauma that initiates an inflammatory response.

Tissue or cells comprising ligand bound receptor sites can be used to measure the selectively of test compounds for specific receptor subtypes, the amount of bioactive compound in blood or other physiological fluids, or can be used as a tool to identify potential therapeutic agents for the treatment of diseases or conditions associated with receptor site activation, by contacting said agents with said ligand-receptor complexes, and measuring the extent of displacement of the ligand and/or binding of the agent, or the cellular response to said agent (e.g., cAMP accumulation).

The following abbreviations have been used herein:

| | |
|---|---|
| 2-Aas | 2-alkynyladenosines; |
| $^{125}$I-ABA | $N^6$-(4-amino-3-$^{125}$iodo-benzyl)adenosine |
| APCI | Atmospheric pressure chemical ionization |
| CCPA | 2-chloro-$N^6$-cyclopentyladenosine; |
| Cl-IB-MECA | $N^6$-3-iodo-2-chlorobenzyladenosine-5'-N-methyluronamide; |
| CPA | $N^6$-cyclopentyladenosine |
| DMF | dimethylformamide |
| DMSO | dimethylsulfoxide |
| DMSO-$d_6$ | deuterated dimethylsulfoxide |
| EtOAc | ethyl acetate |
| eq | equivalent |
| GPCR | G protein coupled receptor; hA$_{2A}$AR, Recombinant human A$_{2A}$ adenosine receptor; |
| IADO | 2-Iodoadenosine |
| $^{125}$I-APE, | 2[2-(4-amino-3-[$^{125}$I]iodophenyl)ethyl-amino]adenosine; |
| NECA | 5'-N-ethylcarboxamidoadenosine; |
| IB-MECA | $N^6$-3-iodobenzyladenosine-5'-N-methyluronamide; |
| 2-Iodoadenosine | 5-(6-amino-2-iodo-purin-9-yl)-3,4-dihydroxytetra-hydro-furan-2carboxylic acid ethylamide |
| HPLC | high-performance liquid chromatography |
| HRMS | high-resolution mass spectrometry |
| $^{125}$I-ZM241385, | $^{125}$I-4-(2-[7-amino-2-[2-furyl][1,2,4]triazolo[2,3-α][1,3,5]-triazin-5-yl-amino]ethyl)phenol; |
| INECA | 2-iodo-N-ethylcarboxamidoadenosine |
| LC/MS | liquid chromatography/mass spectrometry |
| m.p. | melting point |
| MHz | megahertz |
| MRS 1220, | N-(9-chloro-2-furan-2-yl-[1,2,4]triazolo[1,5-c]quinazolin-5-yl)-2-phenylacetamide; |
| MS | mass spectrometry |
| NECA | N-ethylcarboxamidoadenosine |
| NMR | nuclear magnetic resonance |
| RP-HPLC | reverse phase high-performance liquid chromatography |
| TBAF | tetrabutylammonium fluoride |
| TBS | tert-butyldimethylsilyl |
| TBDMSCl | tert-butyldimethylsilylchloride |
| TEA | triethylamine |
| TFA | trifluoroacetic acid |
| THF | tetrahydrofuan |
| TLC | thin layer chromatography |
| p-TSOH | para-toluenesulfonic acid |
| XAC | 8-(4-((2-aminoethyl)aminocarbonyl-methyloxy)-phenyl)-1-3-dipropylxanthine. |

Specific Type IV phosphodiesterase (PDE) inhibitors useful in practicing the instant invention include racemic and optically active 4-(polyalkoxyphenyl)-2-pyrrolidones of the following formula: wherein R', $R^{18}$, $R^{19}$ and X are as disclosed and described in U.S. Pat. No. 4,193,926. Rolipram is an example of a suitable Type IV PDE inhibitor included within the above formula.

Additional non-limiting examples of PDE IV inhibitors useful in practicing the instant invention include but are not limited to compounds having the following formulas and variations thereof.

The present invention further provides pharmaceutical compositions that include a compound of Formula (I) in combination with one of more members selected from the group consisting of the following: (a) Leukotriene biosynthesis inhibitors, 5-lipoxygenase (5-LO) inhibitors, and 5-lipoxygenase activating protein (FLAP) antagonists selected from the group consisting of zileuton; ABT-761; fenleuton; tepoxalin; Abbott-79175; Abbott-85761; N-(5-substituted)-thiophene-2-alkylsulfonamid-es of Formula (5.2.8); 2,6-di-tert-butylphenol hydrazones of Formula (5.2.10); Zeneca ZD-2138 of Formula (5.2.11); SB-210661 of Formula (5.2.12); pyridinyl-substituted 2-cyanonaphthalene compound L-739,010; 2-cyanoquinoline compound L-746,530; indole and quinoline compounds MK-591, MK-886, and BAY×1005; (b) Receptor antagonists for leukotrienes LTB4, LTC4, LTD4, and LTE4 selected from the group consisting of phenothiazin-3-one compound L-651,392; amidino compound CGS-25019c; benzoxazolamine compound ontazolast; benzenecarboximidamide compound BIIL 284/260;

compounds zafirlukast, ablukast, montelukast, pranlukast, verlukast (MK-679), RG-12525, Ro-245913, iralukast (CGP 45715A), and BAYx7195; (d) 5-Lipoxygenase (5-LO) inhibitors; and 5-lipoxygenase activating protein (FLAP) antagonists; (e) Dual inhibitors of 5-lipoxygenase (5-LO) and antagonists of platelet activating factor (PAF); (f) Theophylline and aminophylline; (g) COX-1 inhibitors (NSAIDs); and nitric oxide NSAIDs; (h) COX-2 selective inhibitor rofecoxib; (i) Inhaled glucocorticoids with reduced systemic side effects selected from the group consisting of prednisone, prednisolone, flunisolide, triamcinolone acetonide, beclomethasone dipropionate, budesonide, fluticasone propionate, and mometasone furoate; (j) Platelet activating factor (PAF) antagonists; (k) Monoclonal antibodies active against endogenous inflammatory entities; (1) Anti-tumor necrosis factor (TNFα) agents selected from the group consisting of etanercept, infliximab, and D2E7; (m) Adhesion molecule inhibitors including VLA-4 antagonists; (n) Immunosuppressive agents selected from the group consisting of cyclosporine, azathioprine, and methotrexate; or (O) anti-gout agents selected from the group consisting of colchicines.

Examples of pharmaceutically acceptable salts are organic acid addition salts formed with acids that form a physiological acceptable anion, for example, tosylate, methanesulfonate, malate, acetate, citrate, malonate, tartrate, succinate, benzoate, ascorbate, α-ketoglutarate, and α-glycerophosphate. Suitable inorganic salts may also be formed, including hydroCl, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain: binders, such as gum tragacanth, acacia, corn starch or gelatin; excipients, such as dicalcium phosphate; a disintegrating agent, such as corn starch, potato starch, alginic acid and the like; a lubricant, such as magnesium stearate; and a sweetening agent, such as sucrose, fructose, lactose or aspartame or a flavoring agent, such as peppermint, oil of wintergreen, or cherry flavoring. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients as enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid, a liquid or in a dermatological patch.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions, which can be used to deliver the compounds of formula I to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949. Useful dosages of Type IV PDE inhibitors are known to the art. For example, see, U.S. Pat. No. 5,877,180, Col. 12.

Generally, the concentration of the compound(s) of formula (I) in a liquid composition, such as a lotion, will be from about 0.1-25% wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 µg/kg, e.g., from about 10 to about 75 µg/kg of body weight per day, such as 3 to about 50 µg per kilogram body weight of the recipient per day, preferably in the range of 6 to 90 µg/kg/day, most preferably in the range of 15 to 60 µg/kg/day.

The compound is conveniently administered in unit dosage form; for example, containing 5 to 1000 µg, conveniently 10 to 750 µg, most conveniently, 50 to 500 µg of active ingredient per unit dosage form.

Ideally, the active ingredient should be administered to achieve peak plasma concentrations of the active compound of from about 0.1 to about 10 nM, preferably, about 0.2 to 10 nM, most preferably, about 0.5 to about 5 nM. This may be achieved, for example, by the intravenous injection of a 0.05 to 5% solution of the active ingredient, optionally in saline, or orally administered as a bolus containing about 1-100 µg of the active ingredient. Desirable blood levels may be maintained by continuous infusion to provide about 0.01-5.0 µg/kg/hr or by intermittent infusions containing about 0.4-15 µg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye. For example, it is desirable to administer the present compositions intravenously over an extended period of time following the insult that gives rise to inflammation.

The ability of a given compound of the invention to act as an $A_{2A}$ adenosine receptor agonist may be determined using pharmacological models which are well known to the art, or using tests described below.

The present compounds and compositions containing them are administered as pharmacological stressors and used in conjunction with any one of several noninvasive diagnostic procedures to measure aspects of myocardial perfusion. For example, intravenous adenosine may be used in conjunction with thallium-201 myocardial perfusion imaging to assess the severity of myocardial ischemia. In this case, any one of several different radiopharmaceuticals may be substituted for thallium-201 (e.g., technetium-99m-labeled radiopharmaceuticals (ie: Tc-99m-sestamibi, Tc-99m-teboroxime), iodine-123-labeled radiopharmaceuticals such as I-123-IPPA or BMIPP, rubidium-82, nitrogen-13, etc.). Similarly, one of the present compounds may be administered as a pharmacological stressor in conjunction with radionuclide ventriculography to assess the severity of myocardial contractile dysfunction. In this case, radionuclide ventriculographic studies may be first pass or gated equilibrium studies of the right and/or left ventricle. Similarly, a compound of formula (I) may be administered as a pharmacological stressor in conjunction with echocardiography to assess the presence of regional wall motion abnormalities. Similarly, the active compound may be administered as a pharmacological stressor in conjunction with invasive measurements of coronary blood flow such as by intracardiac catheter to assess the functional significance of stenotic coronary vessels.

There also is provided a method to diagnose myocardial perfusion abnormalities in a mammal comprising: (a) parenterally administering to said mammal an amount of a compound or composition as described above; and (b) performing a technique on the mammal to detect the presence of coronary artery stenoses, assess the severity of coronary artery stenoses or both. The myocardial dysfunction may be, for example, coronary artery disease, ventricular dysfunction and differences in blood flow through disease-free coronary vessels and/or stenotic coronary vessels. The technique to detect the presence and assess the severity of coronary artery disease may be, for example, radiopharmaceutical myocardial perfusion imaging, ventricular function imaging, or techniques for measuring coronary blood flow velocity. The radiopharmaceutical myocardial perfusion imaging may be, for example, planar scintigraphy, single photon emission computed tomography (SPECT), positron emission tomography (PET), nuclear magnetic resonance (NMR) imaging, perfusion contrast echocardiography, digital subtraction angiography (DSA) and ultrafast X-ray computed tomography (CINE CT). A radiopharmaceutical agent may be used in conjunction with the radiopharmaceutical myocardial perfusion imaging, and the radiopharmaceutical agent may comprise, for example, a radionuclide selected from the group consisting of thallium-201, technetium-99m, nitrogen-13, rubidium-82, iodine-123 and oxygen-15. When the radiopharmaceutical myocardial perfusion imaging is scintigraphy, the radiopharmaceutical agent may be thallium-201. The ventricular function imaging technique may be, for example, echocardiography, contrast ventriculography or radionuclide ventriculography. The method for measuring coronary blood flow velocity may be, for example, doppler flow catheter, digital subtraction angiography and radiopharmaceutical imaging techniques. These methods of diagnosis may also comprise the steps of: (a) administering to the human by intravenous infusion or by bolus injection an amount of a compound or composition as described above to provide coronary artery dilation; (b) administering a radiopharmaceutical agent comprising thallium-201 or technetium-99m to the human; and (c) performing the scintigraphy on the human in order to detect the presence and assess the severity of coronary artery disease. The radiopharmaceutical agent may be, for example, Tc-99m-sestamibi.

The method typically involves the administration of one or more compounds of formula (I) by intravenous infusion in doses which are effective to provide coronary artery dilation (approximately 0.25-500, preferably 1-250 mcg/kg/min). However, its use in the invasive setting may involve the intra-coronary administration of the drug in bolus doses of 0.5-50 mcg.

Preferred methods comprise the use of a compound of formula (I) as a substitute for exercise in conjunction with myocardial perfusion imaging to detect the presence and/or assess the severity of coronary artery disease in humans wherein myocardial perfusion imaging is performed by any one of several techniques including radiopharmaceutical myocardial perfusion imaging using planar scintigraphy or single photon emission computed tomography (SPECT), positron emission tomograph (PET), nuclear magnetic resonance (NMR) imaging, perfusion contrast echocardiography, digital subtraction angiography (DSA), or ultrafast X-ray computed tomography (CINE CT).

A method is also provided comprising the use of a compound of formula (I) as a substitute for exercise in conjunction with imaging to detect the presence and/or assess the severity of ischemic ventricular dysfunction in humans wherein ischemic ventricular dysfunction is measured by any one of several imaging techniques including echocardiography, contrast ventriculography, or radionuclide ventriculography. The myocardial dysfunction can be coronary artery disease, ventricular dysfunction, differences in blood flow through disease-free coronary vessels and stenotic coronary vessels and the like A method is also provided comprising the use of a compound of formula (I) as a coronary hyperemic agent in conjunction with means for measuring coronary blood flow velocity to assess the vasodilatory capacity (reserve capacity) of coronary arteries in humans wherein coronary blood flow velocity is measured by any one of several techniques including Doppler flow catheter or digital subtraction angiography.

Exemplary compounds of the invention are shown in Table 1, below, wherein Compound Numbers 1, 2, 4, and 32 are presented only for comparative purposes. Compounds are of formula (I), unless indicated.

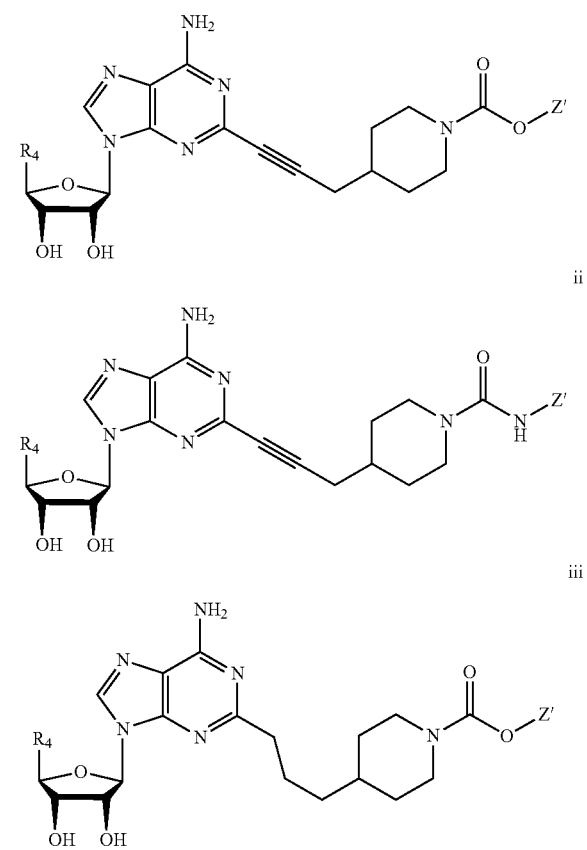

$R^4$=A: $CH_2OH$; B: C(O)NEthyl; C: C(O)NCyclopropyl;

| Compound Number | $R^4$ | Z' | Human $A_1$ (nM) | Human $A_{2A}$ (nM) | Human $A_3$ (nM) | Functional (nM) |
|---|---|---|---|---|---|---|
| 1 | C | phenyl | 34.68 | 0.5630 | 34.10 | 0.56 |
| 2 | C | phenyl | ++ | ++++ | ++ | ++++ |
| 3 | C | phenyl-$CF_3$ | ++ | ++++ | ++ | +++ |
| 4 | C | phenyl | ++ | ++++ | +++ | +++ |

-continued
| Compound Number | R⁴ | Z' | Human A₁ (nM) | Human A₂ₐ (nM) | Human A₃ (nM) | Functional (nM) |
|---|---|---|---|---|---|---|
| 5 | C | 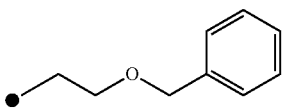 | ++ | ++++ | ++ | +++ |
| 6 | A | 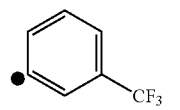 | ++ | ++++ | +++ | +++ |
| 7 | A | 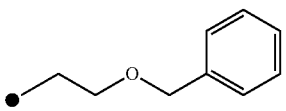 | ++ | ++++ | ++ | +++ |
| 8 | C | 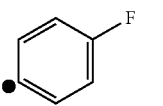 | ++ | ++++ | ++ | ++++ |
| 9 | C | 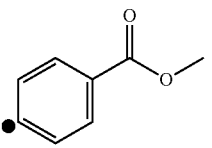 | ++ | ++++ | ++ | +++ |
| 10 | C | 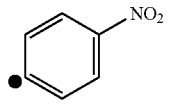 | ++ | ++++ | ++ | ++++ |
| 11 | A | 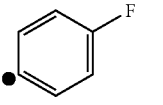 | ++ | ++++ | ++ | +++ |
| 12 | A | 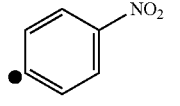 | ++ | ++++ | ++ | ++++ |
| 13 | A | 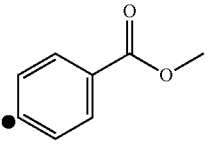 | ++ | ++++ | ++ | +++ |
| 14 | C | 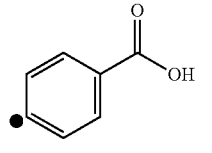 | + | +++ | + | ++ |
| 15 | B | 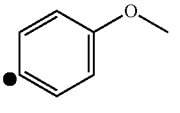 | ++ | ++++ | +++ | ++++ |
| 16 | B | 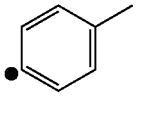 | ++ | ++++ | +++ | ++++ |

-continued

| Compound Number | R⁴ | Z' | Human A$_1$ (nM) | Human A$_{2A}$ (nM) | Human A$_3$ (nM) | Functional (nM) |
|---|---|---|---|---|---|---|
| 17 | C | 4-Cl-phenyl | ++ | ++++ | ++ | ++++ |
| 18 | C | 4-NO$_2$-phenyl | ++ | ++++ | ++ | ++++ |
| 19 | B | 4-NO$_2$-phenyl | ++ | ++++ | +++ | ++++ |
| 20 | C | 4-methyl-phenyl | ++ | ++++ | + | ++++ |
| 21 | C | 2-methoxy-phenyl | ++ | ++++ | ++ | +++ |
| 22 | C | 2-Cl-phenyl | ++ | ++++ | + | +++ |
| 23 | C | 4-methoxy-phenyl | ++ | ++++ | ++ | ++++ |
| 24 | B | 4-F-phenyl | ++ | ++++ | +++ | ++++ |
| 25 | B | 4-(methoxycarbonyl)-phenyl | + | +++ | ++ | +++ |
| 26 | B | 4-Cl-phenyl | ++ | ++++ | +++ | ++++ |
| 27 | A | 4-Cl-phenyl | ++ | ++++ | ++ | +++ |
| 28 | A | 4-methoxy-phenyl | ++ | ++++ | ++ | +++ |

| Compound Number | R⁴ | Z' | Human A₁ (nM) | Human A₂ₐ (nM) | Human A₃ (nM) | Functional (nM) |
|---|---|---|---|---|---|---|
| 29 | A | 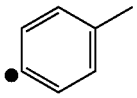 | ++ | ++++ | ++ | +++ |
| 30 | A | 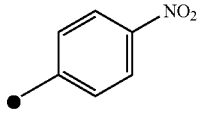 | ++ | +++ | ++ | +++ |
| 31 | B | 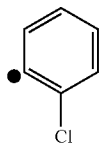 | ++ | ++++ | +++ | +++ |
| 32 | B | 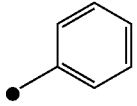 | + | ++++ | ++ | +++ |
| 33 | B | 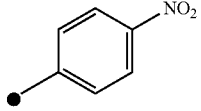 | ++ | ++++ | +++ | +++ |
| 34 | B | 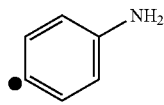 | ++ | +++ | ++ | ++++ |
| 35 | A | 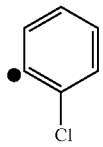 | ++ | ++++ | ++ | +++ |
| 36 | A | 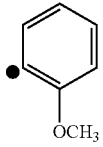 | ++ | ++++ | ++ | +++ |
| 37 (iii) | B | 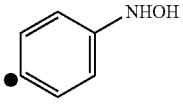 | ++ | ++++ | ++ | +++ |
| 38 (iii) | C | 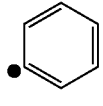 | + | ++ | + | ++ |
| 39 (iii) | C | 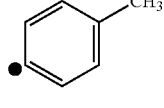 | + | ++ | + | ++ |
| 40 (iii) | C | 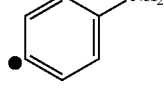 | + | +++ | + | ++ |

-continued

| Compound Number | R⁴ | Z' | Human A₁ (nM) | Human A₂ₐ (nM) | Human A₃ (nM) | Functional (nM) |
|---|---|---|---|---|---|---|
| 41 (iii) | C | 2-F phenyl | ++ | +++ | + | +++ |
| 42 | C | 2-Cl phenyl | + | +++ | + | + |
| 43 (ii) | C | 3-Cl phenyl | ++ | +++ | + | ++ |
| 44 (ii) | A | 2-F phenyl | ++ | +++ | ++ | + |
| 45 (ii) | A | 2-Cl phenyl | ++ | +++ | ++ | + |
| 46 (ii) | A | 3-Cl phenyl | ++ | +++ | ++ | ++ |
| 47 (ii) | C | 2,3-diCH₃ phenyl | ++ | ++++ | ++ | ++++ |
| 48 (ii) | C | 4-NH₂ phenyl | + | +++ | + | +++ |
| 49 | B | 2,3-diCl phenyl | ++ | ++++ | +++ | ++++ |
| 50 | B | 2,3-diF phenyl | ++ | ++++ | ++ | ++++ |
| 51 | C | 2,3-diCl phenyl | ++ | ++++ | ++ | ++++ |
| 52 | C | 2,3-diF phenyl | ++ | ++++ | ++ | ++++ |
| 53 | A | 2,3-diCH₃ phenyl | ++ | ++++ | ++ | +++ |

-continued

| Compound Number | R⁴ | Z' | Human $A_1$ (nM) | Human $A_{2A}$ (nM) | Human $A_3$ (nM) | Functional (nM) |
|---|---|---|---|---|---|---|
| 54 | A | 2,3-difluorophenyl | ++ | ++++ | ++ | +++ |
| 55 | A | 2,3-dichlorophenyl | ++ | ++++ | +++ | +++ |
| 56 | C | 3-nitrophenyl | ++ | ++++ | + | ++++ |
| 57 | C | 3,5-dibromophenyl | ++ | ++++ | ++ | +++ |

Legend for Compound Activity
++++ <1.0 nM
+++ <10 nM
++ <100 nM
+ >100 nM
● Indicates Point of Attachment of Z group to Y The invention will be further described by reference to the following detailed examples, which are given for illustration of the invention, and are not intended to be limiting thereof.

EXAMPLES

Nuclear magnetic resonance spectra for proton ($^1$H NMR) were recorded on a 300 MHz Varian Gemini 2000 (or similar instrument) spectrophotometer. The chemical shift values are expressed in ppm (parts per million) relative to tetramethylsilane. For data reporting, s=singlet, d=doublet, t=triplet, q=quartet, and m=multiplet. Mass spectra were measured on a Finnigan LCQ Advantage. Analytical HPLC was done on a Shimazdu LC10 or LC20 Systemtimes.150 mm) as described below. Preparative HPLC was performed on a Shimadzu Discovery HPLC with a Shim-pack VP-ODS C18 (20×100 mm) column operated at room temperature. Compounds were eluted at 30 mL/min with a gradient 20-80% of water (containing 0.1% TFA) to methanol over 15 minutes with UV detection at 254 nm using a SPD10A VP Tunable detector. All final compounds presented here were determined to be greater than 98% pure by HPLC. Flash chromatography was performed on Silicyle 60A gel (230-400 mesh) or using reusable chromatography columns and system from RT Scientific, Manchester N.H. All reactions were done under a nitrogen atmosphere in flame-dried glassware unless otherwise stated.

General Procedure 1: Representative Procedure for Piperidyl Alkyne Formation

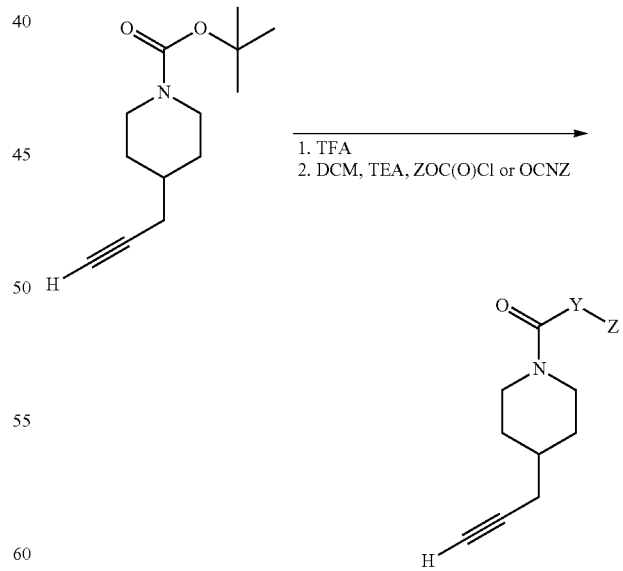

Neat TFA (trifluoroacetic acid) (4 mL) was added to tert-butyl 4-(prop-2-ynyl)piperidine-1-carboxylate (1.5 g, 18.56 mmol) at 0° C. and the solution allowed to come to r.t and stir an additional 3-12 h. The TFA was removed under reduced pressure to a thick oil. This oil was cooled to 0° C. and DCM (20 mL) and. TEA (5 mL) were then added followed by the dropwise addition of the appropriate chloroformate or isocyanate (~1.5 equiv). The mixture was stirred at room temperature under an $N_2$ atmosphere 24 h, with reaction progress monitored by TLC and LC/MS. The reaction was worked up by filtering the precipitate and washing 2-3 times with EtOAc followed by concentration under reduced pressure to a thick yellow oil. The crude reaction was purified by silica gel chromatography with a gradient of Hex/EtOAc (0-20%). The product was collected and concentrated under reduced pressure to often afford a yellowish oil often requiring further purification using the same purification conditions as previously stated. Compounds were isolated as odorous yellow oils in yields of 50-90% and characterized by LC/MS and or $^1H$ NMR spectroscopy. HPLC was run on a Shimadzu HPLC using a Water's Atlantis 4.6×150 mm 5 µm C18 column eluted with a 15 minute linear gradient of 45-95% MeOH/$H_2O$ (containing 0.1% formic acid). TLC was performed using EMD Chemicals Aluminumoxd 60 $F_{254}$ neutral plates developed with 20% EtOAc/Hex and visualized with under UV at 254 nm or through staining with Vanillin.

General Procedure 2: Representative Procedure for Sonogashira Coupling of Alkynes to 2-Iodoadenosine Analogs mixture was then filtered directly or 12-24 h after the addition of Silica bound scavengers Si-thiol and Si-TAAcOH from Silicycle, which were added to scavenge Cu and Palladium. The residue was washed 2-3 times with MeOH/EtOH and concentrated under reduced pressure to a thick brown oil. The crude reaction was purified by silica gel chromatography with a gradient of DCM/MeOH (0-15%). The product was collected and concentrated under reduced pressure to often afford a yellowish oily solid frequently requiring further purification using a C18 column (either preparative HPLC or standard flash column) with a gradient of MeOH/$H_2O$. Compounds were isolated as white solids in yields of 10-90% and characterized by LC/MS and or $^1H/^{13}C$ NMR spectroscopy. HPLC was run on a Shimadzu HPLC using a Water's Atlantis 4.6×150 mm 5 µm C18 column eluted with a 15 minute linear gradient of 45-95% MeOH/$H_2O$ (containing 0.1% formic acid). TLC was performed using EMD Chemicals Aluminumoxd 60 $F_{254}$ neutral plates developed with 10% MeOH/DCM and visualized with under UV at 254 nm or through staining with Vanillin.

Intermediate 1

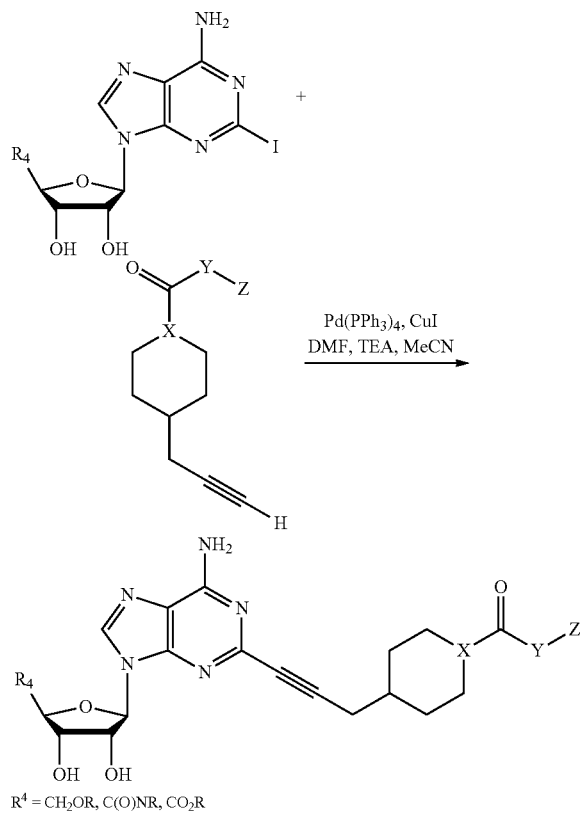

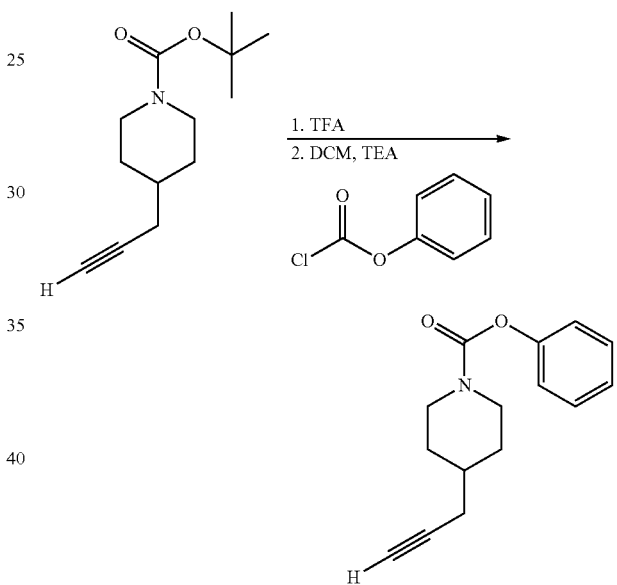

Phenyl 4-(prop-2-ynyl)piperidine-1-carboxylate. Phenyl chloroformate (6.2 g, 40.2 mmol) was added to a solution of tert-butyl 4-(prop-2-ynyl)piperidine-1-carboxylate (1.65 g, 13.4 mmol) according to general procedure 1. Yield=0.600 g, 34%. m/z MH$^+$=244.08. HPLC rt=10.3 min.

The appropriate alkyne (0.0800 mL, 0.1121 mmol) was added to a solution of N-Cyclopropyl-2-iodoadenosine-5'-uronamide, N-ethyl-2-iodoadenosine-5'-uronamide, or 2-iodoadenosine (0.0510 g, 0.1121 mmol) in DMF (5 mL). Acetonitrile (3 mL) and TEA (1 mL) were then added, with all solvents freshly degassed with Nitrogen for a minimum of 3 h. The mixture was stirred at room temperature under an $N_2$/argon atmosphere while Pd(PPh$_3$)$_4$ (catalytic, ~0.05 mol %) and CuI (catalytic, ~0.05 mol %) were added. The solution was allowed to stir at rt for 24-72 h, with reaction progress monitored by LC/MS. Additional alkyne, TEA, Pd(PPh$_3$)$_4$, and CuI were optionally added after 24 h if the reaction appeared to be proceeded sluggishly to drive the reaction to completion and consume all nucleotide starting material. The Intermediate 2

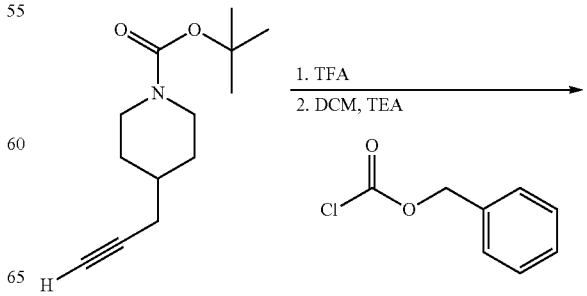

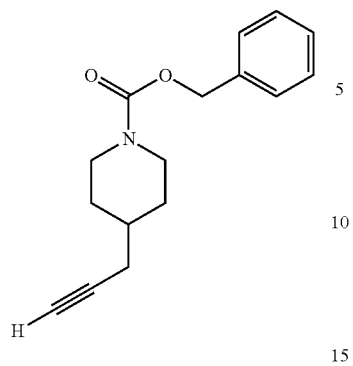

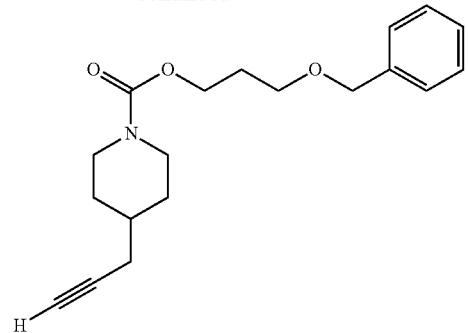

Benzyl 4-(prop-2-ynyl)piperidine-1-carboxylate. Benzyl chloroformate (6.9 g, 40.4 mmol) was added to a solution of tert-butyl 4-(prop-2-ynyl)piperidine-1-carboxylate (1.65 g, 13.4 mmol) according to general procedure 1. Yield=0.700 g, 37%. m/z MH$^+$=258.02. HPLC rt=10.2 min.

3-(benzyloxy)propyl 4-(prop-2-ynyl)piperidine-1-carboxylate. 3-(trifluoromethyl)phenyl chloroformate (5.0 g, 23.3 mmol) was added to a solution of tert-butyl 4-(prop-2-ynyl)piperidine-1-carboxylate (1.20 g, 5.37 mmol) according to general procedure 1. Yield=1.191 g, 70%. m/z MH$^+$=312.04. HPLC rt=13.9 min.

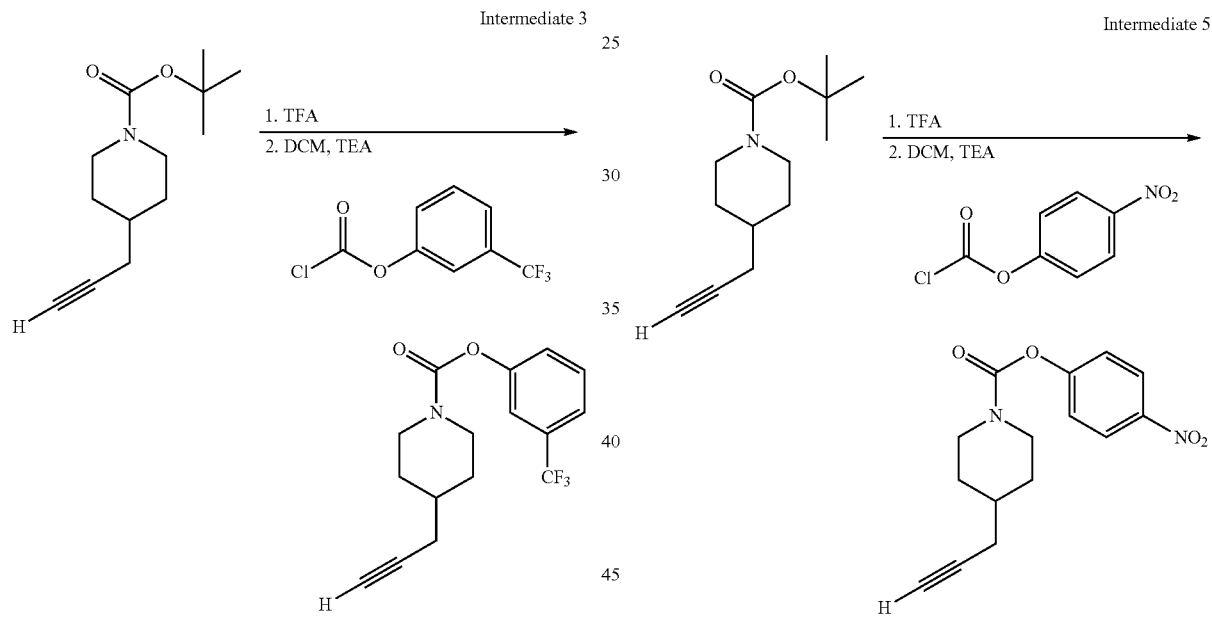

Intermediate 3

Intermediate 5

3-(trifluoromethyl)phenyl 4-(prop-2-ynyl)piperidine-1-carboxylate. 3-(trifluoromethyl)phenyl chloroformate (5.0 g, 29.3 mmol) was added to a solution of tert-butyl 4-(prop-2-ynyl)piperidine-1-carboxylate (1.50 g, 6.72 mmol) according to general procedure 1. Yield=1.1031 g, 64%. m/z MH$^+$=302.02. HPLC rt=10.8 min.

4-(nitro)phenyl 4-(prop-2-ynyl)piperidine-1-carboxylate. 4-(nitro)phenyl chloroformate (5.0 g, 24.8 mmol) was added to a solution of tert-butyl 4-(prop-2-ynyl)piperidine-1-carboxylate (4.25 g, 19.0 mmol) according to general procedure 1. Yield=5.72 g, 80%. m/z MH$^+$=289.04. HPLC rt=10.4 min.

Intermediate 4

Intermediate 6

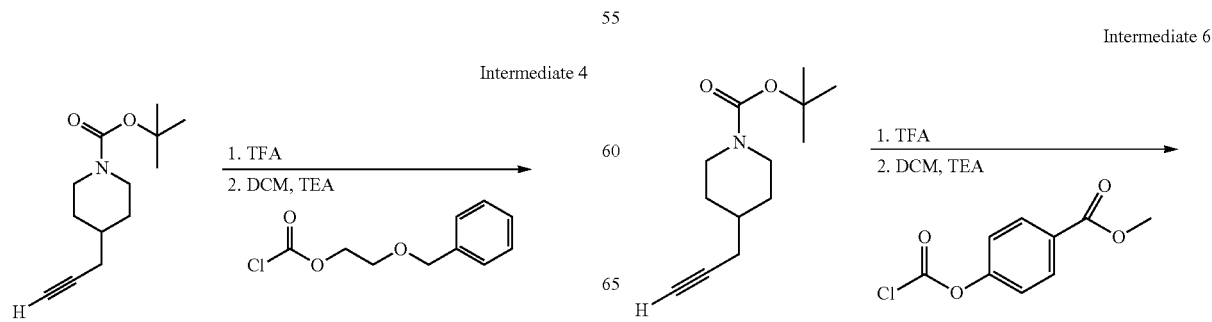

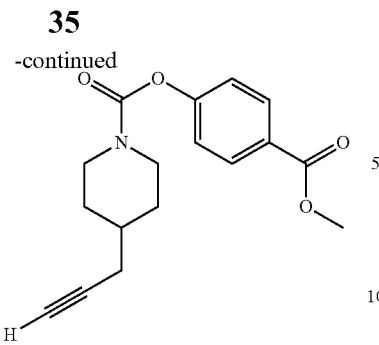
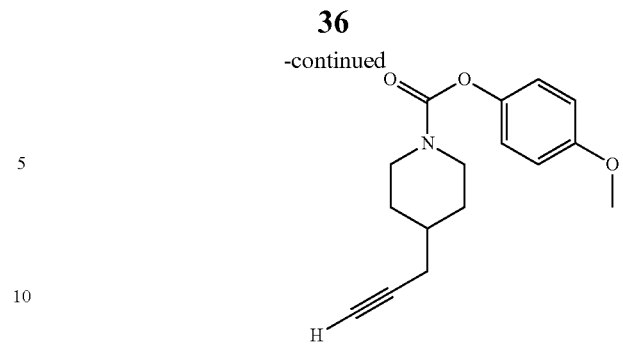

4-(methoxycarbonyl)phenyl 4-(prop-2-ynyl)piperidine-1-carboxylate. 4-(methoxycarbonyl)phenyl chloroformate (5.00 g, 23.3 mmol) was added to a solution of tert-butyl 4-(prop-2-ynyl)piperidine-1-carboxylate (4.00 g, 17.9 mmol) according to general procedure 1. Yield=5.54 g, 99%. m/z MH$^+$=302.02. HPLC rt=10.8 min.

4-(methoxy)phenyl 4-(prop-2-ynyl)piperidine-1-carboxylate. 4-(methoxy)phenyl chloroformate (5.00 g, 26.8 mmol) was added to a solution of tert-butyl 4-(prop-2-ynyl)piperidine-1-carboxylate (4.60 g, 20.9 mmol) according to general procedure 1. Yield=5.02 g, 90%. m/z MH$^+$=274.06. HPLC rt=12.2 min.

Intermediate 7

Intermediate 9

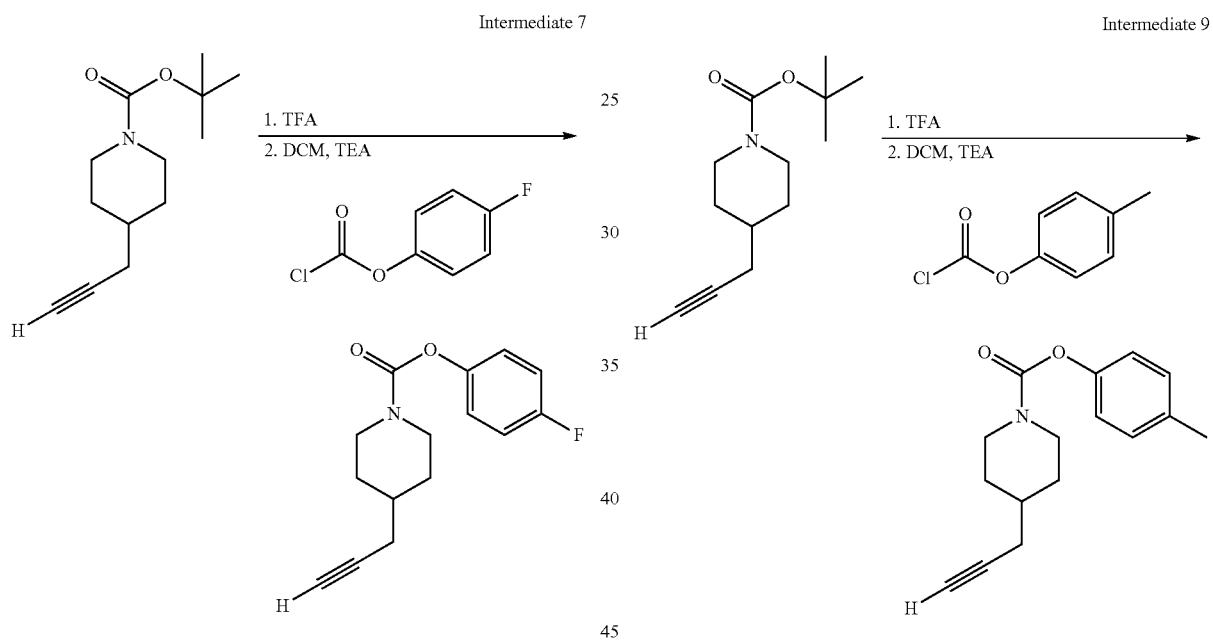

4-(fluoro)phenyl 4-(prop-2-ynyl)piperidine-1-carboxylate. 4-(fluoro)phenyl chloroformate (5.00 g, 28.6 mmol) was added to a solution of tert-butyl 4-(prop-2-ynyl)piperidine-1-carboxylate (4.90 g, 21.9 mmol) according to general procedure 1. Yield=5.54 g, 99%. m/z MH$^+$=262.03. HPLC rt=10.6 min.

4-(methyl)phenyl 4-(prop-2-ynyl)piperidine-1-carboxylate. 4-(methyl)phenyl chloroformate (5.00 g, 29.3 mmol) was added to a solution of tert-butyl 4-(prop-2-ynyl)piperidine-1-carboxylate (5.03 g, 22.6 mmol) according to general procedure 1. Yield=5.20 g, 90%. m/z MH$^+$=258.11. HPLC rt=13.0 min.

Intermediate 8

Intermediate 10

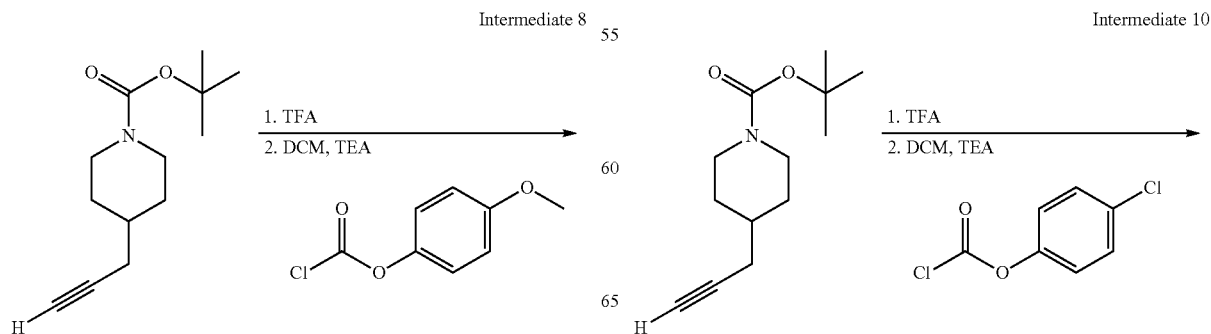

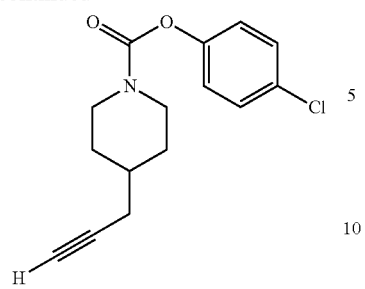

4-(chloro)phenyl 4-(prop-2-ynyl)piperidine-1-carboxylate. 4-(chloro)phenyl chloroformate (5.00 g, 26.2 mmol) was added to a solution of tert-butyl 4-(prop-2-ynyl)piperidine-1-carboxylate (5.50 g, 20.1 mmol) according to general procedure 1. Yield=4.83 g, 86%. m/z MH$^+$=278.13. HPLC rt=13.0 min.

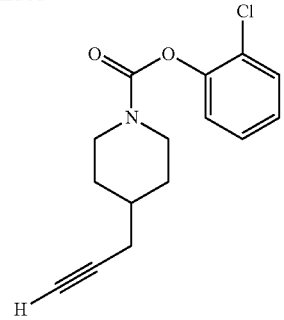

2-(chloro)phenyl 4-(prop-2-ynyl)piperidine-1-carboxylate. 2-(chloro)phenyl chloroformate (5.00 g, 26.2 mmol) was added to a solution of tert-butyl 4-(prop-2-ynyl)piperidine-1-carboxylate (4.50 g, 20.2 mmol) according to general procedure 1. Yield=4.56 g, 82%. m/z MH$^+$=278.13. HPLC rt=9.3 min.

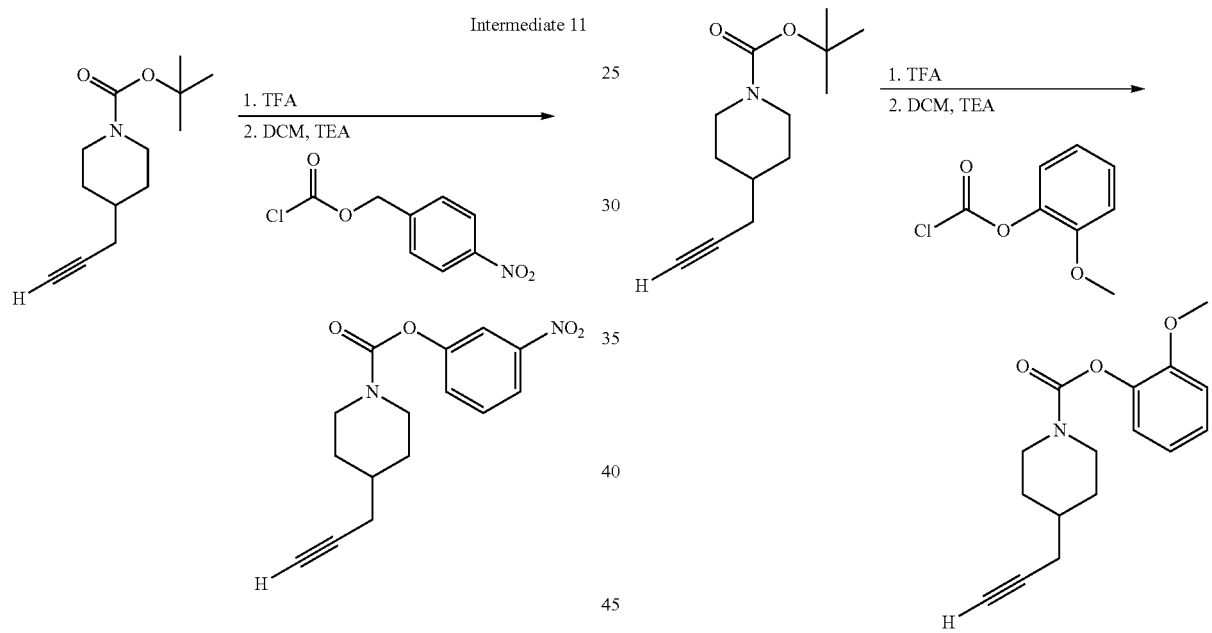

Intermediate 11

4-(nitro)benzyl 4-(prop-2-ynyl)piperidine-1-carboxylate. 4-(nitro)benzyl chloroformate (5.00 g, 23.2 mmol) was added to a solution of tert-butyl 4-(prop-2-ynyl)piperidine-1-carboxylate (3.98 g, 17.4 mmol) according to general procedure 1. Yield=4.66 g, 86%. m/z MH$^+$=302.98. HPLC rt=12.3 min.

Intermediate 13

2-(methoxy)phenyl 4-(prop-2-ynyl)piperidine-1-carboxylate. 2-(methoxy)phenyl chloroformate (5.00 g, 26.8 mmol) was added to a solution of tert-butyl 4-(prop-2-ynyl)piperidine-1-carboxylate (4.60 g, 20.6 mmol) according to general procedure 1. Yield=5.03 g, 89%. m/z MH$^+$=274.04. HPLC rt=8.7 min.

General Procedure 3: Representative Procedure for Piperidyl Carbamate Formation from Non-Commercially Available Chloroformates Intermediate 12

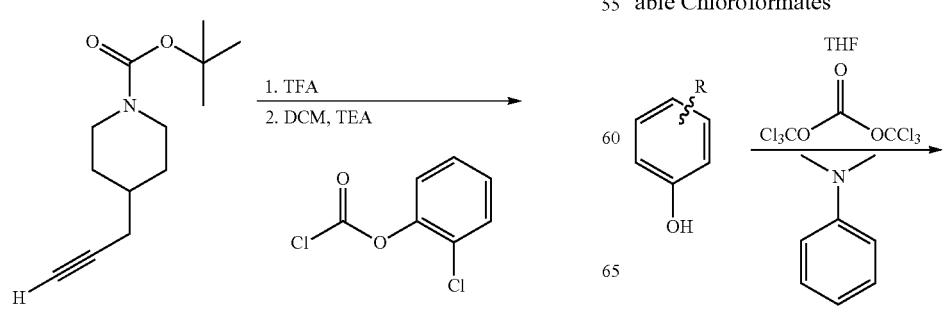

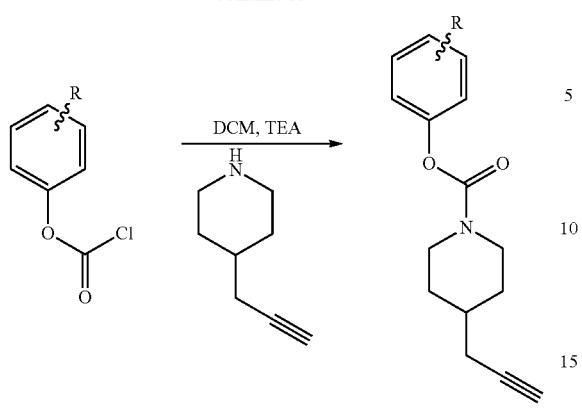

Triphosgene (2.849 g, 9.6 mmol) was dissolved in dry THF (60 ml) and cooled to 5° C. under inert atmosphere. To this solution, the disubstituted phenol (2.96 mmol) was added slowly as a solution in 1:1 THF and dimethylaniline (7.5 ml total volume). The reaction mixture was stirred at 5° C. for 10 minutes, and then stirred for an additional 3 h at room temperature. The resulting suspension of chloroformate was used as stated in the general procedure 1 to result in the corresponding piperidyl alkynes.

Intermediate 14

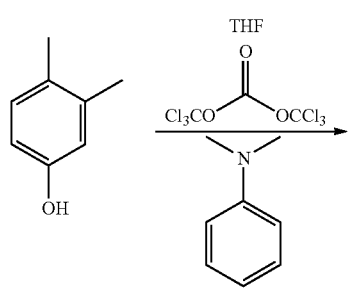

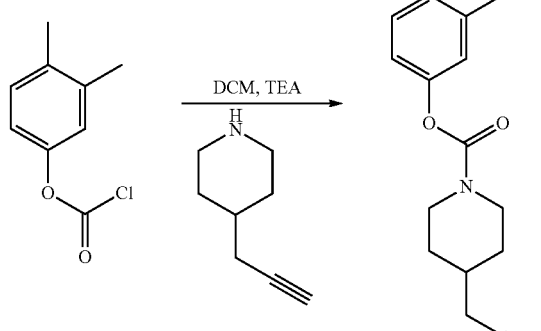

3,4-Dimethylphenyl 4-(prop-2-ynyl)piperidine-1-carboxylate. 3,4-Dimethyl-phenol (0.362 g, 2.96 mmol) was added as a solution in THF and dimethylaniline to a mixture of triphosgene (0.285 g, 0.96 mmol) in THF according to general procedure 3. Yield=0.350 g, 43%. m/z MH+=272.26. HPLC rt (retention time)=12.27 min.

Intermediate 15

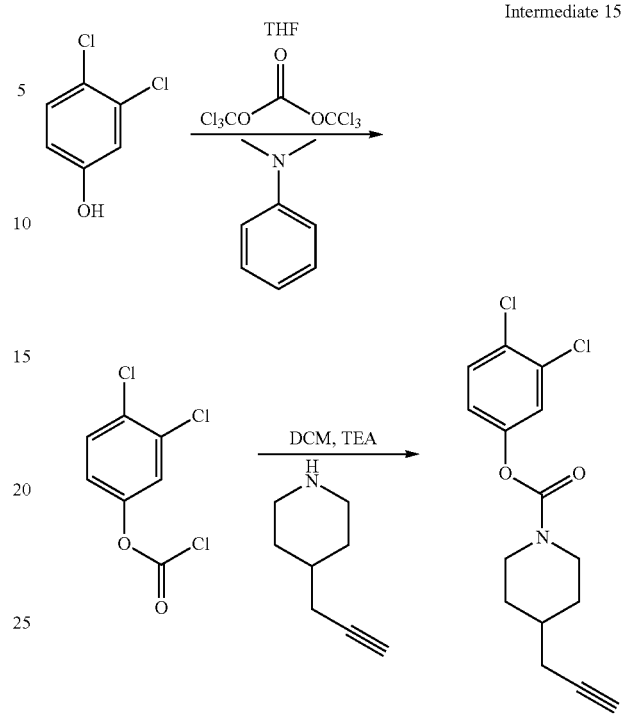

3,4-Dichlorophenyl 4-(prop-2-ynyl)piperidine-1-carboxylate. 3,4-Dichloro-phenol (4.83 g, 29.6 mmol) was added as a solution in THF and dimethylaniline to a mixture of triphosgene (2.849 g, 9.6 mmol) in THF according to general procedure 3. Yield=5.3 g, 57%. m/z MH+=312.14. HPLC rt=12.38 min.

Intermediate 16

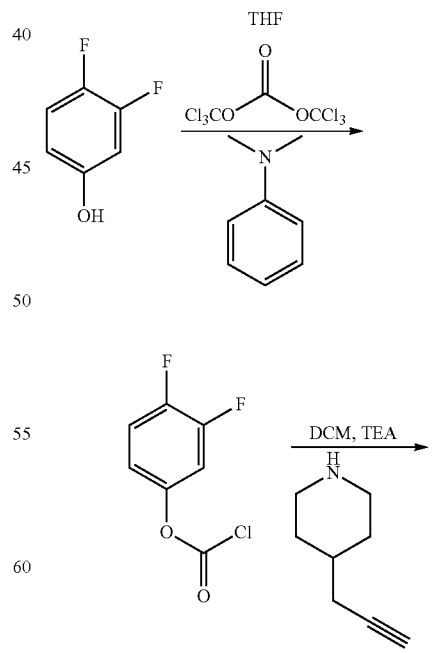

3,4-Difluorophenyl 4-(prop-2-ynyl)piperidine-1-carboxylate. 3,4-Difluoro-phenol (3.85 g, 29.6 mmol) was added as a solution in THF and dimethylaniline to a mixture of triphosgene (2.849 g, 9.6 mmol) in THF according to general procedure 3. Yield=4.6 g, 56%. m/z MH+=280.15. HPLC rt=11.88 min.

g, 9.6 mmol) in THF according to general procedure 3. Yield=5.53 g, 86%. m/z MH+=289.18. HPLC rt=11.78 min.

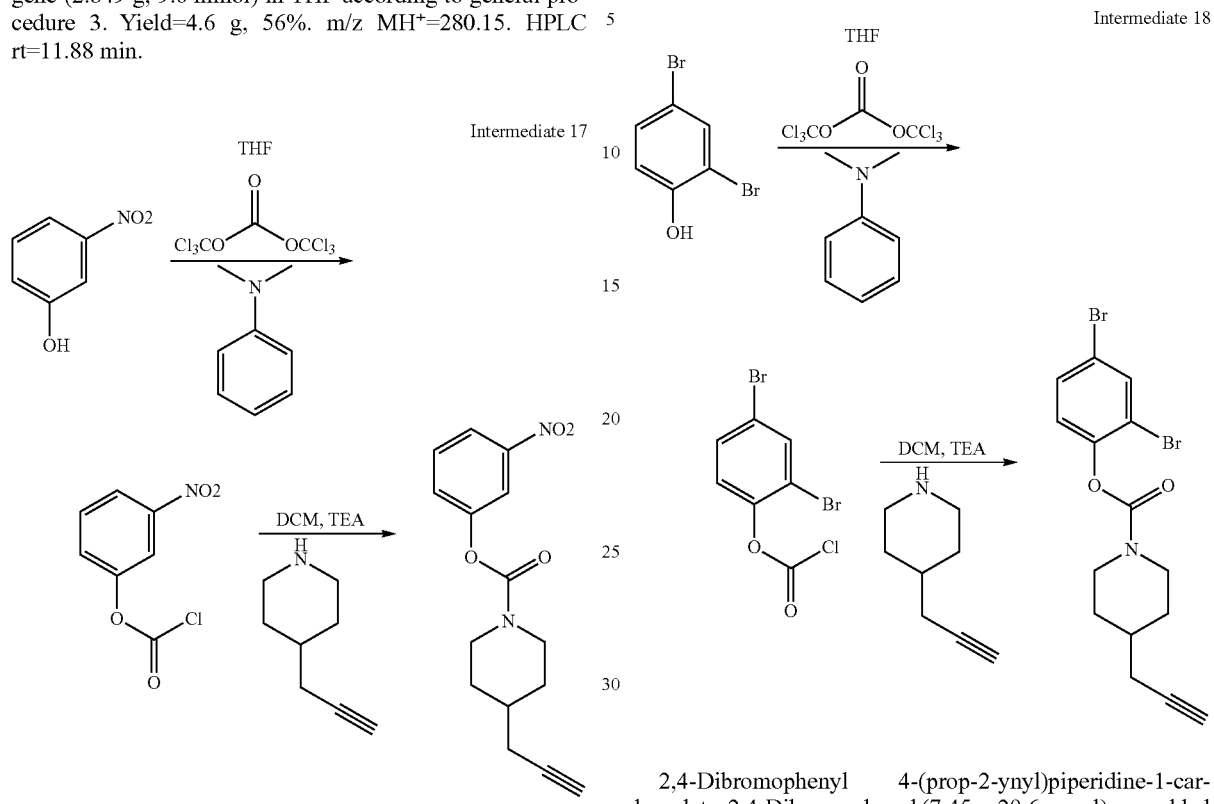

3-Nitrophenyl 4-(prop-2-ynyl)piperidine-1-carboxylate. 3-Nitrophenol (4.12 g, 29.6 mmol) was added as a solution in THF and dimethylaniline to a mixture of triphosgene (2.849

2,4-Dibromophenyl 4-(prop-2-ynyl)piperidine-1-carboxylate. 2,4-Dibromophenol (7.45 g, 29.6 mmol) was added as a solution in THF and dimethylaniline to a mixture of triphosgene (2.849 g, 9.6 mmol) in THF according to general procedure 3. Yield=6.09 g, 68%. m/z MH+=402.22. HPLC rt=12.49 min.

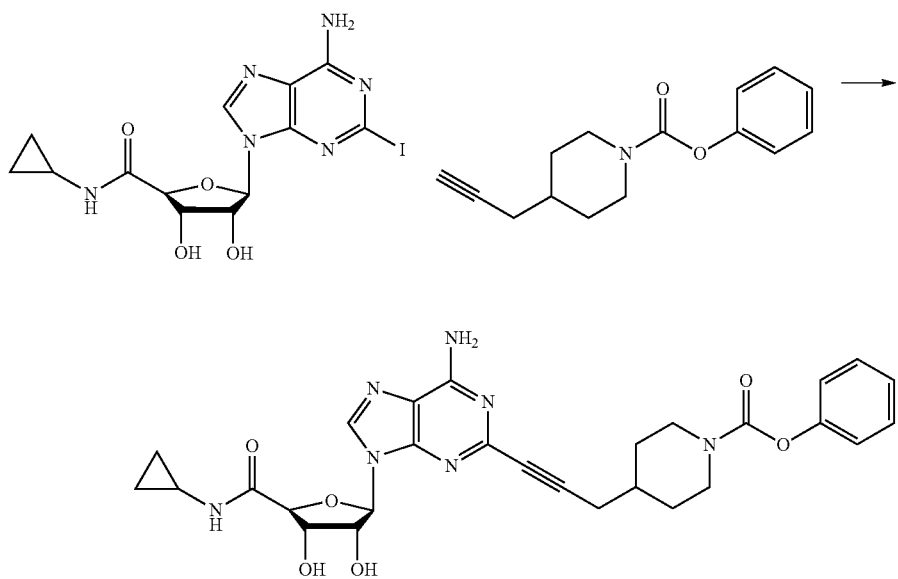

N-Cyclopropyl 2-{3-[1-(phenyloxycarbonyl)-4-piperidinyl]-1-propyn-1-yl}adenosine-5'-uronamide. Batch: JR28-23. Phenyl 4-(prop-2-ynyl)piperidine-1-carboxylate, batch JR28-11 (0.0800 mL, 0.1121 mmol) was added to a solution of N-Cyclopropyl-2-iodoadenosine-5'-uronamide (0.0510 g, 0.1121 mmol) according to general procedure 2. Yield=19.0 mg, 31%. $^1$H NMR (CD$_3$OD) δ 8.40 (s, 1H), 8.20 (s, 1H), 7.39-7.07 (dt, 5H), 6.02 (d, 1H), 4.39 (m, 1H), 3.31-2.90 (2×t, s, 4H), 2.71 (m, 4H), 2.49 (m, 1H), 1.98 (b d, 4H), 1.43-1.18 (2×m, 5H) 0.95-0.75 (2×m, 4H). m/z MH$^+$=562.19. HPLC rt=9.3 min.

JR28-13 (0.0800 mL, 0.1121 mmol) was added to a solution of N-Cyclopropyl-2-iodoadenosine-5'-uronamide (0.0510 g, 0.1121 mmol) according to general procedure 2. Yield=26.2 mg, 41%. $^1$H NMR (CD$_3$OD) δ 8.39 (s, 1H), 8.33 (s, 1H), 7.34-7.32 (dt, 5H), 6.01 (d, 1H), 5.10 (m, 2H), 4.81-4.79 (m, 1H), 4.4 (s, 2H), 4.20-4.15 (d, 2H), 2.50 (2×m, 4H), 2.42 (d, 1H), 1.84-1.85 (b d, 4H), 1.30-1.27 (b m, 5H) 0.76-53 (2×m, 4H). $^{13}$C(CD$_3$OD) δ 173.72, 157.17, 156.97, 150.81, 147.86, 142.99, 138.23, 129.53, 129.06, 128.83, 120.30, 90.33, 86.41, 85.75, 74.74, 73.89, 68.23, 45.13, 36.60, 32.56, 26.63, 23.38, 6.96. m/z MH$^+$=576.19. HPLC rt=9.8 min.

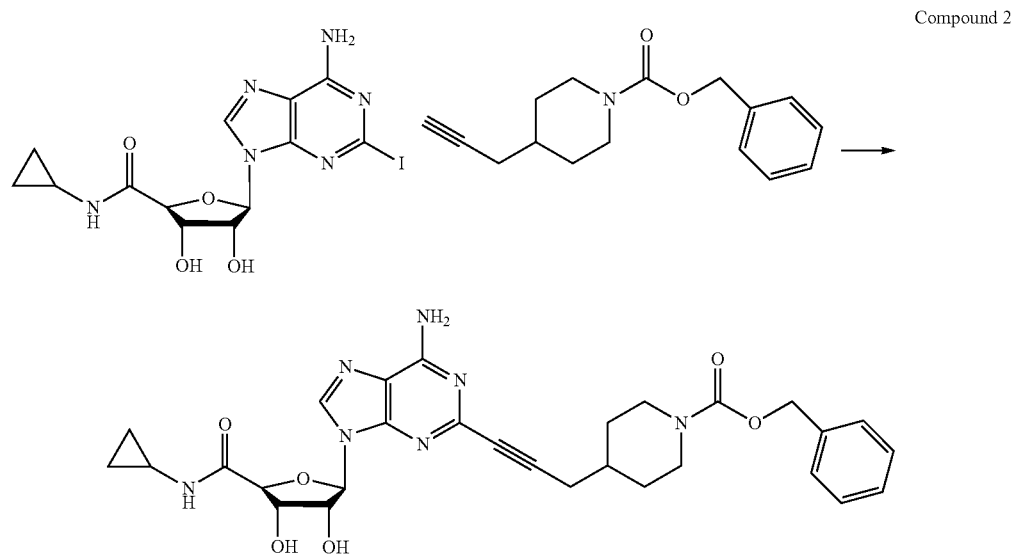

Compound 2

N-Cyclopropyl 2-{3-[1-(benzyloxycarbonyl)-4-piperidinyl]-1-propyn-1-yl}adenosine-5'-uronamide. Batch: JR28-25. Benzyl 4-(prop-2-ynyl)piperidine-1-carboxylate, batch

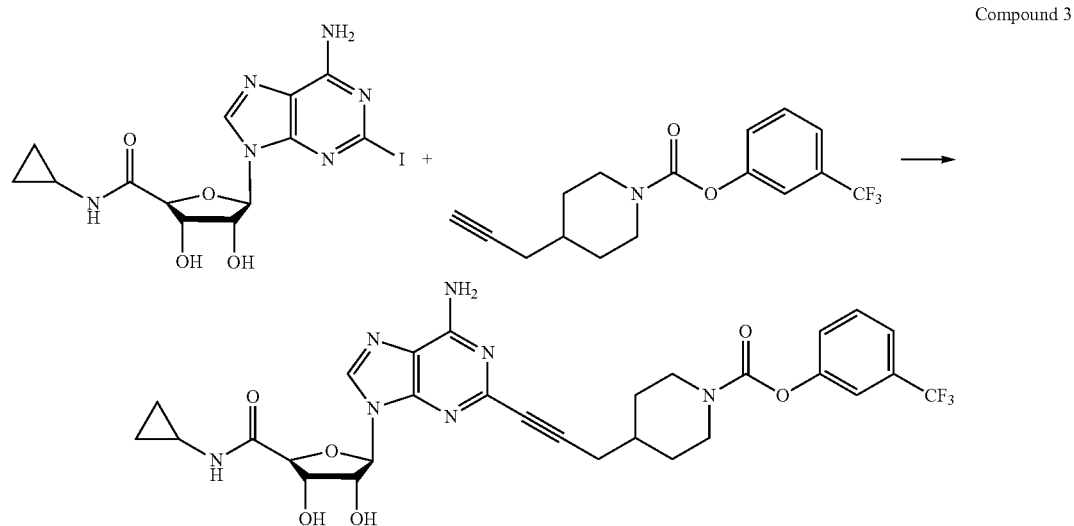

Compound 3

N-Cyclopropyl 2-{3-[1-(3-(trifluoromethyl)phenoxycarbonyl)-4-piperidinyl]-1-propyn-1-yl}adenosine-5'-uronamide. Batch: JR28-71. 4-Trifluoromethyl 4-(prop-2-ynyl)piperidine-1-carboxylate, batch JR28-57 (0.080 mL, 0.1121 mmol) was added to a solution of N-Cyclopropyl-2-iodoadenosine-5'-uronamide (0.0500 g, 0.1121 mmol) according to general procedure 2. Yield: 54.5 mg, 82%. $^1$H NMR (CD$_3$OD) δ 8.30 (s, 1H), 7.38-7.06 (3×m, 5H), 5.94 (d, 1H), 4.71 (m, 1H), 4.32-4.17 (2×m, 7H), 3.92-3.72 (2×d, 2H), 3.10-2.90 (2×bt, 4H), 2.48 (d, 5H), 1.93 (2×m, 5H). m/z MH$^+$=509.18. HPLC rt=5.3 min.

Compound 5

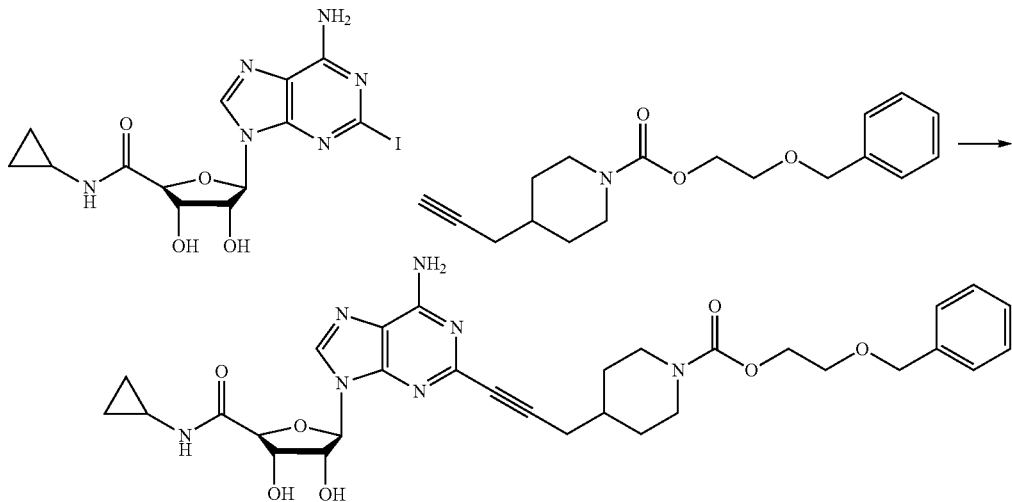

general procedure 2. Yield=32.0 mg, 46%. $^1$H NMR (CD$_3$OD) δ 8.41 (s, 1H), 7.60-7.34 (m, 4H), 6.02 (d, 1H), 4.84 (m, 1H), 4.31 (m, 2H), 3.00 (2×m, 2H), 2.99-2.94 (2×m, 4H), 2.71 (m, 1H), 2.46 (d, 4H), 1.98-1.30 (2×m, 5H), 0.77-0.58 (2×m, 4H). m/z MH$^+$=630.18. HPLC rt=10.5 min.

N-Cyclopropyl 2-{3-[1-(2-(benzyloxy)ethoxycarbonoyl)-4-piperidinyl]-1-propyn-1-yl}adenosine-5'-uronamide. Batch: JR28-69. 2-(Benzyloxy)ethyl 4-(prop-2-ynyl)piperidine-1-carboxylate, batch JR28-55 (0.080 mL, 0.1121 mmol) was added to a solution of N-Cyclopropyl-2-iodoadenosine-5'-uronamide (0.0500 g, 0.1121 mmol) according to general procedure 2. Yield=20.0 mg, 29%. $^1$H NMR (CD$_3$OD) δ 8.20 (s, 1H), 7.55 (s, 1H), 7.33-7.30 (m, 5H), 6.02 (d, 1H), 4.86 (m, 1H), 4.53 (m, 2H), 4.41-4.13 (4×m, 8H), 3.74-3.66 (m, 4H), 2.70 (m, 1H), 2.41-2.36 (d, 4H), 1.87-1.26 (2×m, 5H), 0.76-0.54 (2×m, 4H). m/z MH$^+$=620.22. HPLC rt=9.6 min.

Compound 4

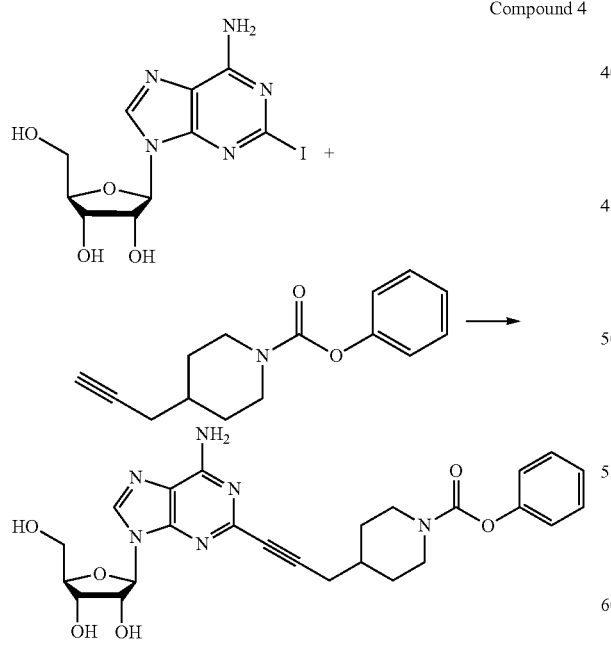

2-{3-[1-(Phenoxycarbonyl)piperidin-4-yl]propyn-1-yl}adenosine. Batch: AB-9-97. Phenyl 4-(prop-2-ynyl)piperidine-1-carboxylate, batch JR28-11 (0.329 g, 1.352 mmol)

Compound 6

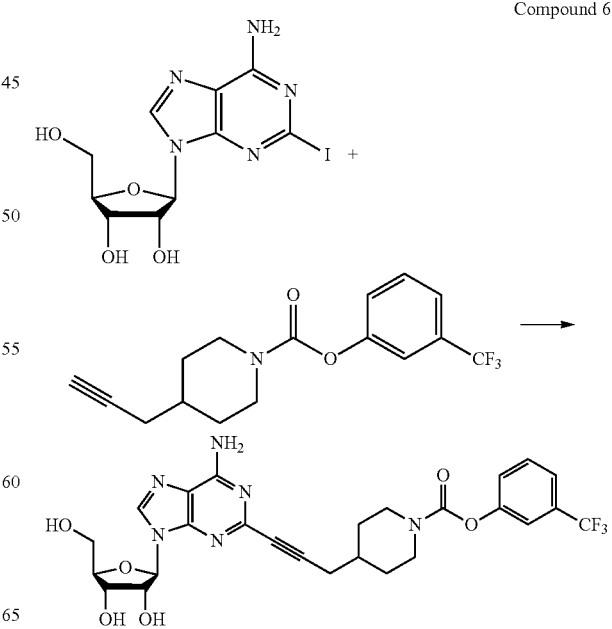

2-{3-[1-(3-Trifluoromethyl)phenoxycarbonyl)piperidin-4-yl]propyn-1-yl}adenosine. Batch: AB-9-129. 4-Trifluoromethyl 4-(prop-2-ynyl)piperidine-1-carboxylate, batch JR28-57 (0.844 g, 2.71 mmol) was added to a solution of 2-iodoadenosine (0.978 g, 2.488 mmol) according to general procedure 2. Yield: 1.205 g, 84%. $^1$H NMR (CD$_3$OD) δ 8.40 (s, 1H), 7.59-7.37 (3×m, 4H), 5.95 (d, 1H), 4.71 (m, 2H), 4.31-4.16 (2×m, 5H), 3.91-3.75 (2×d, 2H), 3.09-2.94 (2×bt, 4H), 2.48 (d, 5H), 1.96-1.44 (2×m, 5H). m/z MH$^+$=577.13. HPLC rt=11.2 min.

N-Cyclopropyl 2-{3-[1-(4-fluorophenoxycarbonyl)-4-piperidinyl]-1-propyn-1-yl}adenosine-5'-uronamide. Batch: JR28-97. 4-Fluorophenoxy 4-(prop-2-ynyl)piperidine-1-carboxylate, batch JR28-87 (0.150 mL, 0.1681 mmol) was added to a solution of N-Cyclopropyl-2-iodoadenosine-5'-uronamide (0.075 g, 0.1681 mmol) according to general procedure 2. Yield=43.0 mg, 44%. $^1$H NMR (CD$_3$OD) δ 8.41 (s, 1H), 7.65-7.61 (m, 4H), 7.01 (d, 1H), 6.02 (d, 1H), 4.83 (m, 1H), 4.41-4.38 (m, 2H), 3.33-2.95 (3×m, 6H), 2.71 (m, 1H), 2.48-2.46 (d, 4H), 1.97-1.92 (2×m, 5H), 0.78-0.55 (2×m, 4H). m/z MH$^+$=580.24. HPLC rt=9.3 min.

Compound 7

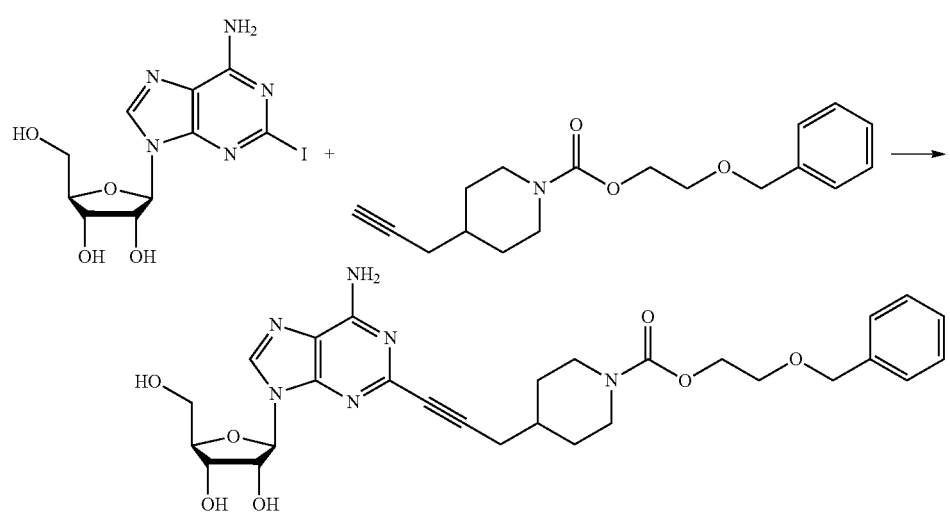

2-{3-[1-((2-Benzyloxy)ethoxycarbonyl)piperidin-4-yl]propyn-1-yl}adenosine. Batch: AB-9-131. 2-(benzyloxy)ethyl 4-(prop-2-ynyl)piperidine-1-carboxylate, batch JR28-55 (0.780 g, 2.59 mmol) was added to a solution of 2-iodoadenosine (0.936 g, 2.381 mmol) according to general procedure 2. Yield: 0.575 g, 43%. $^1$H NMR (CD$_3$OD) δ 8.29 (s, 1H), 7.31 (m, 5H), 5.93 (d, 1H), 4.54 (s, 2H), 4.70-4.14 (3×m, 5H), 3.87-3.66 (2×m, 6H), 2.80 (bs, 4H), 2.42 (d, 5H), 1.89-1.50 (2×m, 5H). m/z MH$^+$=567.17. HPLC rt=8.0 min.

Compound 8

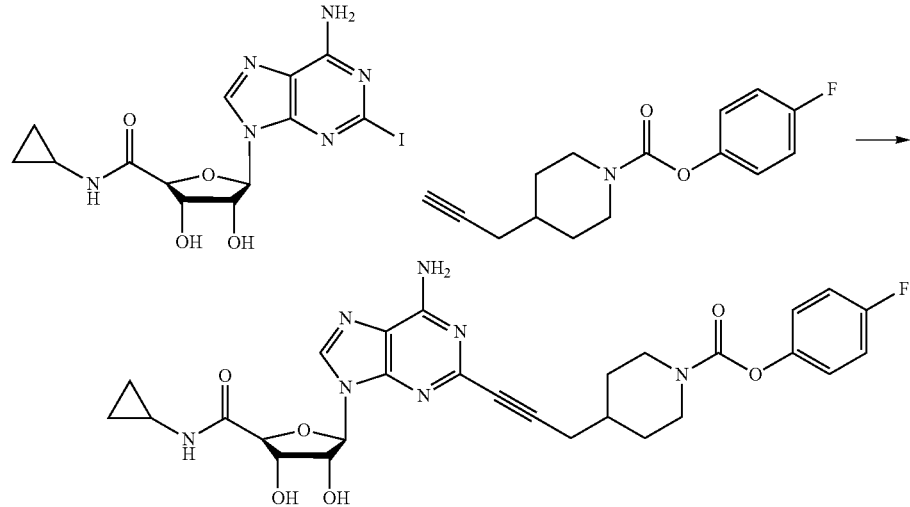

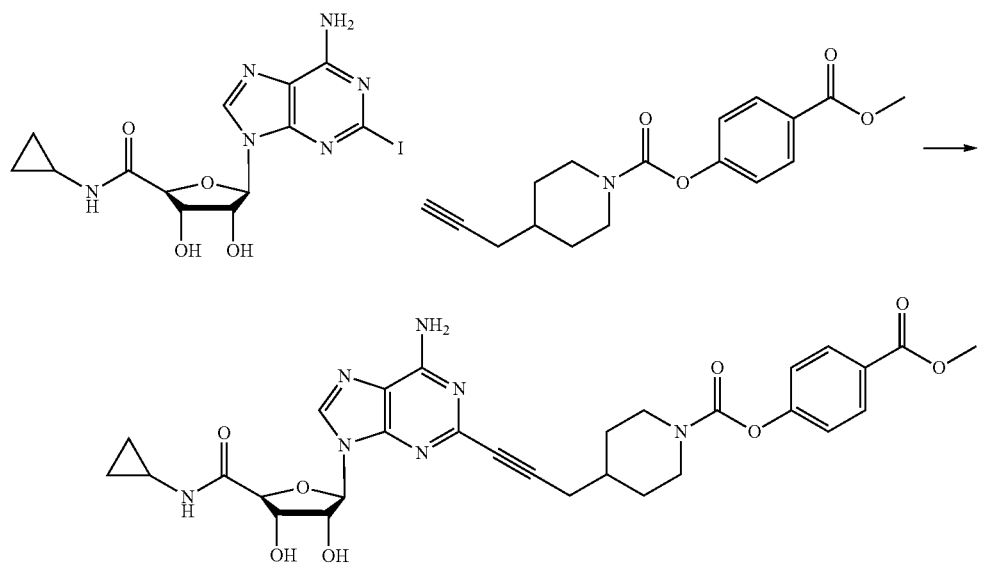

Compound 9

N-Cyclopropyl 2-{3-[1-(4-methoxycarbonylphenoxycarbanoyl)-4-piperidinyl]-1-propyn-1-yl}adenosine-5'-uronamide. Batch: JR28-95. 4-(methoxycarbonyl)phenyl 4-(prop-2-ynyl)piperidine-1-carboxylate, batch JR28-85 (0.150 mL, 0.2241 mmol) was added to a solution of N-Cyclopropyl-2-iodoadenosine-5'-uronamide 0.100 g, 0.2241 mmol) according to general procedure 2. Yield=68.9 mg, 50%. $^1$H NMR (CD$_3$OD) δ 8.40 (s, 1H), 8.04-8.02 (m, 3H), 7.23-7.21 (d, 2H), 6.02 (d, 1H), 4.81 (m, 1H), 4.32 (m, 2H), 3.89 (s, 4H), 3.09-2.71 (2×bt, 4H), 2.72 (m, 1H), 2.49 (d, 4H), 1.98-1.43 (2×m, 5H), 0.78-0.54 (2×m, 4H). m/z MH$^+$=620.25. HPLC rt=9.5 min.

N-Cyclopropyl 2-{3-[1-(4-nitrophenyloxycarbonyl)-4-piperidinyl]-1-propyn-1-yl}adenosine-5'-uronamide. Batch: JR28-93. 4-Nitrophenyl 4-(prop-2-ynyl)piperidine-1-carboxylate, batch JR28-83 (0.150 mL, 0.2241 mmol) was added to a solution of N-Cyclopropyl-2-iodoadenosine-5'-uronamide (0.100 g, 0.2241 mmol) according to general procedure 2. Yield=47.0 mg, 35%. $^1$H NMR (CD$_3$OD) δ 8.41 (s, 1H), 8.29-8.24 (m, 3H), 7.38-7.34 (d, 2H), 6.02 (d, 1H), 4.80 (m, 1H), 4.42-4.19 (m, 4H), 3.12-2.95 (2×bt, 4H), 2.71 (m, 1H), 2.49 (d, 4H), 1.98-1.47 (2×m, 5H), 0.78-0.54 (2×m, 4H). m/z MH$^+$=607.26. HPLC rt=9.1 min.

Compound 10

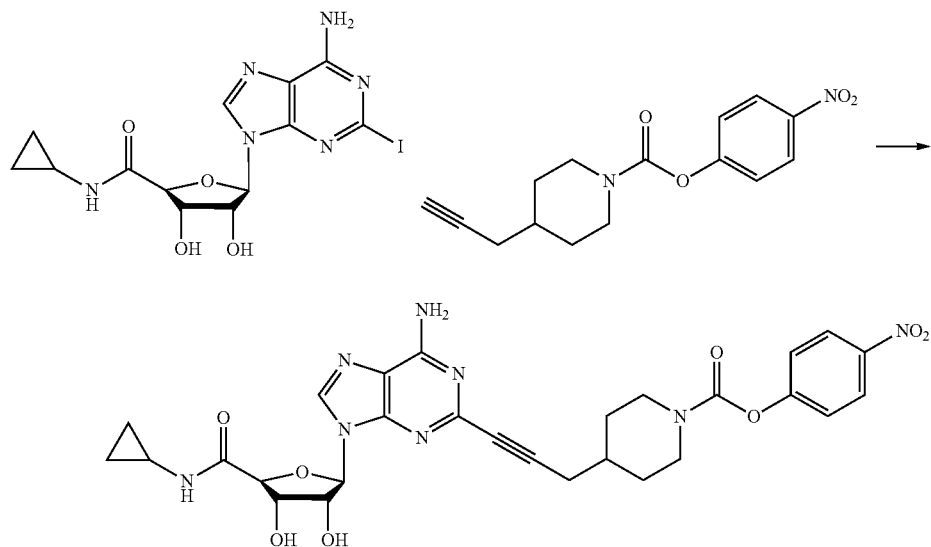

Compound 11

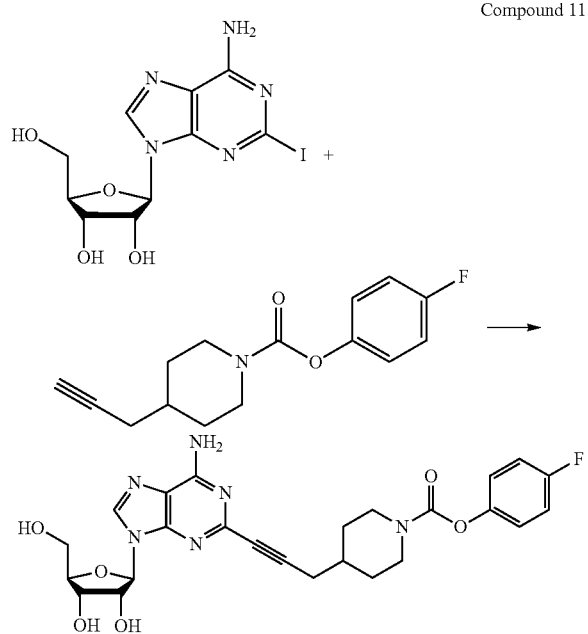

2-{3-[1-((4-Fluorophenoxy)carbonyl)piperidin-4-yl]pro-pyn-1-yl}adenosine. Batch: AB-9-147. 4-fluorophenyl 4-(prop-2-ynyl)piperidine-1-carboxylate, batch JR28-97 (0.700 g, 2.68 mmol) was added to a solution of 2-iodoadenosine (0.812 g, 2.065 mmol) according to general procedure 2. Yield: 0.902 g, 83%. $^1$H NMR (CD$_3$OD) δ 8.34 (s, 1H), 7.11 (m, 4H), 5.98 (d, 1H), 4.76 (m, 2H), 4.37-4.19 (2×m, 3H), 3.95-3.75 (2×d, 2H), 3.07-2.93 (2×bt, 4H), 2.47 (d, 5H), 1.98-1.44 (2×m, 5H). m/z MH$^+$=527.19. HPLC rt=7.6 min.

Compound 12

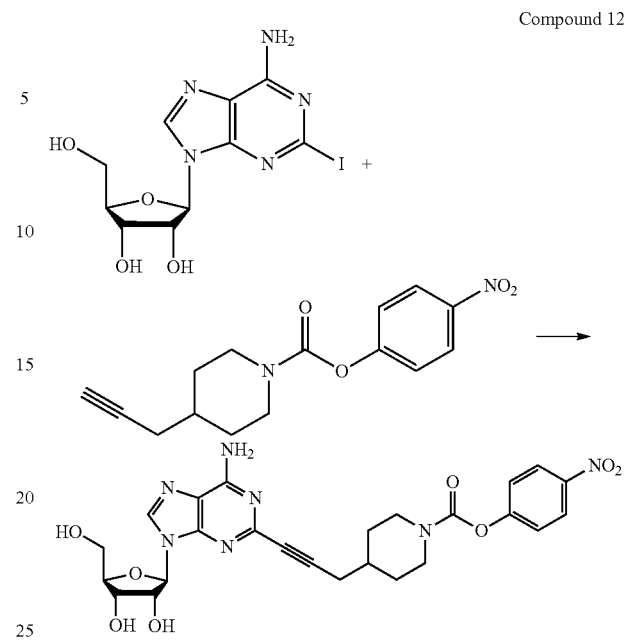

2-{3-[1-((4-Nitrophenoxy)carbonyl)piperidin-4-yl]pro-pyn-1-yl}adenosine. Batch: AB-9-149. 4-nitrophenyl 4-(prop-2-ynyl)piperidine-1-carboxylate, batch JR28-97 (0.630 g, 2.185 mmol) was added to a solution of 2-iodoadenosine (0.727 g, 1.849 mmol) according to general procedure 2. Yield: 1.192 g, 65%. %. $^1$H NMR (CD$_3$OD) δ 8.26 (m, 1H), 8.25-7.34 (2×m, 4H), 5.94 (d, 1H), 4.72 (m, 2H), 4.32-4.14 (2×m, 3H), 3.91-3.71 (2×d, 2H), 3.17-2.90 (2×bt, 4H), 2.48 (d, 5H), 1.45 (m, 5H). m/z MH$^+$=554.15. HPLC rt=7.3 min.

Compound 13

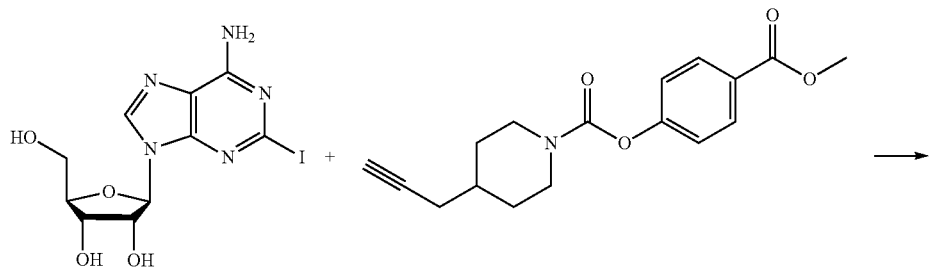

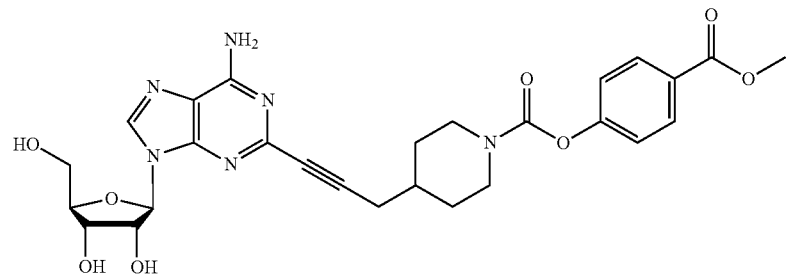

2-{3-[1-((4-Methoxycarbonylphenoxy)carbonyl)piperidin-4-yl]propyn-1-yl}adenosine. Batch: AB-9-151. 4-(methoxycarbonyl)phenyl 4-(prop-2-ynyl)piperidine-1-carboxylate, batch JR28-85 (0.670 g, 2.223 mmol) was added to a solution of 2-iodoadenosine (0.675 g, 1.717 mmol) according to general procedure 2. Yield: 0.648 g, 67%. $^1$H NMR (CD$_3$OD) δ 8.30 (s, 1H), 8.04-7.20 (2×m, 4H), 5.94 (d, 1H), 4.69 (m, 2H), 4.32-3.71 (4×m, 8H), 3.91-2.71 (2×d, 2H), 3.16-2.90 (2×bt, 4H), 2.48 (d, 5H), 1.98-1.45 (2×m, 5H). m/z MH$^+$=567.14. HPLC rt=7.9 min.

noxycarbanoyl)-4-piperidinyl]-1-propyn-1-yl} adenosine-5'-uronamide, batch JR28-95, ATL360 (0.0060 g, 0.0097 mmol) was added to a solution of THF (0.5 mL) and H$_2$O (1 mL). 1 N LiOH (1 mL) was added, and the mixture was stirred at room temperature for 3 hours. The mixture was evaporated down to afford a pure white solid. Yield=5.0 mg, 85%. $^1$H NMR (CD$_3$OD) δ 8.38 (m, 2H), 8.04-8.01 (m, 3H), 7.20-7.17 (d, 2H), 6.02 (d, 1H), 4.81 (m, 1H), 4.41-4.20 (m, 4H), 3.14-

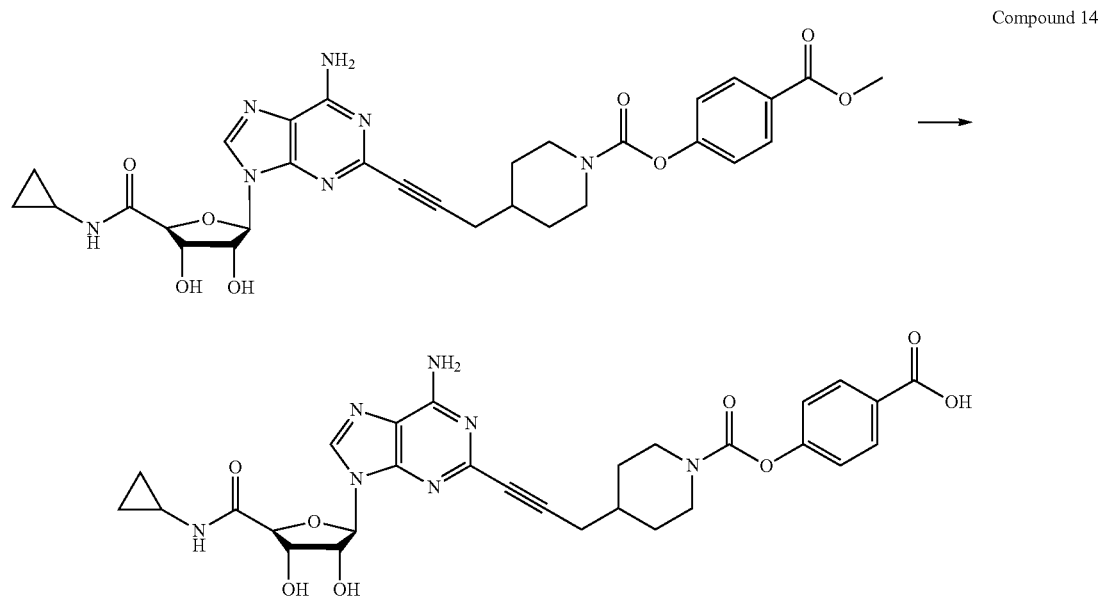

Compound 14

N-Cyclopropyl 2-{3-[1-(4-carboxyphenoxycarbonyl)-4-piperidinyl]-1-propyn-1-yl}adenosine-5'-uronamide. Batch: JR28-115. N-Cyclopropyl 2-{3-[1-(4-methoxycarbonylphe- 2.95 (2×bt, 4H), 2.74 (m, 1H), 2.49 (d, 4H), 1.98-1.44 (2×m, 5H), 0.87-0.56 (2×m, 4H). m/z MH$^+$=606.32. HPLC rt=10.4 min.

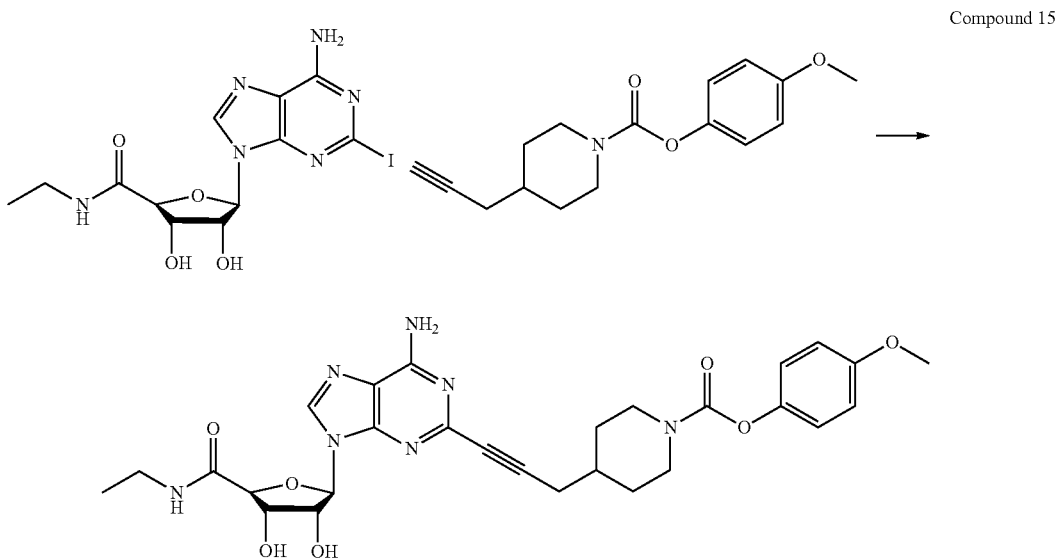

Compound 15

N-Ethyl 2-{3-[1-(4-methoxyphenoxycarbonyl)-4-piperidinyl]-1-propyn-1-yl}adenosine-5'-uronamide. Batch: AP26-28. 4-(methoxycarbonyl)phenyl 4-(prop-2-ynyl)piperidine-1-carboxylate, batch JR28-103 (0.250 mL, 0.4606 mmol) was added to a solution of N-Ethyl-2-iodoadenosine-5'-uronamide (0.200 g, 0.4606 mmol) according to general procedure 2. Yield=98.3 mg, 37%. m/z MH$^+$=580.25. HPLC rt=8.0 min.

N-Cyclopropyl 2-{3-[1-(4-chlorophenoxycarbonyl)-4-piperidinyl]-1-propyn-1-yl}adenosine-5'-uronamide. Batch: AP26-30. 4-(Chloro)phenyl 4-(prop-2-ynyl)piperidine-1-carboxylate, batch JR28-107 (0.150 mL, 0.2303 mmol) was added to a solution of N-Cyclopropyl-2-iodoadenosine-5'-uronamide (0.100 g, 0.2303 mmol) according to general procedure 2. Yield=70.4 mg, 53%. $^1$H NMR (CD$_3$OD) δ 8.41 (s, 2H), 7.37-7.08 (2×d, 4H), 6.02 (d, 1H), 4.82 (m, 1H), 4.42-4.12 (2×m, 4H), 3.11-2.92 (2×2 bt, 4H), 2.71 (m, 1H), 2.48-1.88 (d, 4H), 2.01-1.42 (2×m, 5H), 0.78-0.55 (2×m, 4H). m/z MH$^+$=596.27. HPLC rt=8.4 min.

Compound 16

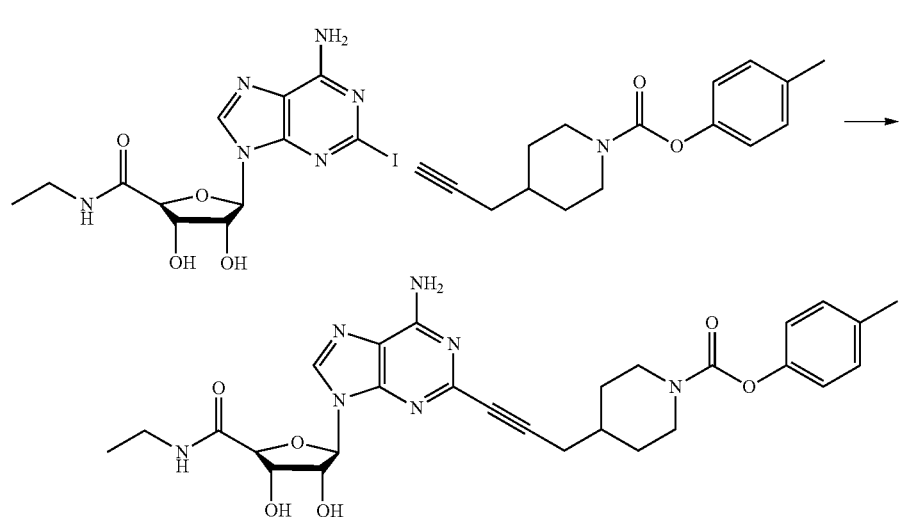

N-Ethyl 2-{3-[1-(4-methylphenoxycarbonyl)-4-piperidinyl]-1-propyn-1-yl}adenosine-5'-uronamide. Batch: AP26-29. 4-(methyl)phenyl 4-(prop-2-ynyl)piperidine-1-carboxylate, batch JR28-105 (0.150 mL, 0.2303 mmol) was added to a solution of N-Ethyl-2-iodoadenosine-5'-uronamide (0.100 g, 0.2303 mmol) according to general procedure 2. Yield=38.0 mg, 29%. $^1$H NMR (CD$_3$OD) δ 8.30 (s, 1H), 8.20 (s, 1H), 7.17-6.93 (2×d, 4H), 6.00 (d, 1H), 4.71 (m, 1H), 4.45-4.29 (m, 4H), 3.53-2.85 (2×2 m, 2×bt, 6H), 2.31 (d, 3H), 1.96-1.87 (m, 4H), 1.40 (3×m, 8H). m/z MH$^+$=564.26. HPLC rt=8.5 min.

Compound 17

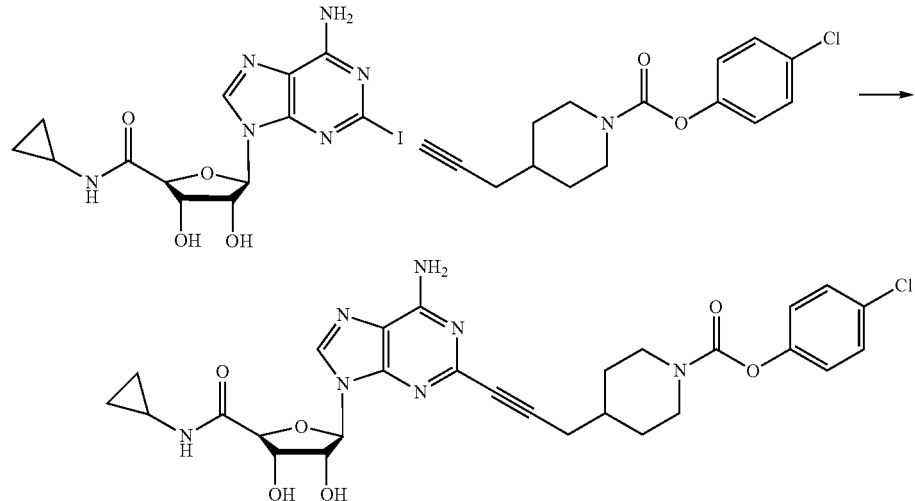

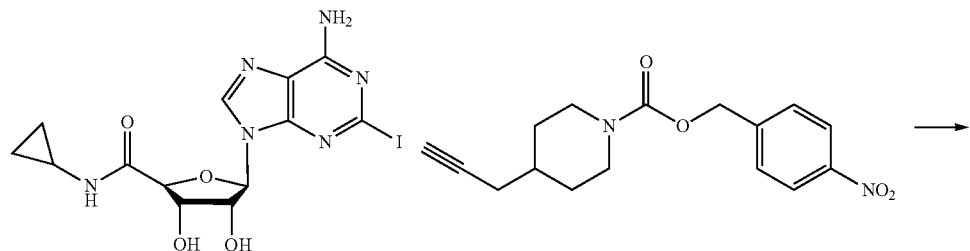

Compound 18

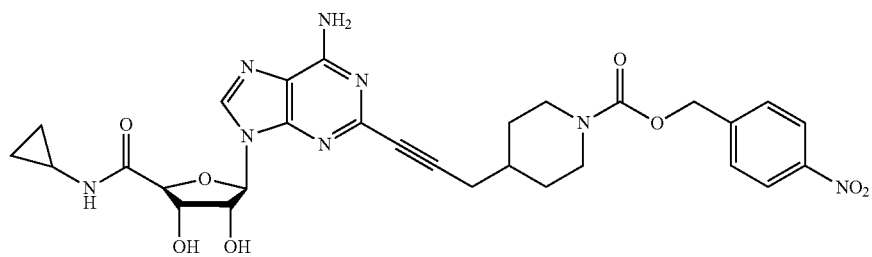

N-Cyclopropyl 2-{3-[1-(4-nitrobenzloxycarbonyl)-4-piperidinyl]-1-propyn-1-yl}adenosine-5'-uronamide. Batch: AP26-31. 4-(Nitro)benzyl-4-(prop-2-ynyl)piperidine-1-carboxylate, batch JR28-109 (0.150 mL, 0.2303 mmol) was added to a solution of N-Cyclopropyl-2-iodoadenosine-5'-uronamide (0.100 g, 0.2303 mmol) according to general procedure 2. Yield=42.8 mg, 31%. $^1$H NMR (CD$_3$OD) δ 8.40 (s, 1H), 8.22-7.56 (2×d, 4H), 8.16 (s, 1H), 6.02 (d, 1H), 5.23 (s, 2H), 4.81 (m, 1H), 4.40 (m, 2H), 3.29-2.85 (3×m, 6H), 2.70 (m, 1H), 1.91-1.19 (2×m, 5H), 0.77-0.53 (2×m, 4H). $^{13}$C (CD$_3$OD) δ 172.56, 156.04, 155.34, 147.84, 146.72, 144.81, 141.85, 128.05, 123.49, 89.20, 84.61, 73.30, 72.81, 65.71, 44.11, 35.38, 31.37, 25.47, 22.25, 5.80. m/z MH$^+$=621.26. HPLC rt=7.9 min.

N-Ethyl 2-{3-[1-(4-nitrophenyloxycarbonyl)-4-piperidinyl]-1-propyn-1-yl}adenosine-5'-uronamide. Batch: AP26-27. 4-(Nitro)phenyl-4-(prop-2-ynyl)piperidine-1-carboxylate, batch JR28-83 (0.250 mL, 0.4306 mmol) was added to a solution of N-Ethyl-2-iodoadenosine-5'-uronamide (0.200 g, 0.4606 mmol) according to general procedure 2. Yield=247.5 mg, 90%. NMR (CD$_3$OD) δ 8.30-7.34 (4×m, 6H), 6.00 (d, 1H), 4.83 (s, 1H), 4.31-4.20 (3×m, 4H), 3.12-2.96 (2×bt, 6H), 4.29 (d, 4H), 1.98-1.44 (2×m, 5H), 1.19 (s, 3H). m/z MH$^+$=595.25. HPLC rt=7.9 min.

Compound 19

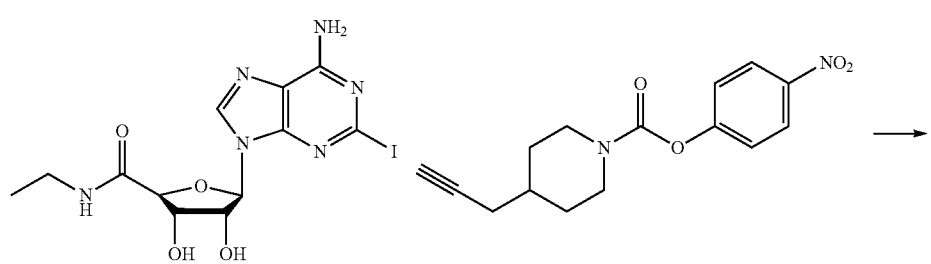

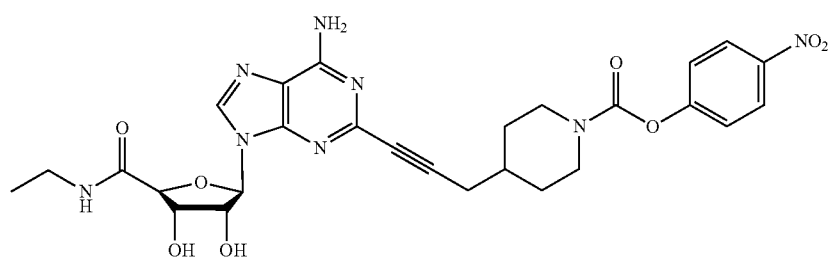

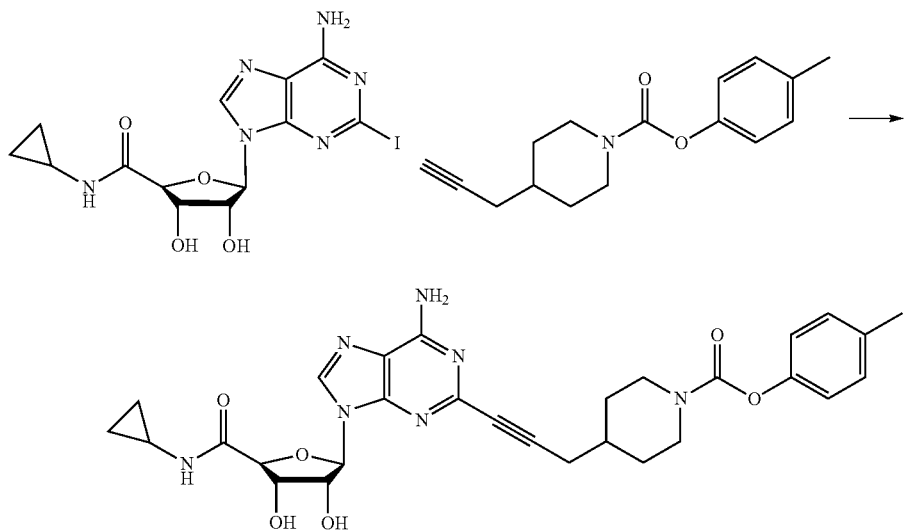

Compound 20

N-Cyclopropyl 2-{3-[1-(4-methylphenyloxycarbonyl)-4-piperidinyl]-1-propyn-1-yl}adenosine-5'-uronamide. Batch: AP26-43. 4-(Methyl)phenyl-4-(prop-2-ynyl)piperidine-1-carboxylate, batch JR28-105 (0.259 g, 1.006 mmol) was added to a solution of N-Cyclopropyl-2-iodoadenosine-5'-uronamide (0.109 g, 0.2443 mmol) according to general procedure 2. Yield=125.7 mg, 89%. NMR (CD$_3$OD) δ 8.40 (s, 2H), 7.17-6.93 (2×d, 4H), 6.02 (d, 1H), 4.80 (m, 1H), 4.38-4.21 (2×m, 4H), 3.05-2.91 (2×bt, 4H), 2.71 (m, 1H), 2.67 (s, 3H) 2.31 (s, 4H), 1.96-1.41 (2×m, 5H), 0.77-0.57 (2×m, 4H).). $^{13}$C(CD$_3$OD) δ 173.66, 157.18, 155.71, 150.61, 147.88, 143.01, 136.20, 130.73, 122.54, 90.34, 86.36, 85.75, 74.73, 73.89, 26.60, 23.38, 22.11, 20.78, 6.950, 4.575. m/z MH$^+$=576.35. HPLC rt=10.0 min.

N-Cyclopropyl 2-{3-[1-(2-methoxyphenyloxycarbonyl)-4-piperidinyl]-1-propyn-1-yl}adenosine-5'-uronamide. Batch: AP26-44. 2-(Methoxy)phenyl-4-(prop-2-ynyl)piperidine-1-carboxylate, batch AP26-39 (0.209 g, 0.7647 mmol) was added to a solution of N-Cyclopropyl-2-iodoadenosine-5'-uronamide (0.112 g, 0.2510 mmol) according to general procedure 2. Yield=94.5 mg, 64%. $^1$H NMR (CD$_3$OD) δ 8.41 (s, 1H), 8.00 (s, 1H), 7.20-6.89 (2×t, d, 4H), 6.03 (d, 1H), 4.80 (m, 1H), 3.79 (s, 3H), 3.34-2.85 (4×m, 8H), 2.70 (m, 1H), 2.49 (d, 4H), 1.96-1.30 (2×m, 5H), 0.78-0.55 (2×m, 4H). $^{13}$C(CD$_3$OD) δ173.71, 157.17, 155.53, 155.45, 153.13, 153.08, 143.05, 141.91, 127.63, 127.60, 124.06, 121.68, 113.68, 92.68, 113.69, 90.30, 86.41, 85.76, 74.76, 56.38, 36.57, 34.79, 32.51, 26.68, 23.39, 6.95. m/z MH$^+$=592.29. HPLC rt=9.2 min.

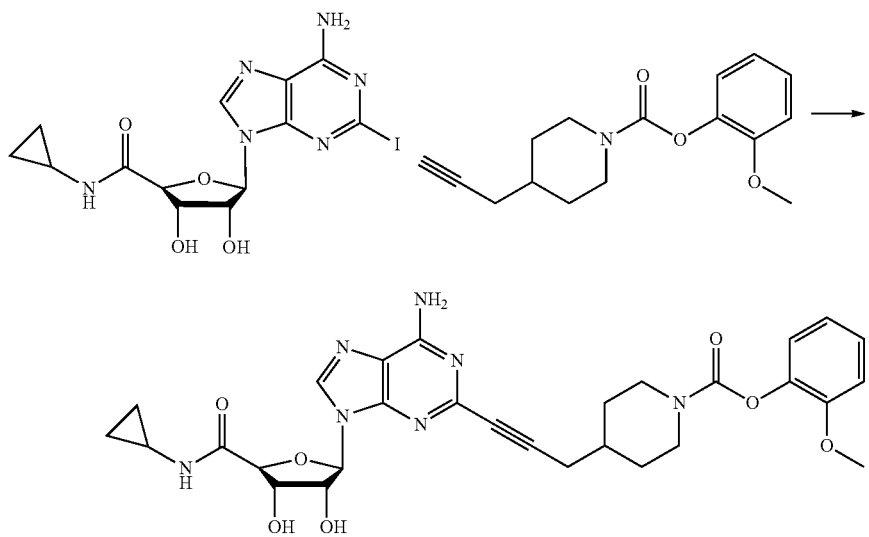

Compound 21

Compound 22

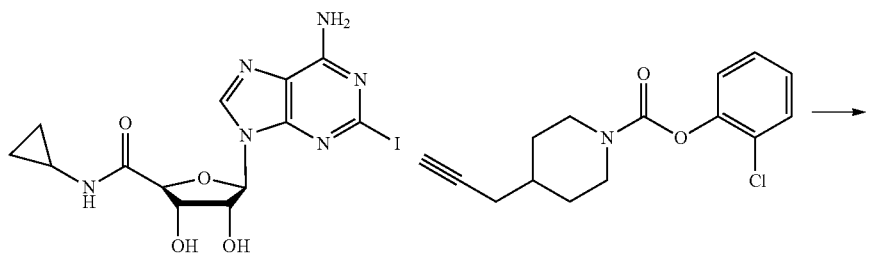

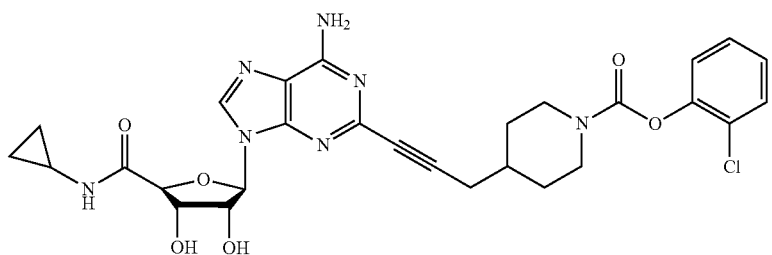

N-Cyclopropyl 2-{3-[1-(2-chlorophenyloxycarbonyl)-4-piperidinyl]-1-propyn-1-yl}adenosine-5'-uronamide. Batch: AP26-45. 2-(Chloro)phenyl-4-(prop-2-ynyl)piperidine-1-carboxylate, batch AP26-38 (0.303 g, 1.091 mmol) was added to a solution of N-Cyclopropyl-2-iodoadenosine-5'-uronamide (0.108 g, 0.2420 mmol) according to general procedure 2. Yield=45.8 mg, 32%. $^1$H NMR (CD$_3$OD) δ 8.43 (s, 2H), 7.46-7.19 (2×m, d, 4H), 6.03 (d, 1H), 4.83 (m, 1H), 4.39-4.20 (2×m, 4H), 3.29-2.98 (2×bt, 4H), 2.64 (m, 1H), 2.46 (d, 4H), 1.42-1.19 (2×m, 5H), 0.78-0.56 (2×m, 4H). m/z MH$^+$=596.29. HPLC rt=9.7 min.

N-Cyclopropyl 2-{3-[1-(4-methylphenyloxycarbonyl)-4-piperidinyl]-1-propyn-1-yl}adenosine-5'-uronamide. Batch: AP26-42. 4-(Methoxy)phenyl-4-(prop-2-ynyl)piperidine-1-carboxylate, batch JR28-103 (0.243 g, 0.8890 mmol) was added to a solution of N-Cyclopropyl-2-iodoadenosine-5'-uronamide (0.110 g, 0.2465 mmol) according to general procedure 2. Yield=27.8 mg, 19%. $^1$H NMR (CD$_3$OD) δ 7.97 (s, 2H), 7.00-6.85 (2×m, 4H), 6.03 (d, 1H), 4.83 (s, 1H), 4.41-4.21 (2×m, 4H), 3.76 (s, 3H), 3.12-2.85 (2×m, 4H), 2.70 (m, 1H), 2.48 (d, 4H), 1.99-1.24 (2×m, 5H), 0.77-57 (2×m, 4H). m/z MH$^+$=592.33. HPLC rt=9.5 min.

Compound 23

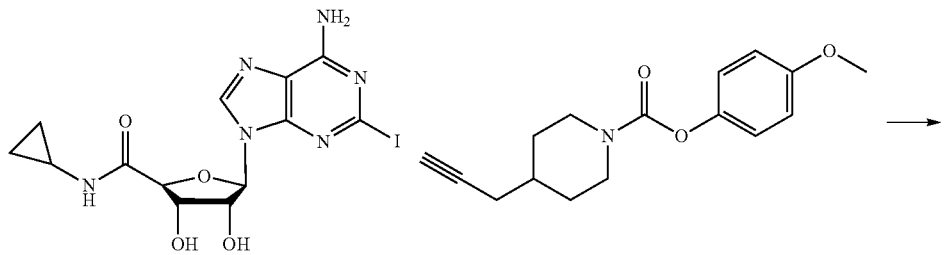

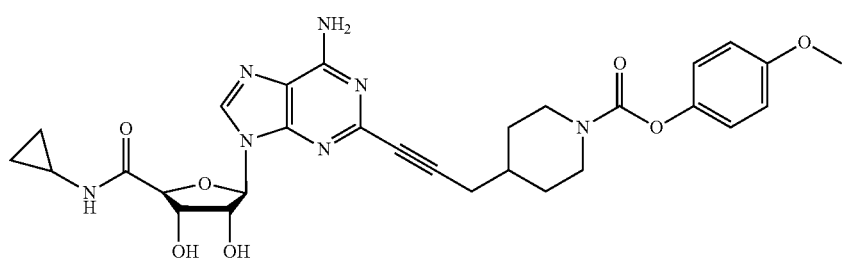

Compound 24

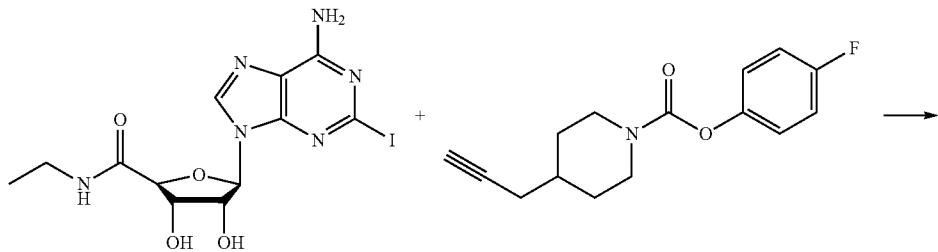

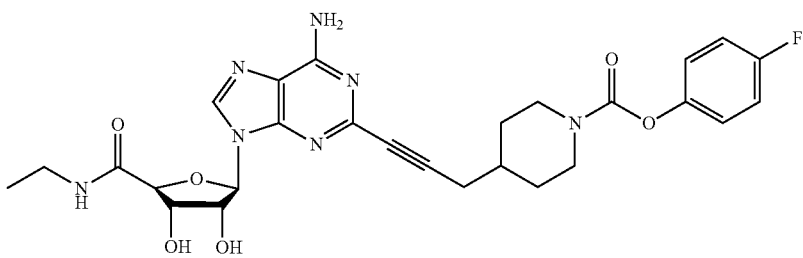

N-Ethyl 2-{3-[1-(4-fluorophenyloxycarbonyl)-4-piperidinyl]-1-propyn-1-yl}adenosine-5'-uronamide. Batch: AP26-47. 4-(Fluoro)phenyl-4-(prop-2-ynyl)piperidine-1-carboxylate, batch JR28-87 (0.291 g, 1.114 mmol) was added to a solution of N-Ethyl-2-iodoadenosine-5'-uronamide (0.119 g, 0.2741 mmol) according to general procedure 2. Yield=98.3 mg, 63%. $^1$H NMR (CD$_3$OD) δ 8.30 (s, 1H), 7.97 (s, 1H), 7.11-7.08 (2×m, 4H), 6.00 (d, 1H), 4.75 (s, 1H), 4.45-4.29 (2×m, 4H), 3.47 (m, 6H), 3.12-2.85 (3×m, 4H), 2.48 (d, 4H), 1.96-1.39 (2×m, 5H), 1.28 (t, 3H). m/z MH$^+$=568.15. HPLC rt=9.6 min.

N-Ethyl 2-{3-[1-(4-methoxycarboxyphenyloxycarbonyl)-4-piperidinyl]-1-propyn-1-yl}adenosine-5'-uronamide. Batch: AP26-48. 4-(methoxycarboxy)phenyl-4-(prop-2-ynyl)piperidine-1-carboxylate, batch JR28-85 (0.244 g, 0.8097 mmol) was added to a solution of N-Ethyl-2-iodoadenosine-5'-uronamide (0.109 g, 0.2510 mmol) according to general procedure 2. Yield=77.8 mg, 51%. $^1$H NMR (CD$_3$OD) δ 8.30 (s, 1H), 8.04-8.015 (d, 3H), 7.24-7.21 (d, 2H), 6.00 (d, 1H), 4.80 (m, 1H), 4.46-4.31 (2×m, 3H), 3.89 (s, 4H), 3.47 (m, 6H), 2.49 (d, 4H), 1.94-1.40 (2×m, 5H), 1.20 (t, 3H). $^{13}$C(CD$_3$OD) δ 178.79, 178.29, 172.11, 172.09, 156.74, 154.58, 143.41, 143.36, 131.94, 128.40, 125.07, 122.93, Compound 25

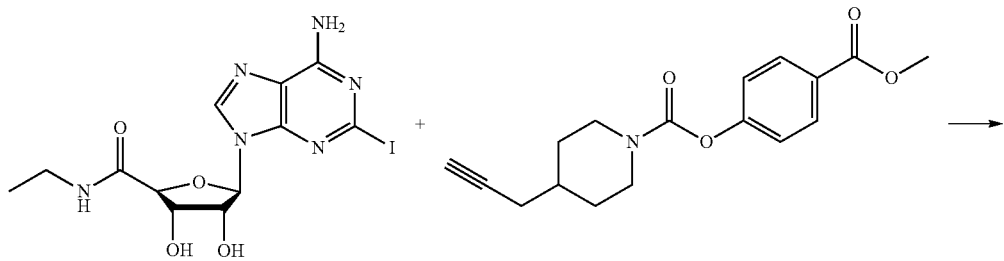

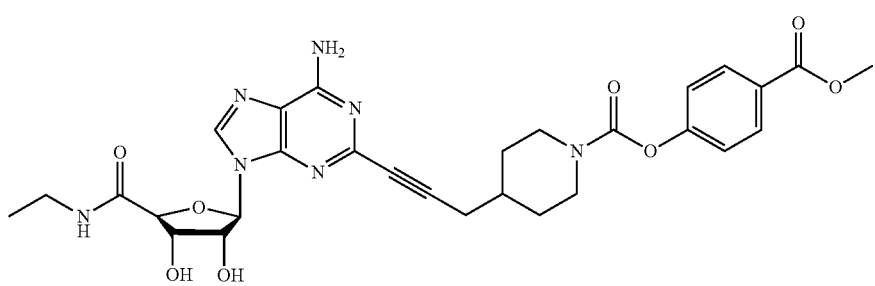

90.55, 88.76, 74.94, 74.62, 73.28, 68.27, 52.64, 45.81, 36.44, 35.18, 34.69, 26.49, 25.29, 15.30. m/z MH$^+$=608.15. HPLC rt=9.7 min.

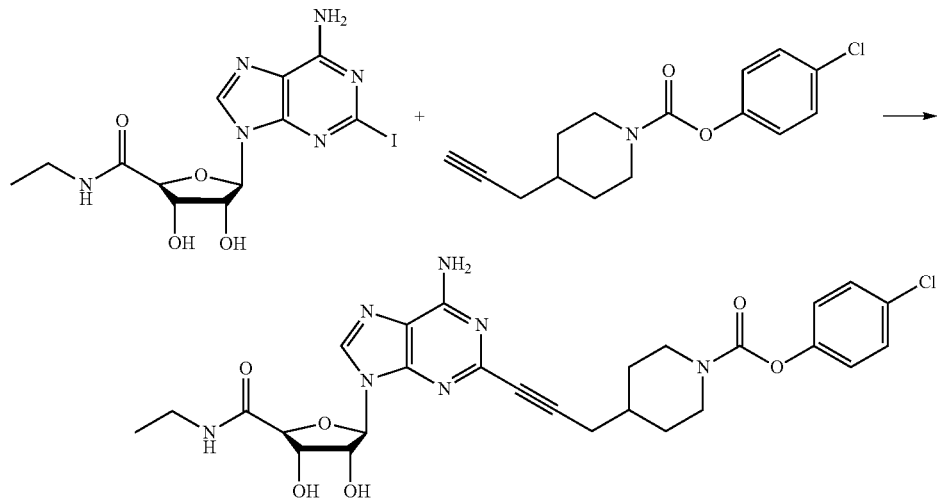

Compound 26

N-Ethyl 2-{3-[1-(4-chlorophenyloxycarbonyl)-4-piperidinyl]-1-propyn-1-yl}adenosine-5'-uronamide. Batch: AP26-49. 4-(chloro)phenyl-4-(prop-2-ynyl)piperidine-1-carboxylate, batch JR28-107 (0.281 g, 1.012 mmol) was added to a solution of N-Ethyl-2-iodoadenosine-5'-uronamide (0.116 g, 0.2672 mmol) according to general procedure 2. Yield=139.5 mg, 89%. $^1$H NMR (CD$_3$OD) δ 8.29 (s, 1H), 7.37-7.07 (2×m, 4H), 5.99 (d, 1H), 4.73 (m, 1H), 4.45 (s, 2H), 4.34-4.17 (2×m, 2H), 3.06-2.92 (2×bt, 6H), 2.47 (d, 4H), 1.96-1.37 (2×m, 5H), 1.19 (t, 3H). $^{13}$C(CD$_3$OD) δ 172.31, 157.31, 155.04, 151.528, 147.64, 143.39, 131.72, 130.30, 130.30, 124.51, 124.51, 120.73, 90.55, 86.41, 86.14, 82.93, 74.95, 73.28, 45.75, 45.38, 36.45, 35.19, 32.63, 32.63, 26.51, 15.33. m/z MH$^+$=584.17. HPLC rt=10.4 min.

Compound 27

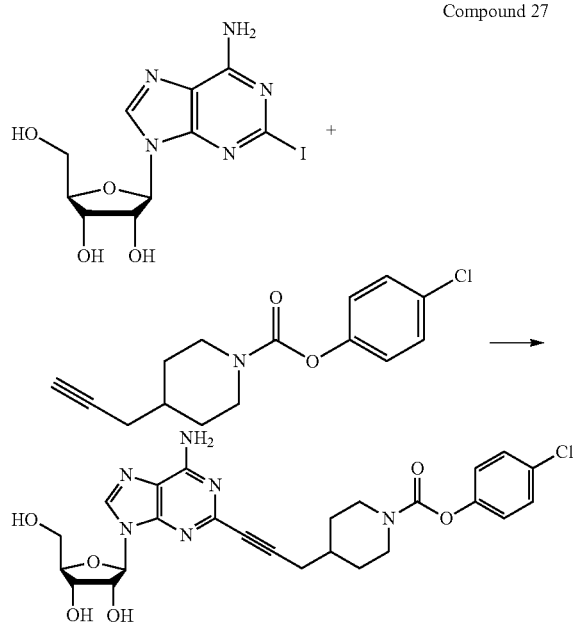

2-{3-[1-((4-Chloro)phenoxycarbanoyl)piperidin-4-yl]propyn-1-yl}adenosine. Batch: AB-10-015. 4-chlorophenyl 4-(prop-2-ynyl)piperidine-1-carboxylate, batch JR28-107 (0.624 g, 2.247 mmol) was added to a solution of 2-iodoadenosine (0.656 g, 1.669 mmol) according to general procedure 2. Yield: 0.445 g, 49%. NMR (CD$_3$OD) δ 8.30 (s, 1H), 7.37-7.07 (2×m, 4H), 5.93 (d, 1H), 4.71 (m, 2H), 4.31-4.17 (2×m, 3H), 3.91-3.75 (2×d, 2H), 3.07-2.93 (2×bt, 4H), 2.48 (d, 5H), 1.97-1.40 (2×m, 5H). m/z MH$^+$=543.09. HPLC rt=7.3 min.

Compound 28

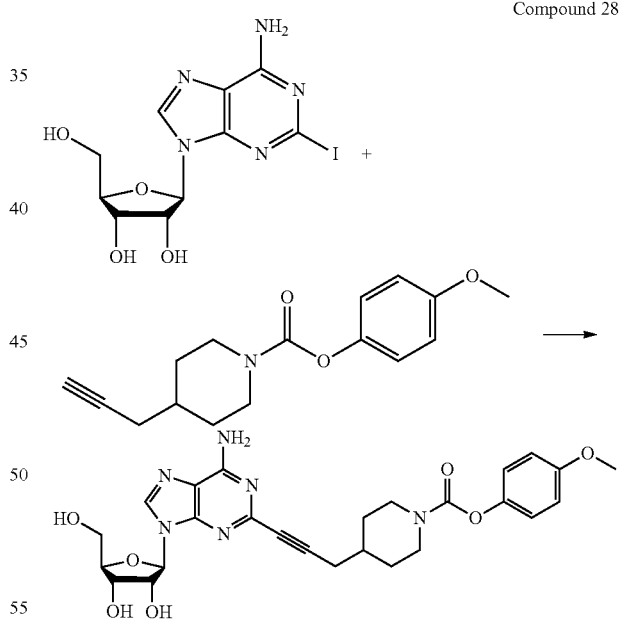

2-{3-[1-((4-Methoxy)phenoxycarbanoyl)piperidin-4-yl]propyn-1-yl}adenosine. Batch: AB-10-017. 4-methoxyphenyl 4-(prop-2-ynyl)piperidine-1-carboxylate, batch JR28-103 (597 g, 2.184 mmol) was added to a solution of 2-iodoadenosine (0.649 g, 1.651 mmol) according to general procedure 2. Yield: 0.294 g, 33%. $^1$H NMR (CD$_3$OD) δ 8.30 (s, 1H), 7.00-6.87 (2×m, 4H), 5.94 (d, 1H), 4.73 (m, 2H), 4.33-4.14 (2×m, 3H), 3.92-3.76 (2×d, 5H), 3.10-2.90 (2×bt, 4H), 2.46 (d, 5H), 1.91-1.40 (2×m, 5H). m/z MH$^+$=539.14. HPLC rt=5.5 min.

Compound 29

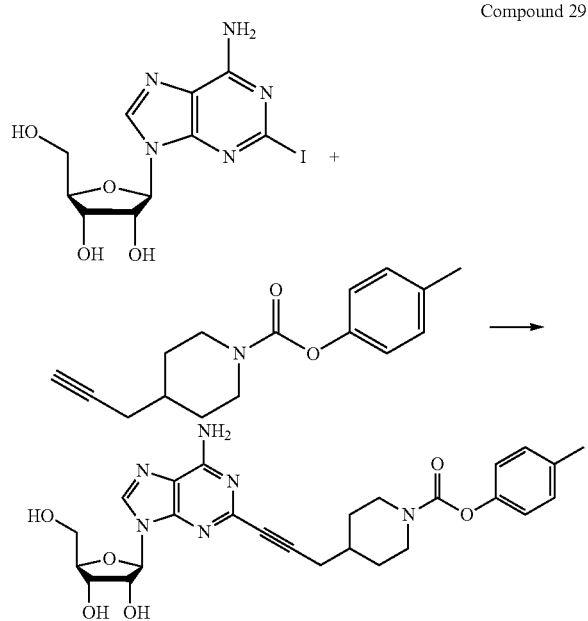

2-{3-[1-((4-Methyl)phenoxycarbanoyl)piperidin-4-yl]propyn-1-yl}adenosine. Batch: AB-10-019. 4-methylphenyl 4-(prop-2-ynyl)piperidine-1-carboxylate, batch JR28-105 (0.548 g, 2.130 mmol) was added to a solution of 2-iodoadenosine (0.629 g, 1.600 mmol) according to general procedure 2. Yield: 0.236 g, 28%. $^1$H NMR (CD$_3$OD) δ 8.29 (s, 1H), 7.14-6.92 (2×m, 4H), 5.95 (d, 1H), 4.75 (m, 2H), 4.34-4.16 (2×m, 3H), 3.91-3.71 (2×d, 2H), 3.10-2.90 (2×bt, 4H), 2.28 (s, 3H), 2.43 (d, 5H), 1.92-1.41 (2×m, 5H). m/z MH$^+$=523.16. HPLC rt=6.8 min.

Compound 30

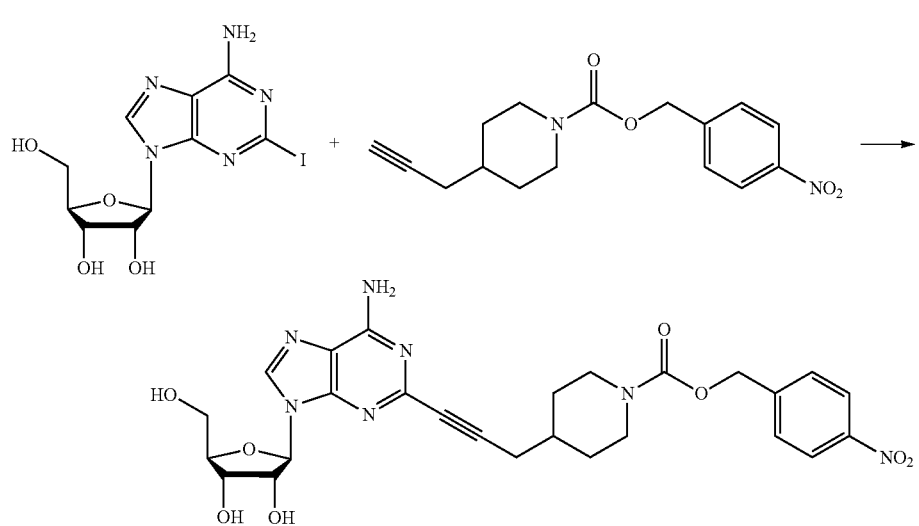

2-{3-[1-((4-Nitro)benzyloxycarbanoyl)piperidin-4-yl]propyn-1-yl}adenosine. Batch: AB-10-021. 4-nitrobenzyl 4-(prop-2-ynyl)piperidine-1-carboxylate, batch JR28-109 (0.743 g, 2.458 mmol) was added to a solution of 2-iodoadenosine (0.658 g, 1.674 mmol) according to general procedure 2. Yield: 0.694 g, 42%. $^1$H NMR (CD$_3$OD) δ 8.29 (s, 1H), 8.18-7.56 (2×d, 4H), 5.94 (d, 1H), 5.23 (s, 2H), 4.69 (m, 2H), 4.31-4.14 (2×m, 3H), 3.84-3.74 (2×d, 2H), 3.10-2.90 (bs, 4H), 2.44 (d, 5H), 1.91-1.40 (2×m, 5H). m/z MH$^+$=568.10. HPLC rt=5.8 min.

Compound 31

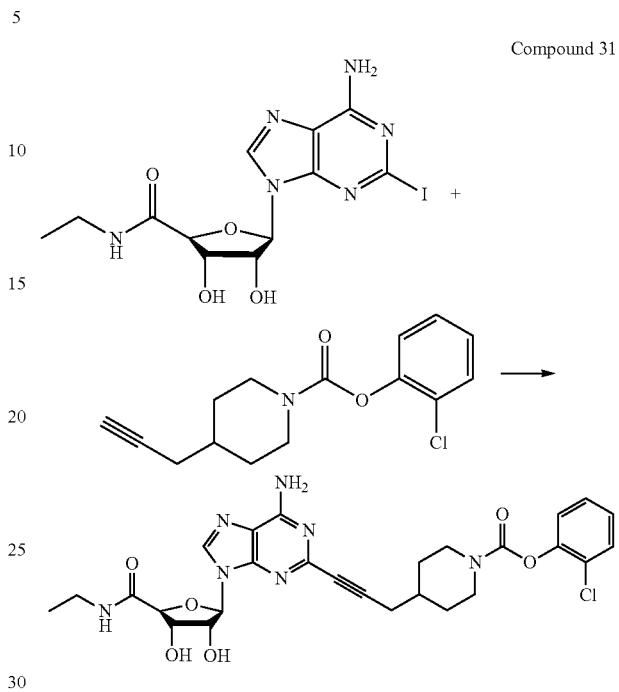

N-Ethyl 2-{3-[1-(2-chlorophenyloxycarbonyl)-4-piperidinyl]-1-propyn-1-yl}adenosine-5'-uronamide. Batch: AP26-57. 2-(chloro)phenyl-4-(prop-2-ynyl)piperidine-1-carboxylate, batch AP26-38 (0.296 g, 1.066 mmol) was added to a solution of N-Ethyl-2-iodoadenosine-5'-uronamide (0.127 g, 0.2925 mmol) according to general procedure 2. $^1$H NMR (CD$_3$OD) δ 9.10 (s, 1H), 8.30 (s, 1H), 7.46-7.20 (3×m, 5H), 6.00 (d, 1H), 4.74 (m, 1H), 4.47-4.18 (3×m, 4H), 3.48 (m, 1H), 3.99-2.97 (2×bt, 5H), 2.94 (d, 4H), 1.98-1.41 (2×m, 5H), 1.23 (t, 3H). m/z MH$^+$=584.17. HPLC rt=10.0 min.

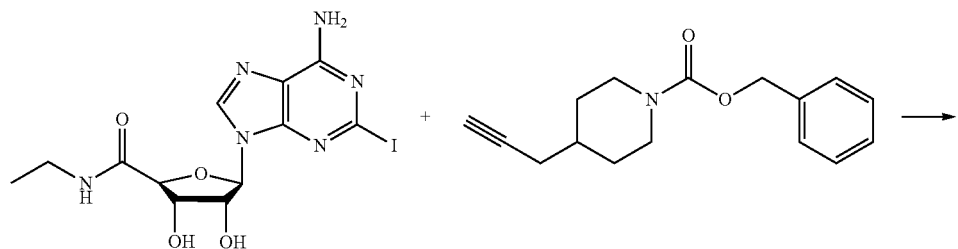

Compound 32

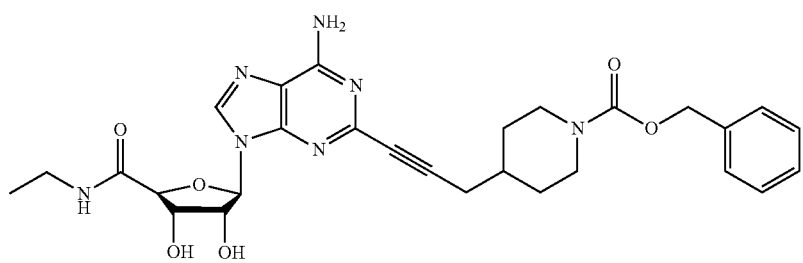

N-Ethyl 2{-[1-(benzyloxycarbonyl)-4-piperidinyl]-1-propyn-1-yl}adenosine-5'-uronamide. Batch: AP26-58. Benzyl 4-(prop-2-ynyl)piperidine-1-carboxylate, batch JR28-13 (0.236 g, 0.6643 mmol) was added to a solution of N-Ethyl-2-iodoadenosine-5'-uronamide (0.124 g, 0.2856 mmol) according to general procedure 2. m/z MH+=564.18. HPLC rt=10.1 min.

59. 4-(nitro)benzyl 4-(prop-2-ynyl)piperidine-1-carboxylate, batch JR28-107 (0.281 g, 1.012 mmol) was added to a solution of N-Ethyl-2-iodoadenosine-5'-uronamide (0.116 g, 0.2672 mmol) according to general procedure 2. $^1$H NMR (CD$_3$OD) δ 8.30 (s, 1H), 8.22 (d, 3H), 7.59 (d, 2H), 5.99 (d, 1H), 5.23 (s, 2H), 4.71 (m, 1H), 4.45 (m, 2H), 4.30 (2×m, 2H),

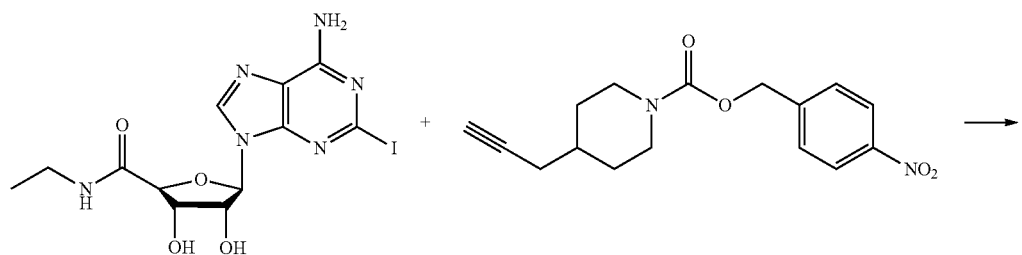

Compound 33

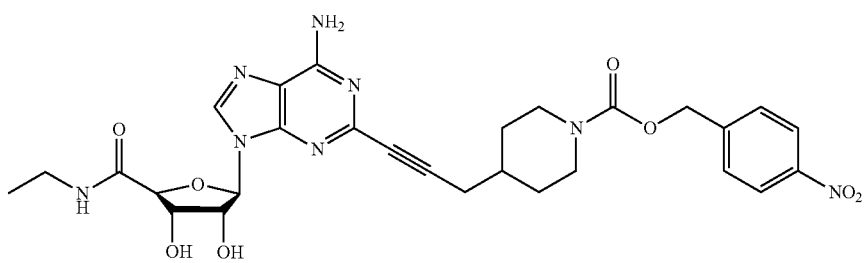

N-Ethyl 2-{3-[1-(4-nitrobenzyloxycarbonyl)-4-piperidinyl]-1-propyn-1-yl}adenosine-5'-uronamide. Batch: AP26-

3.47 (m, 2H), 3.31-2.89 (2×m, 4H), 2.44 (d, 4H), 1.92-1.23 (2×d, 5H), 1.17 (t, 3H). m/z MH+=609.20. HPLC rt=9.8 min.

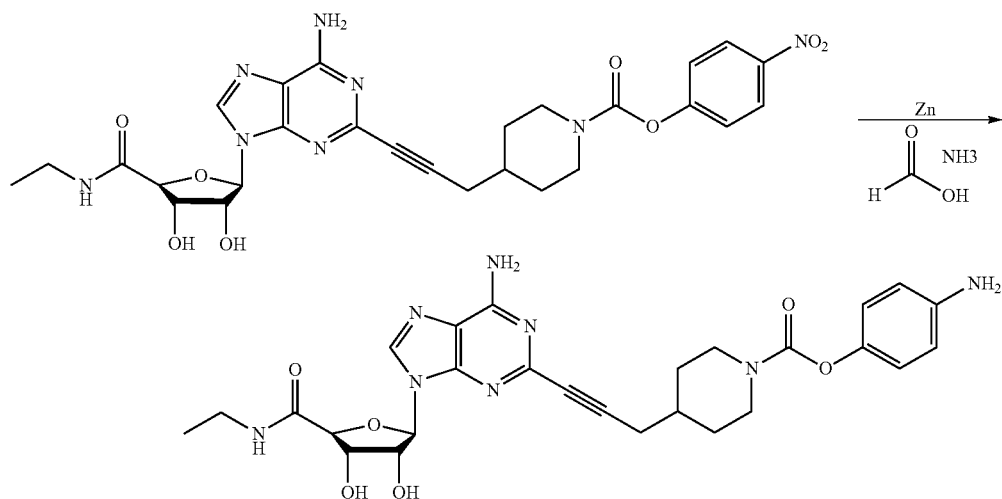

Compound 34

N-Ethyl 2-{3-[1-(4-aminophenoxycarbonyl)-4-piperidinyl]-1-propyn-1-yl}adenosine-5'-uronamide. Batch: AP26-35. N-Ethyl 2-{3-[1-(4-nitrophenyloxycarbonyl)-4-piperidinyl]-1-propyn-1-yl}adenosine-5'-uronamide, batch AP26-27 (0.00960 g, 0.0161 mmol) was added to a solution of Zn dust (0.0250 g, 0.3823 mmol) in 2 mL of ammonium formate. The mixture was then stirred at 50° C. for 3 h, evaporated down, and purified according to general procedure 2. m/z MH+=565.12. HPLC rt=5.8 min.

Compound 35

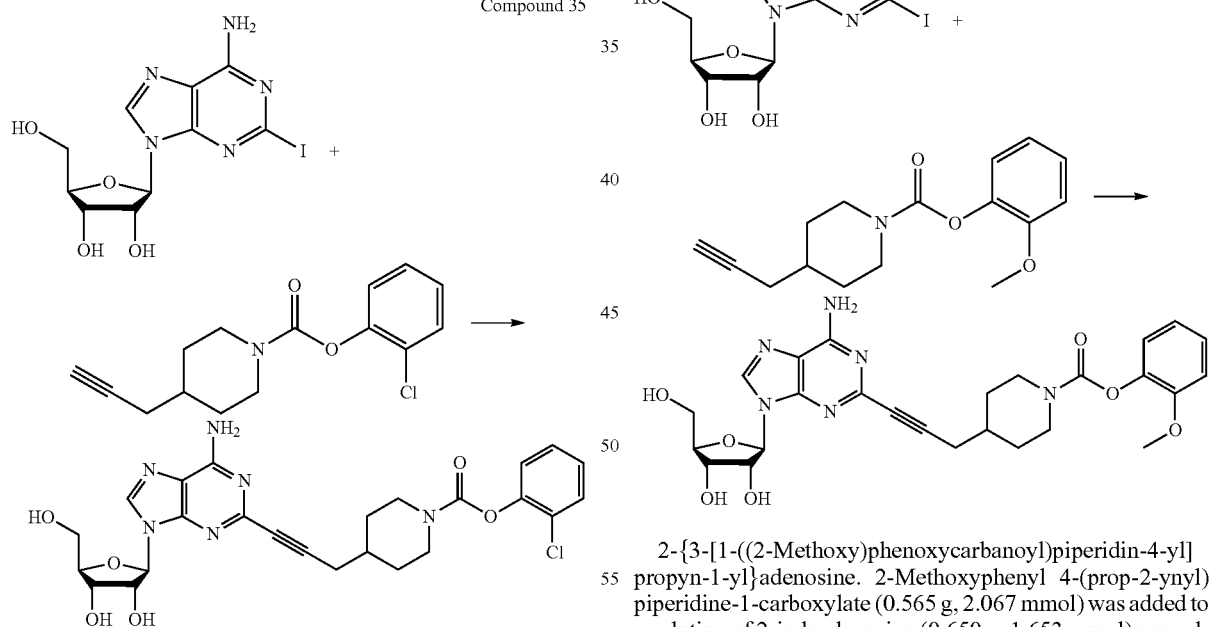

2-{3-[1-((2-Chloro)phenoxycarbanoyl)piperidin-4-yl]propyn-1-yl}adenosine. 2-Chlorophenyl 4-(prop-2-ynyl)piperidine-1-carboxylate (0.588 g, 2.117 mmol) was added to a solution of 2-iodoadenosine (0.602 g, 1.531 mmol) according to general procedure 2: yield 733 mg, 88%. $^1$H NMR (CD$_3$OD) δ 8.30 (s, 1H), 7.45-7.40, 7.33-7.26, 7.22-7.16 (3×m, 4H), 5.95 (d, 1H, J=6.3 Hz), 4.74 (t, 1H), 4.41-4.30 (m, 2H), 4.20-4.11 (m, 2H), 3.94-3.86, 3.78-3.71, (2×m, 2H), 3.08, 2.92 (2×br t, 2H), 2.43 (d, 2H, J=6.2 Hz), 2.01-1.78, 1.54-1.28 (2×m, 5H). $^{13}$C NMR (CD$_3$OD) δ 157.2, 154.3, 150.1, 148.9, 147.4, 142.6, 131.1, 129.0, 128.3, 127.9, 125.4, 120.4, 91.3, 88.2, 86.7, 82.2, 75.5, 72.6, 64.7, 63.5, 45.8, 36.4, 32.4, 26.5, 25.2. LRMS ESI (M+H+) 543.1. HPLC rt=6.2 min.

Compound 36

2-{3-[1-((2-Methoxy)phenoxycarbanoyl)piperidin-4-yl]propyn-1-yl}adenosine. 2-Methoxyphenyl 4-(prop-2-ynyl)piperidine-1-carboxylate (0.565 g, 2.067 mmol) was added to a solution of 2-iodoadenosine (0.650 g, 1.653 mmol) according to general procedure 2: yield 775 mg, 87%. $^1$H NMR (CD$_3$OD) δ 8.30 (s, 1H), 7.24-7.17, 7.09-7.04, 6.97-6.91 (3×m, 4H), 5.96 (d, 1H, J=6.5 Hz), 4.74 (dd, 1H, J=5.1, J=6.4 Hz), 4.43-4.32 (m, 2H), 4.25-4.16 (m, 2H), 3.96-3.89, 3.82 (s, 3H), 3.80-3.74, (2×m, 2H), 3.07, 2.92 (2×br t, 2H), 2.51 (d, 2H, J=6.0 Hz), 2.03-1.85, 1.60-1.35 (2×m, 5H). $^{13}$C NMR (CD$_3$OD) δ 157.3, 155.5, 153.1, 150.2, 147.5, 142.6, 141.9, 127.6, 124.1, 121.7, 120.4, 113.7, 91.3, 88.3, 86.7, 82.2, 75.5, 72.6, 64.7, 63.5, 56.4, 45.8, 36.6, 32.5, 26.5, 25.2. LRMS ESI (M+H+) 539.1. HPLC rt=5.1 min.

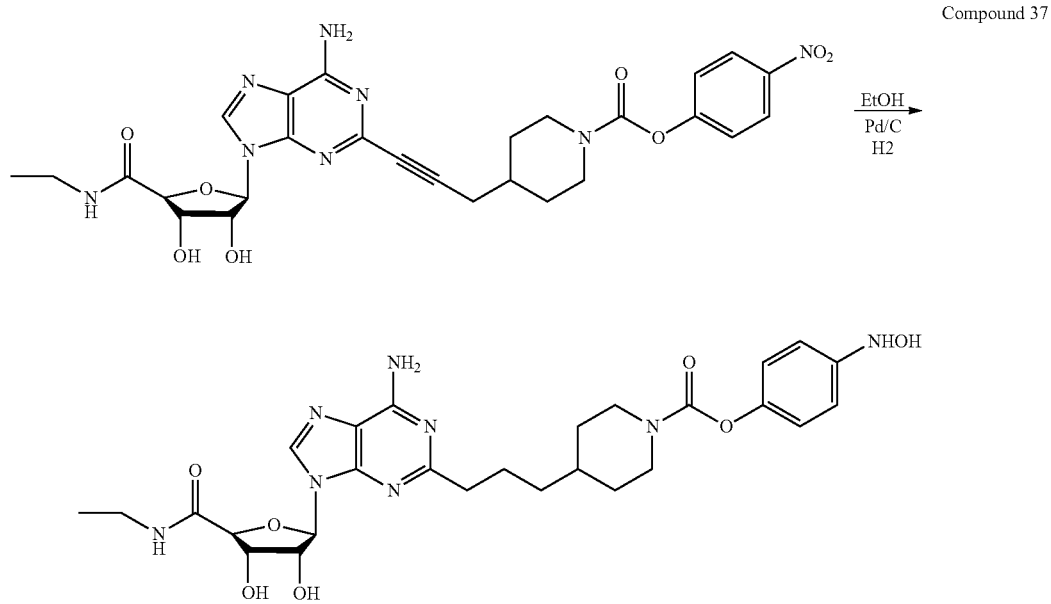

Compound 37

N-Ethyl 2-[3-[1-(4-hydroxyamino)phenyl 4-propylpiperidine]}1-1-carboxylate]adenosine-5'-uronamide. Batch: AP26-53. N-Ethyl 2-{3-[1-(4-nitrophenoxycarbonyl)-4-piperidinyl]-1-propyn-1-yl}adenosine-5'-uronamide, batch AP26-27 (0.010 g, 0.0168 mmol) was added to a solution of Pd/C (0.0250 g, 0.3823 mmol) in 3 mL of ethanol. The mixture was then stirred at 12 h under $H_2$, filtered, and purified according to general procedure 2. m/z $MH^+$=584.16. HPLC rt=10.4 min N-Cyclopropyl 2-[3-[1-(phenoxycarbonyl) 4-propylpiperidine]}-1-carboxylate]adenosine-5'-uronamide. Batch: AP26-67. N-Cyclopropyl 2-{3-[1-(4-chlorophenoxycarbonyl)-4-piperidinyl]-1-propyn-1-yl}adenosine-5'-uronamide, ATL370, batch AP26-30 (0.0056 g, 0.00940 mmol) was added to a solution of Pd/C (catalytic) in 3 mL of ethanol. The mixture was then stirred at 12 h under $H_2$, filtered, and purified according to general procedure 2. m/z $MH^+$=566.25. HPLC rt=8.4 min.

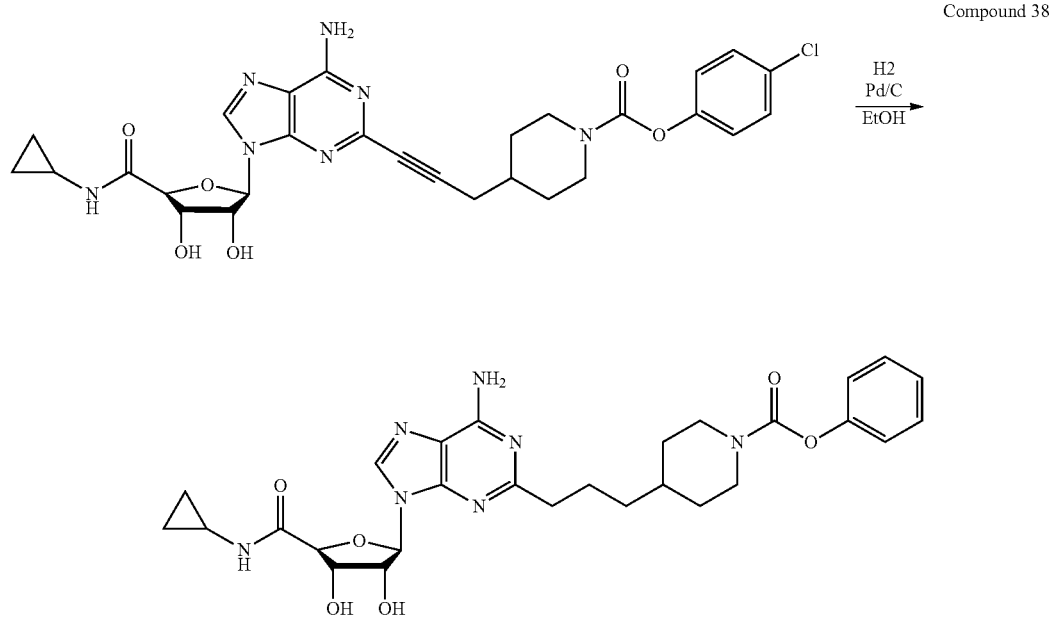

Compound 38

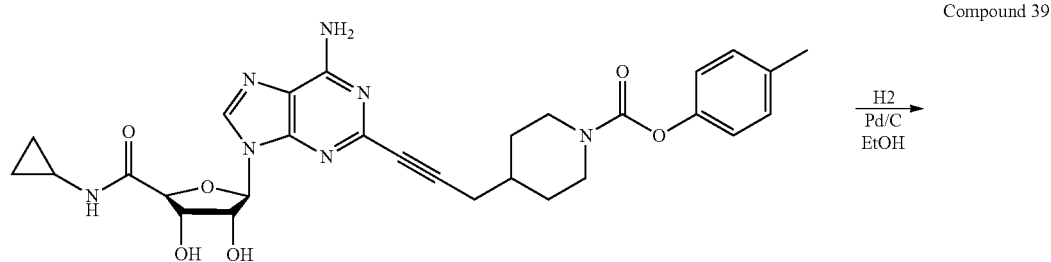

Compound 39

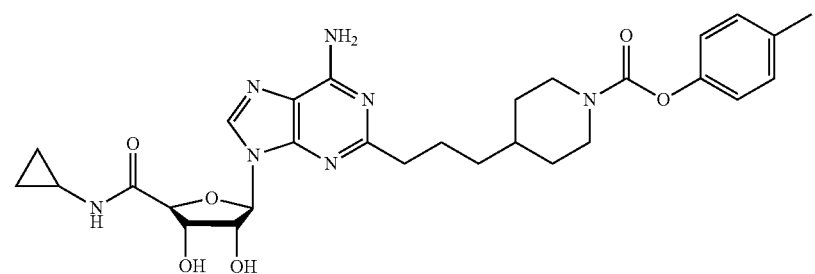

N-Cyclopropyl 2-[3-[1-(4-methylphenoxycarbonyl) 4-propylpiperidine]}-1-carboxylate]adenosine-5'-uronamide. Batch: AP26-66. N-Cyclopropyl 2-{3-[1-4-methylphenoxycarbonyl)-4-piperidinyl]-1-propyn-1-yl}adenosine-5'-uronamide, ATL376, batch AP26-43 (0.0072 g, 0.0125 mmol) was added to a solution of Pd/C (catalytic) in 3 mL of ethanol. The mixture was then stirred at 12 h under $H_2$, filtered, and purified according to general procedure 2. m/z $MH^+$=580.25. HPLC rt=9.3 min N-Cyclopropyl 2-[3-[1-(4-nitrophenoxycarbonyl) 4-propylpiperidine]}-1-carboxylate]adenosine-5'-uronamide. Batch: AP26-71. N-Cyclopropyl 2-{3-[1-4-aminophenoxycarbonyl)-4-piperidinyl]-1-propyn-1-yl}adenosine-5'-uronamide, ATL361, batch JR28-93 (0.0052 g, 0.00857 mmol) was added to a solution of Pd/C (catalytic) in 3 mL of ethanol. The mixture was then stirred at 12 h under $H_2$, filtered, and purified according to general procedure 2. m/z $MH^+$=577.19. HPLC rt=5.6 min.

Compound 40

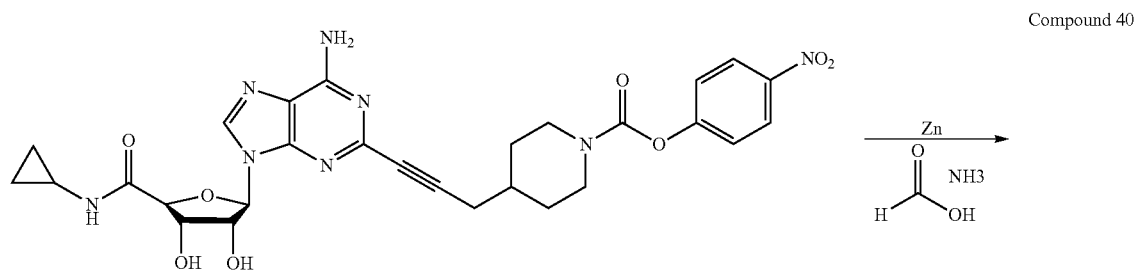

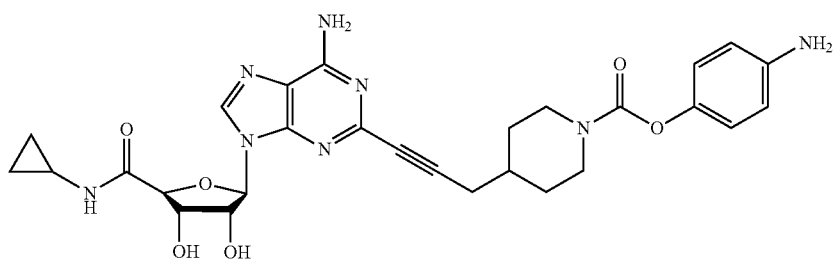

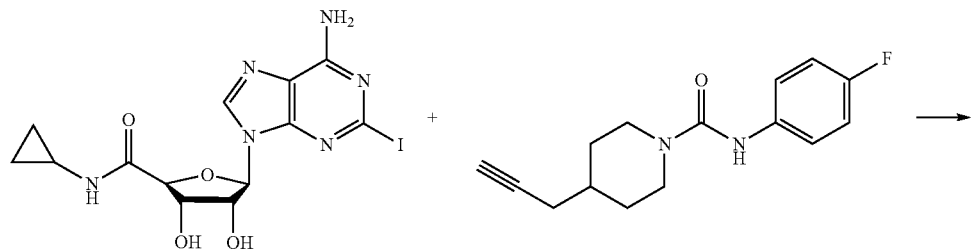

Compound 41

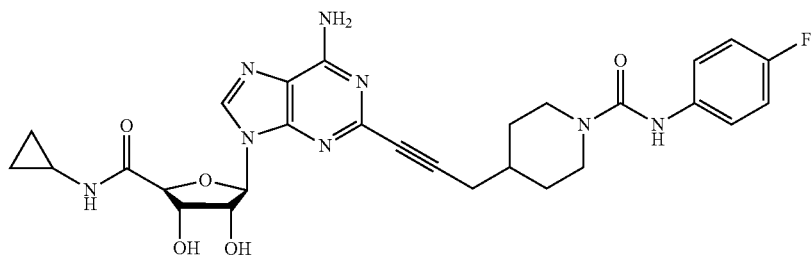

N-Cyclopropyl 2-{3-[1-(4-fluorophenyloxycarboxymidyl)-4-piperidinyl]-1-propyn-1-yl}adenosine-5'-uronamide. Batch: AP26-72. 4-Fluorophenyl 4-(prop-2-ynyl)piperidine-1-urea, batch AP26-64 (0.287 g, 1.103 mmol) was added to a solution of N-Cyclopropyl-2-iodoadenosine-5'-uronamide (0.076 g, 0.1703 mmol) according to general procedure 2. Yield=58.6 mg, 60%. $^1$H NMR (CD$_3$OD) δ 8.40 (s, 1H), 8.02 (s, 1H), 7.88-6.98 (2×m, 4H), 6.02 (d, 2H), 4.41 (m, 1H), 4.22-2.69 (4×m, 9H), 2.46 (2, 1H), 2.18 (m, 4H), 1.95-1.25 (2×m, 5H), 0.77-0.57 (2×m, 4H). m/z MH$^+$=579.19. HPLC rt=8.4 min.

N-Cyclopropyl 2-{3-[1-(4-chlorophenyloxycarboxymidyl)-4-piperidinyl]-1-propyn-1-yl}adenosine-5'-uronamide. Batch: AP26-73. 4-Chlorophenyl 4-(prop-2-ynyl)piperidine-1-urea, batch AP26-63 (0.304 g, 1.098 mmol) was added to a solution of N-Cyclopropyl-2-iodoadenosine-5'-uronamide (0.074 g, 0.1658 mmol) according to general procedure 2. Yield=25.2 mg, 26%. $^1$H NMR (CD$_3$OD) δ 8.70 (s, 1H), 8.40 (s, 1H), 7.35-7.24 (2×d, 4H), 6.01 (d, 2H), 4.47 (m, 1H), 4.18-2.71 (4×m, 8H), 2.47 (d, 1H), 1.96-1.28 (2×m, 5H), 0.77-0.55 (2×m, 4H). m/z MH$^+$=595.16. HPLC rt=9.4 min.

Compound 42

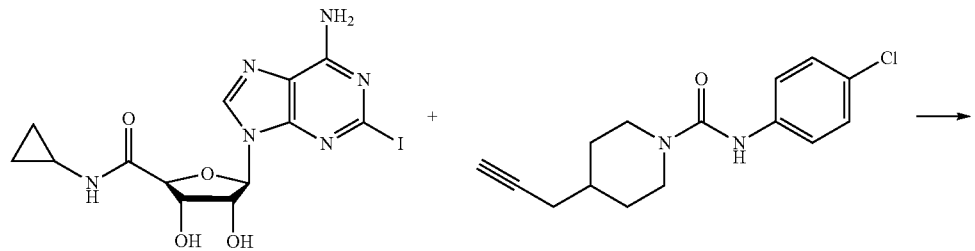

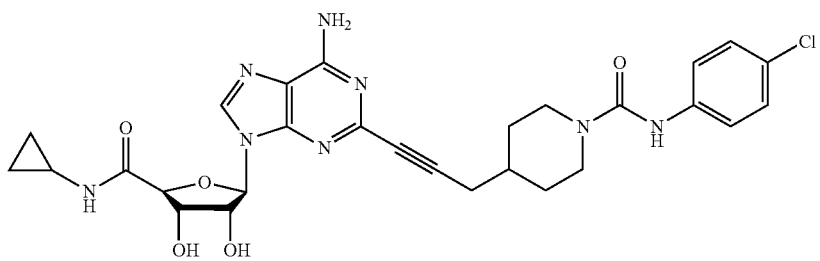

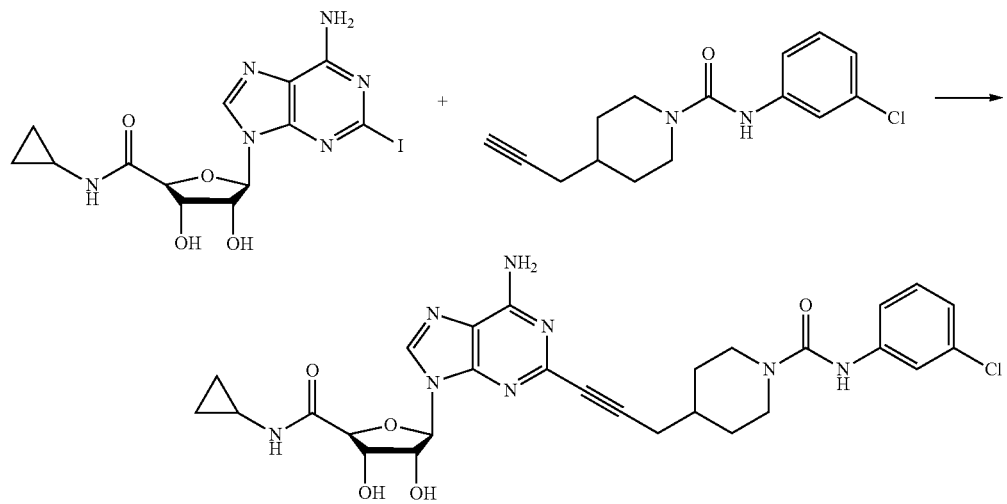

Compound 43

N-Cyclopropyl 2-{3-[1-(3-chlorophenyloxycarboxymidyl)-4-piperidinyl]-1-propyn-1-yl}adenosine-5'-uronamide. Batch: AP26-74. 3-Chlorophenyl 4-(prop-2-ynyl)piperidine-1-carboxylate, batch AP26-62 (0.305 g, 1.102 mmol) was added to a solution of N-Cyclopropyl-2-iodoadenosine-5'-uronamide (0.085 g, 0.1905 mmol) according to general procedure 2. Yield=25.5 mg, 23%. ¹H NMR (CD₃OD) δ 8.40 (s, 1H), 8.0 (s, 1H), 7.65-7.21 (2×m, 4H), 6.04 (d, 2H), 4.23 (s, 1H), 3.74-2.96 (4×m, 8H), 2.71 (m, 1H), 2.46 (d, 4H), 1.96-1.29 (2×m, 5H), 0.78-0.56 (2×m, 4H). m/z MH⁺=595.15. HPLC rt=9.4 min.

Compound 44

2-{3-[1-(4-Fluorophenoxycarbamidyl)piperidin-4-yl]propyn-1-yl}adenosine. N-(4-fluorophenyl)-4-(prop-2-ynyl)piperidine-1-carboxamide (1.122 g, 4.31 mmol) was added to a solution of 2-iodoadenosine (0.571 g, 1.452 mmol) according to general procedure 2: yield 14 mg, 2%. ¹H NMR (CD₃OD) δ 8.35 (s, 1H), 7.35-7.27 (m, 2H), 7.03-6.93 (m, 2H), 5.93 (d, 1H, J=6.3 Hz), 4.72 (br t, 1H), 4.34-4.29 (m, 1H), 4.23-4.13 (m, 3H), 3.89 (dd, 1H, J=2.1 Hz, J=12.6 Hz), 3.73 (dd, 1H, J=2.3, J=12.6 Hz), 2.88 (t, 2H), 2.42 (d, 2H, J=6.2 Hz), 1.97-1.74, 1.44-1.25 (2×m, 5H). LRMS ESI (M+H⁺) 526.1. HPLC rt=6.8 min.

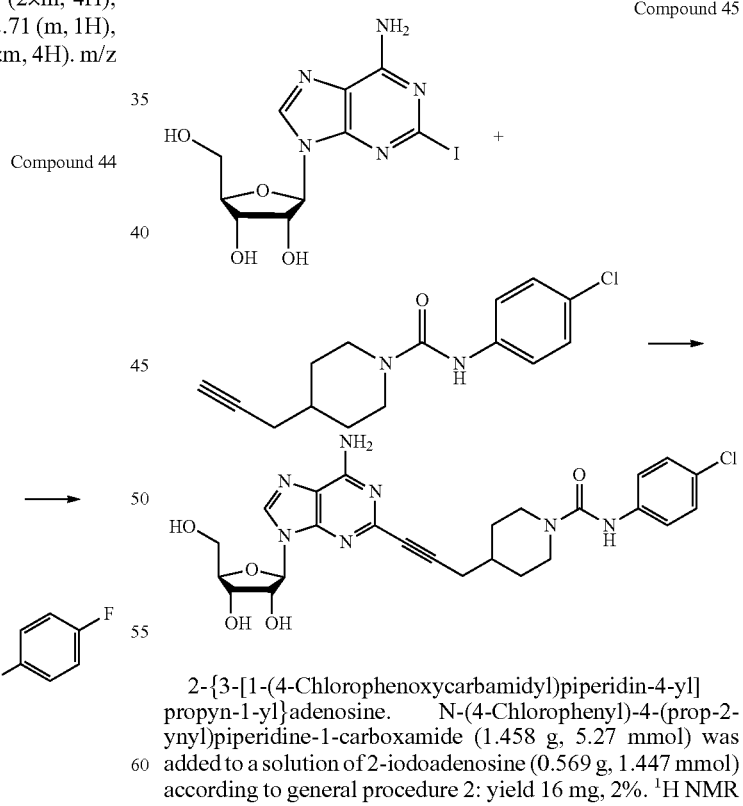

Compound 45

2-{3-[1-(4-Chlorophenoxycarbamidyl)piperidin-4-yl]propyn-1-yl}adenosine. N-(4-Chlorophenyl)-4-(prop-2-ynyl)piperidine-1-carboxamide (1.458 g, 5.27 mmol) was added to a solution of 2-iodoadenosine (0.569 g, 1.447 mmol) according to general procedure 2: yield 16 mg, 2%. ¹H NMR (CD₃OD) δ 8.35 (s, 1H), 7.34 (d, 2H, J=9.1 Hz), 7.22 (d, 2H, J=9.1 Hz), 5.93 (d, 1H, J=6.5 Hz), 4.71 (t, 1H), 4.33-4.28 (m, 1H), 4.24-4.13 (m, 3H), 3.89 (dd, 1H, J=2.3 Hz, J=12.6 Hz), 3.73 (dd, 1H, J=2.5, J=12.7 Hz), 2.90 (t, 2H), 2.44 (d, 2H, J=6.2 Hz), 1.99-1.78, 1.46-1.26 (2×m, 5H). HPLC rt=9.4 min.

81

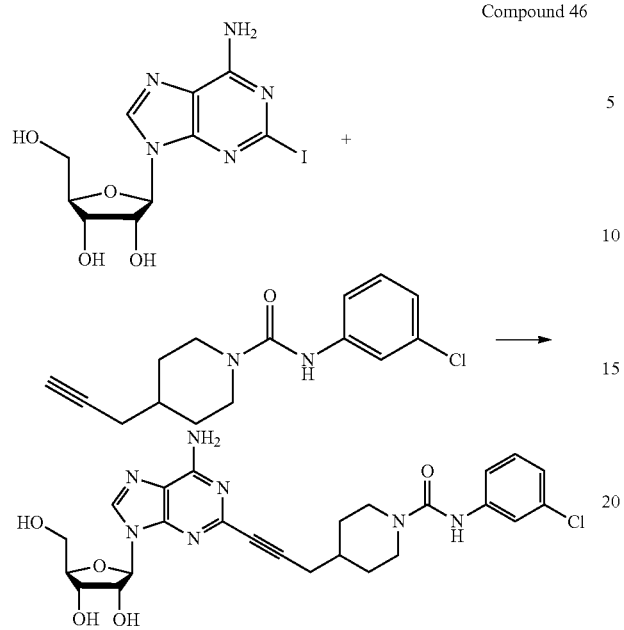

Compound 46

82

2-{3-[1-(3-Chlorophenoxycarbamidyl)piperidin-4-yl]propyn-1-yl}adenosine. N-(3-Chlorophenyl)-4-(prop-2-ynyl)piperidine-1-carboxamide (1.603 g, 5.79 mmol) was added to a solution of 2-iodoadenosine (0.640 g, 1.628 mmol) according to general procedure 2: yield 344 mg, 39%. $^1$H NMR (CD$_3$OD) δ 8.30 (s, 1H), 7.49 (t, 1H, J=1.9 Hz), 7.28-7.15 (m, 2H), 6.98-6.93 (m, 1H), 5.93 (d, 1H, J=6.3 Hz), 4.72 (t, 1H), 4.33-4.29 (m, 1H), 4.24-4.14 (m, 3H), 3.89 (dd, 1H, J=2.2 Hz, J=12.6 Hz), 3.73 (dd, 1H, J=2.5, J=12.7 Hz), 2.88 (t, 2H, J=12.5 Hz), 2.42 (d, 2H, J=6.2 Hz), 1.97-1.76, 1.44-1.26 (2×m, 5H). $^{13}$C NMR (CD$_3$OD) δ 157.3, 157.2, 150.1, 147.5, 142.8, 142.6, 135.1, 130.7, 123.5, 121.5, 120.5, 119.7, 91.3, 88.2, 86.9, 82.1, 75.5, 72.6, 63.5, 45.4, 36.7, 32.6, 26.5. LRMS ESI (M+H$^+$) 542.1. HPLC rt=9.7 min.

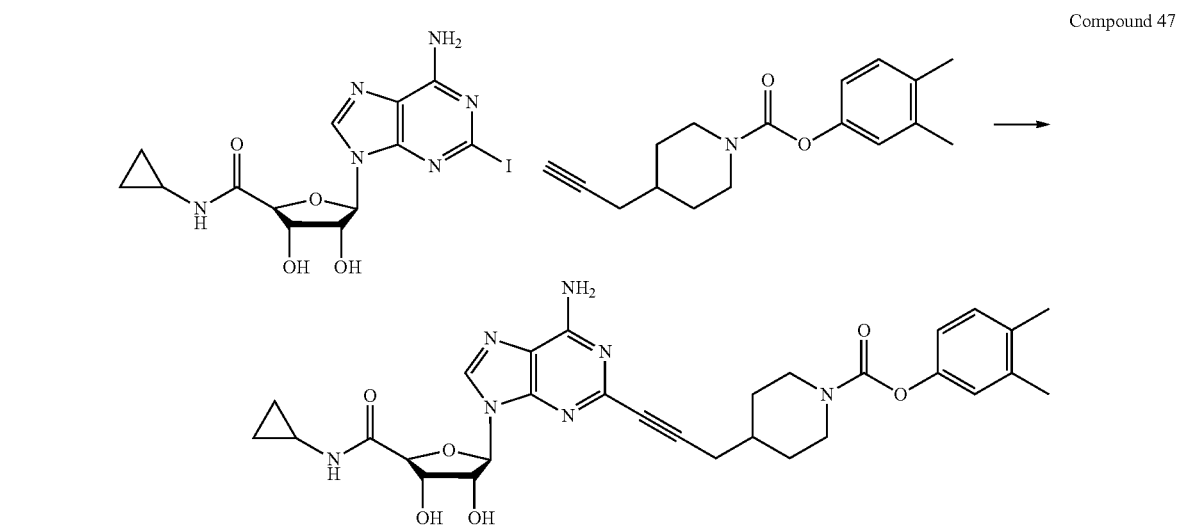

Compound 47

N-Cyclopropyl 2-{3-[1-(3,4-dimethylphenoxycarbonyl)-4-piperidinyl]-1-propyn-1-yl}adenosine-5'-uronamide. Dimethylphenyl 4-(2-propyn-1-yl)piperidine-1-carboxylate, xx (230 mg, 0.8325 mmol) was added to a solution of N-cyclopropyl-2-iodoadenosine-5'-uronamide (0.100 g, 0.231 mmol) according to general procedure 2. Yield=23.0 mg, 17%. m/z MH$^+$=590.25. HPLC rt=11.82 min.

Compound 48

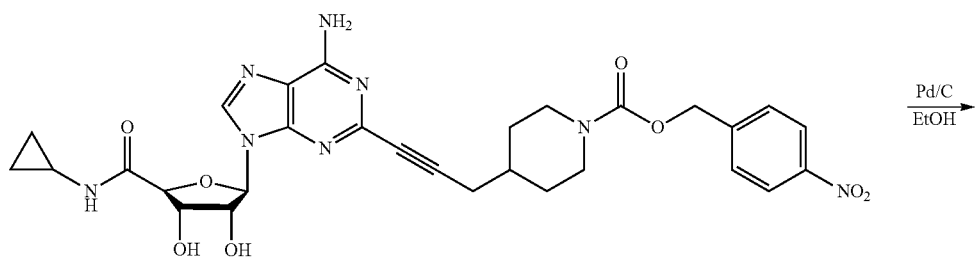

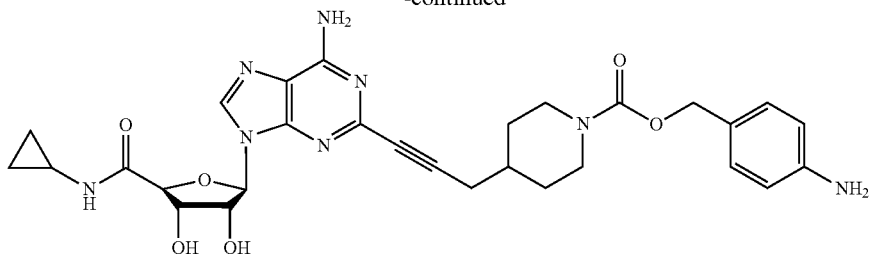

N-Cyclopropyl 2-{3-[1-((4-amino)benzyloxycarbanoyl)-4-piperidinyl]propyn-1-yl}adenosine-5'-uronamide. Batch: AP32-030. N-Cyclopropyl 2-{3-[1-(4-nitrobenzylcarbonoyl)-4-piperidinyl]-1-propyn-1-yl}adenosine-5'-uronamide, batch AP26-30 (0.0015 g, 0.0156 mmol) was added to a solution of Pd/C (catalytic) in EtOH (3 mL). The solution was left stirring for 12 hours under $H_2$ at room temperature and then concentrated and purified via Prep HPLC to afford a white solid. m/z MH$^+$=592.01, HPLC rt=11 min.

N-Ethyl 2-{3-[1-(3,4-dichlorophenoxycarbonyl)-4-piperidinyl]-1-propyn-1-yl}adenosine-5'-uronamide. Dichlorophenyl 4-(2-propyn-1-yl)piperidine-1-carboxylate, xx (0.287 mg, 0.918 mmol) was added to a solution of N-ethyl-2-iodoadenosine-5'-uronamide (0.110 g, 0.255 mmol) according to general procedure 2. Yield=15.0 mg, 10%. m/z MH$^+$=618.18. HPLC rt=12.39 min.

Compound 49

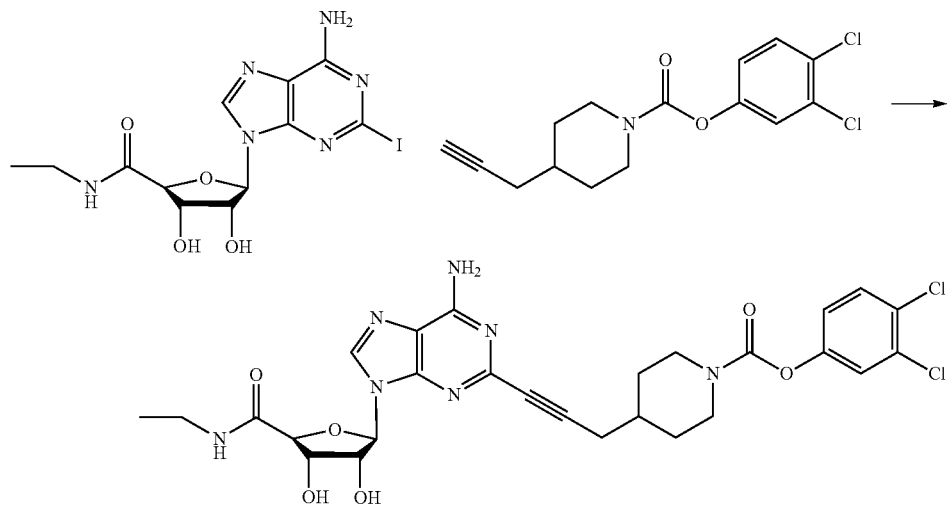

Compound 50

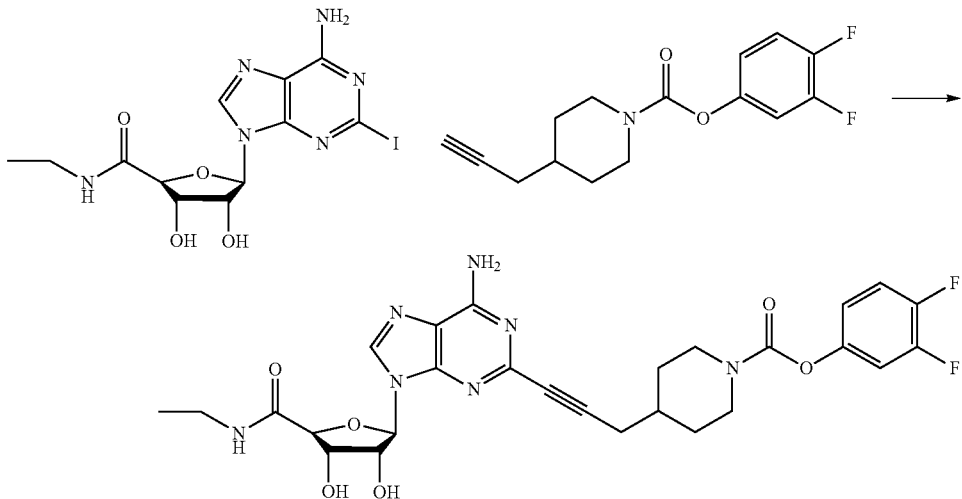

N-Ethyl 2-{3-[1-(3,4-difluorophenoxycarbonyl)-4-piperidinyl]-1-propyn-1-yl}adenosine-5'-uronamide. Difluorophenyl 4-(2-propyn-1-yl)piperidine-1-carboxylate, xx (0.257 mg, 0.918 mmol) was added to a solution of N-ethyl-2-iodoadenosine-5'-uronamide (0.110 g, 0.255 mmol) according to general procedure 2. Yield=23.0 mg, 16%. m/z MH+=586.28. HPLC rt=10.88 min.

N-Cyclopropyl 2-{3-[1-(3,4-fluorophenoxycarbonyl)-4-piperidinyl]-1-propyn-1-yl}adenosine-5'-uronamide. Difluorophenyl 4-(2-propyn-1-yl)piperidine-1-carboxylate, xx (0.233 mg, 0.8325 mmol) was added to a solution of N-cyclopropyl-2-iodoadenosine-5'-uronamide (0.100 g, 0.231 mmol) according to general procedure 2. Yield=32.0 mg, 24.0%. m/z MH+=598.20. HPLC rt=10.65 min.

Compound 51

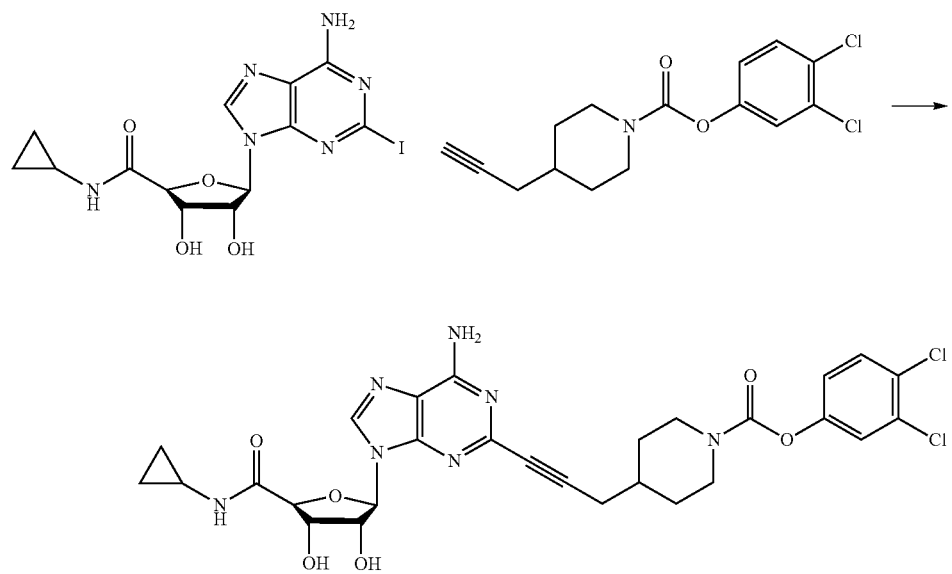

N-Cyclopropyl 2-{3-[1-(3,4-chlorophenoxycarbonyl)-4-piperidinyl]-1-propyn-1-yl}adenosine-5'-uronamide. Dichlorophenyl 4-(2-propyn-1-yl)piperidine-1-carboxylate, xx (0.260 mg, 0.8325 mmol) was added to a solution of N-cyclopropyl-2-iodoadenosine-5'-uronamide (0.100 g, 0.231 mmol) according to general procedure 2. Yield=38.0 mg, 26.4%. m/z MH+=630.19. HPLC rt=12.18 min.

Compound 52

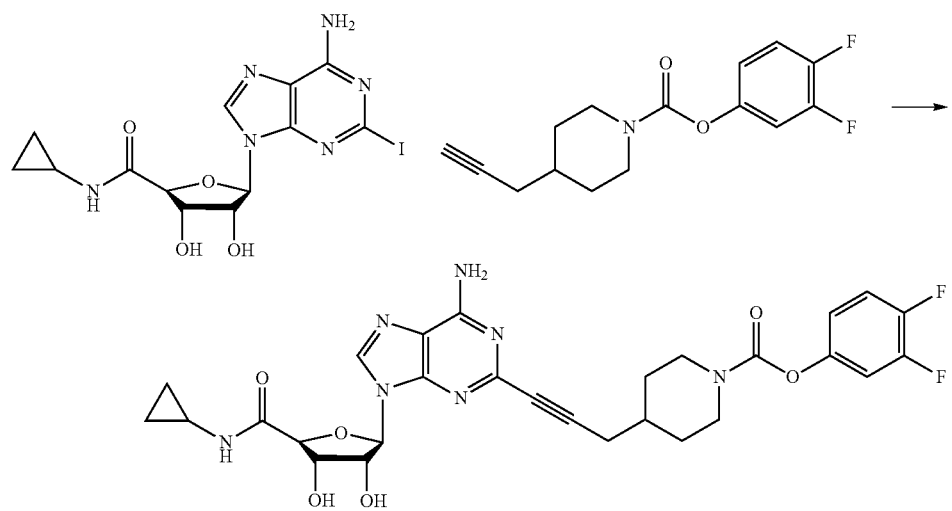

Compound 53

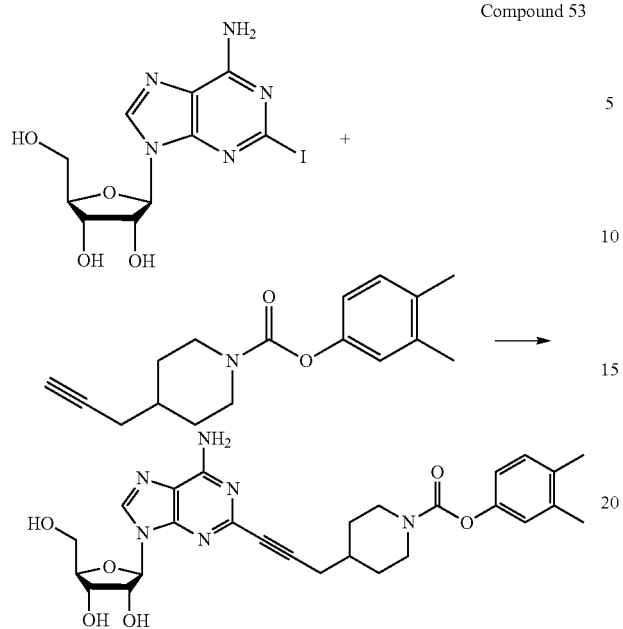

2-{3-[1-((3,4-Dimethyl)phenoxycarbanoyl)piperidin-4-yl]propyn-1-yl}adenosine. 3,4-Dimethylphenyl 4-(prop-2-ynyl)piperidine-1-carboxylate (1.430 g, 5.27 mmol) was added to a solution of 2-iodoadenosine (0.620 g, 1.577 mmol) according to general procedure 2: yield 252 mg, 30%. $^1$H NMR (CD$_3$OD) δ 8.30 (s, 1H), 7.08 (d 1H, J=8.2 Hz), 6.84 (d, 1H, J=2.3 Hz), 6.78 (dd, 1H, J=2.4, J=8.1 Hz), 5.93 (d, 1H, J=6.5 Hz), 4.71 (dd, 1H, J=5.1 Hz, J=6.5 Hz), 4.38-4.27 (m, 2H), 4.25-4.14 (m, 2H), 3.89 (dd, 1H, J=2.3 Hz, J=12.6 Hz), 3.74 (dd, 1H, J=2.6, J=12.6 Hz), 3.04, 2.90 (2×br t, 2H), 2.46 (d, 2H, J=6.2 Hz), 2.23, 2.22 (2×s, 6H), 2.02-1.79, 1.52-1.26 (2×m, 5H). $^{13}$C NMR (CD$_3$OD) δ 157.3, 155.8, 150.8, 150.2, 147.5, 142.6, 138.8, 134.7, 131.1, 123.7, 120.5, 119.9, 91.4, 88.3, 86.7, 82.3, 75.5, 72.6, 63.5, 45.5, 36.5, 32.5, 26.5, 19.8, 19.1. LRMS ESI (M+H$^+$) 537.2. HPLC rt=10.9 min.

Compound 54

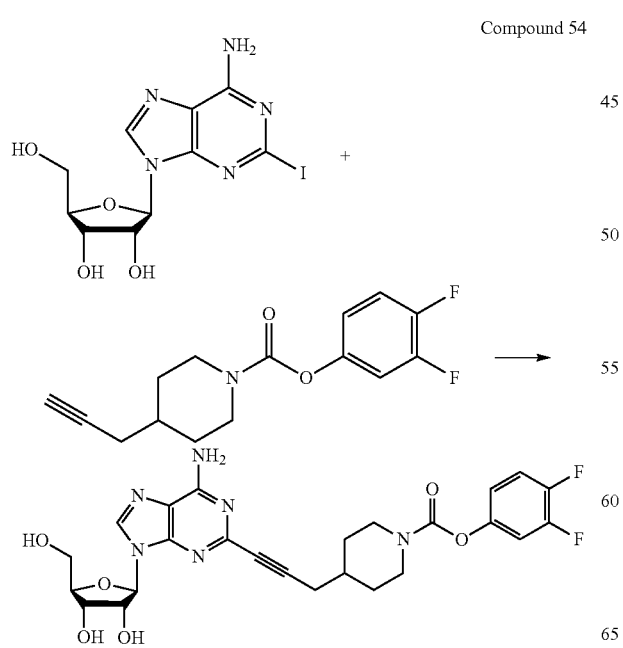

2-{3-[1-((3,4-Difluoro)phenoxycarbanoyl)piperidin-4-yl]propyn-1-yl}adenosine. 3,4-Difluorophenyl 4-(prop-2-ynyl)piperidine-1-carboxylate (1.830 g, 6.55 mmol) was added to a solution of 2-iodoadenosine (0.611 g, 1.554 mmol) according to general procedure 2: yield 201 mg, 24%. $^1$H NMR (CD$_3$OD) δ 8.30 (s, 1H), 7.25 (m, 1H), 7.12 (m, 1H), 6.96-6.89 (m, 1H), 5.93 (d, 1H, J=6.5 Hz), 4.71 (dd, 1H, J=5.1 Hz, J=6.4 Hz), 4.35-4.24 (m, 2H), 4.23-4.13 (m, 2H), 3.89 (dd, 1H, J=2.3 Hz, J=12.6 Hz), 3.74 (dd, 1H, J=2.5, J=12.6 Hz), 3.05, 2.91 (2×br t, 2H), 2.46 (d, 2H, J=6.2 Hz), 2.01-1.79, 1.52-1.27 (2×m, 5H). LRMS ESI (M+H$^+$) 545.2. HPLC rt=9.1 min.

Compound 55

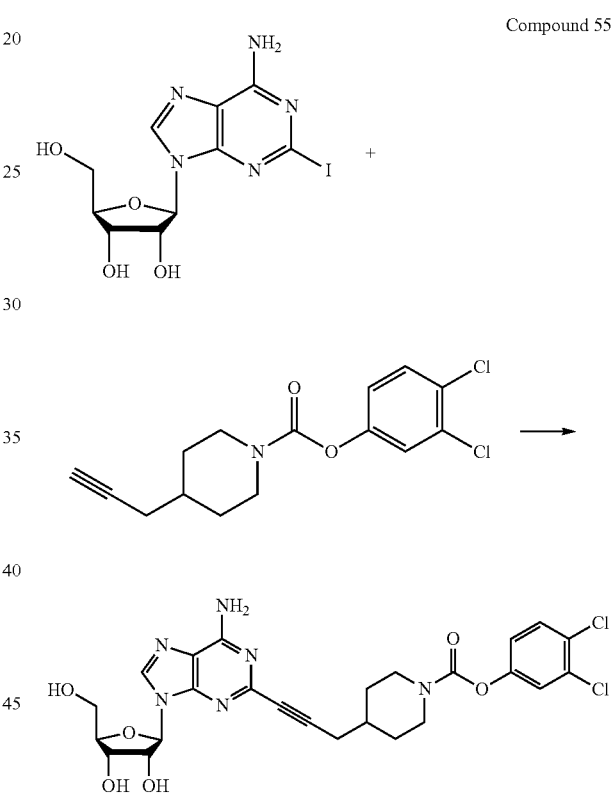

2-{3-[1-((3,4-Chloro)phenoxycarbanoyl)piperidin-4-yl]propyn-1-yl}adenosine. 3,4-Dichlorophenyl 4-(prop-2-ynyl)piperidine-1-carboxylate (1.730 g, 5.54 mmol) was added to a solution of 2-iodoadenosine (0.657 g, 1.671 mmol) according to general procedure 2: yield 427 mg, 44%. $^1$H NMR (CD$_3$OD) δ 8.30 (s, 1H), 7.50 (d 1H, J=8.8 Hz), 7.36 (d, 1H, J=2.6 Hz), 7.08 (dd, 1H, J=2.7, J=8.8 Hz), 5.93 (d, 1H, J=6.5 Hz), 4.71 (dd, 1H, J=5.1 Hz, J=6.3 Hz), 4.35-4.14 (m, 4H), 3.89 (dd, 1H, J=2.3 Hz, J=12.6 Hz), 3.74 (dd, 1H, J=2.5, J=12.6 Hz), 3.06, 2.92 (2×br t, 2H), 2.46 (d, 2H, J=6.3 Hz), 2.03-1.80, 1.54-1.28 (2×m, 5H). $^{13}$C NMR (CD$_3$OD) δ 157.3, 154.5, 152.0, 150.3, 147.6, 142.6, 133.5, 131.8, 130.0, 125.2, 123.0, 120.5, 91.4, 88.3, 86.7, 82.3, 75.5, 72.6, 63.5, 45.8, 36.4, 32.5, 26.4. LRMS ESI (M+H$^+$) 577.1. HPLC rt=7.6 min.

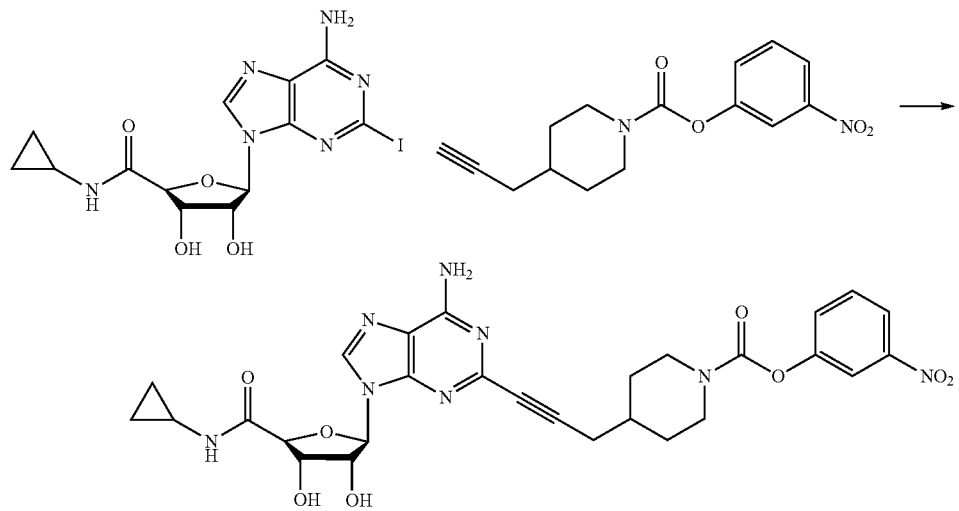

Compound 56

N-Cyclopropyl 2-{3-[1-(3-nitrophenoxycarbonyl)-4-piperidinyl]-1-propyn-1-yl}adenosine-5'-uronamide. Nitrophenyl 4-(2-propyn-1-yl)piperidine-1-carboxylate, xx (0.240 mg, 0.8325 mmol) was added to a solution of N-cyclopropyl-2-iodoadenosine-5'-uronamide (0.100 g, 0.231 mmol) according to general procedure 2. Yield=15.0 mg, 11.0%. m/z MH$^+$=607.26. HPLC rt=9.17 min.

were harvested 3 days post-infection and washed twice in insect PBS (PBS pH 6.3). Cells were then resuspended in lysis buffer (20 mM HEPES pH 7.5, 150 mM NaCl, 3 mM MgCl$_2$, 1 mM β-mercaptoethanol (BME), 5 μg/mL leupeptin, 5 μg/mL pepstatin A, 1 μg/mL aprotinin, and 0.1 mM PMSF) and snap frozen for storage at −80° C. Cells were thawed on ice, brought to 30 mL total volume in lysis buffer, and burst by

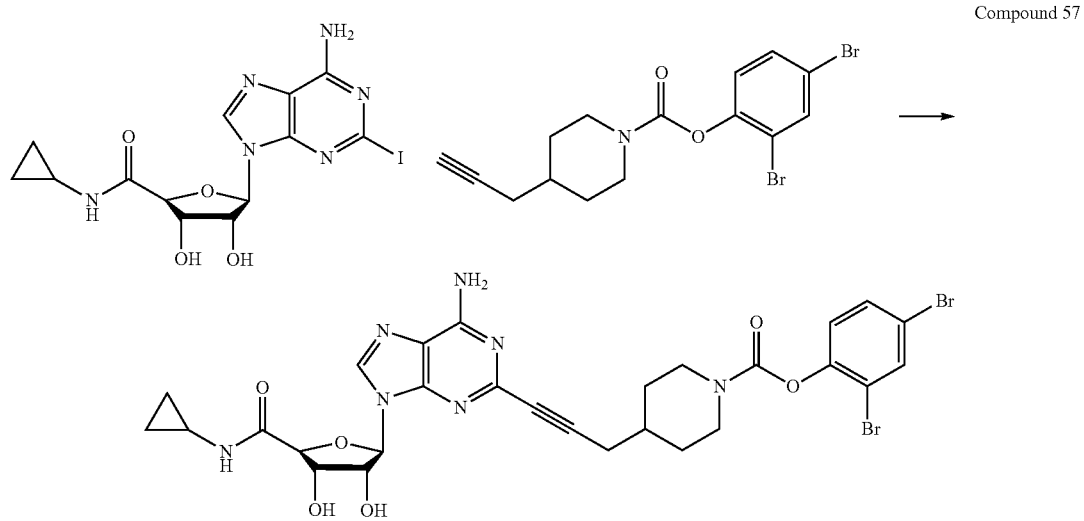

Compound 57

N-Cyclopropyl 2-{3-[1-(2,4-bromophenoxycarbonyl)-4-piperidinyl]-1-propyn-1-yl}adenosine-5'-uronamide. Dibromophenyl 4-(2-propyn-1-yl)piperidine-1-carboxylate, xx (0.333 mg, 0.8325 mmol) was added to a solution of N-cyclopropyl-2-iodoadenosine-5'-uronamide (0.100 g, 0.231 mmol) according to general procedure 2. Yield=2.0 mg, 1.3%. m/z MH$^+$=708.08. HPLC rt=11.04 min.

Cell culture and membrane preparation. Sf9 cells were cultured in Grace's medium supplemented with 10% fetal bovine serum, 2.5 μg/ml amphotericin B and 50 μg/ml gentamycin in an atmosphere of 50% N$_2$/50% O$_2$. Viral infection was performed at a density of 2.5×10$^6$ cells/mL with a multiplicity of infection of two for each virus used. Infected cells N$_2$ cavitation (600 psi for 20 minutes). A low-speed centrifugation was performed to remove any unlysed cells (1000×g for 10 minutes), followed by a high-speed centrifugation (17,000×g for 30 minutes). The pellet from the final centrifugation was homogenized in buffer containing 20 mM HEPES pH 8, 100 mM NaCl, 1% glycerol, 2 μg/mL leupeptin, 2 μg/mL pepstatin A, 2 μg/mL Aprotinin, 0.1 mM PMSF, and 10 μM GDP using a small glass homogenizer followed by passage through a 26 gauge needle. Membranes were aliquoted, snap frozen in liquid N$_2$, and stored at −80° C. Membranes from cells stably expressing the human A$_1$ AR(CHO K1 cells) or A$_3$ AR (HEK 293 cells) were prepared as described (Robeva et al., 1996).

Radioligand Binding Assays. Radioligand binding to recombinant human $A_{2A}$ receptors in Sf9 cell membranes was performed using either the radiolabeled agonist, $^{125}$I-APE (Luthin et al., 1995) or the radiolabeled antagonist, $^{125}$I-ZM241385 ($^{125}$I-ZM). To detect the high affinity, GTPγS-sensitive state of $A_1$ and $A_3$ AR, we used the agonist, $^{125}$I-ABA (Linden et al., 1985; Linden et al., 1993). Binding experiments were performed in triplicate with 5 μg ($A_{2A}$) or 25 μg ($A_1$ and $A_3$) membrane protein in a total volume of 0.1 mL HE buffer (20 mM HEPES and 1 mM EDTA) with 1 U/mL adenosine deaminase and 5 mM $MgCl_2$ with or without 50 μM GTPγS. Membranes were incubated with radioligands at room temperature for three hours (for agonists) or two hours (for antagonists) in Millipore Multiscreen® 96-well GF/C filter plates and assays were terminated by rapid filtration on a cell harvester (Brandel, Gaithersburg, Md.) followed by 4×150 washes over 30 seconds with ice cold 10 mM Tris-HCl, pH 7.4, 10 mM $MgCl_2$. Nonspecific binding was measured in the presence of 50 μM NECA. Competition binding assays were performed as described (Robeva et al., 1996) using 0.5-1 nM $^{125}$I-APE, $^{125}$I-ZM241385, or $^{125}$I-ABA. We found that it was sometimes important to change pipette tips following each serial dilution to prevent transfer on tips of potent hydrophobic compounds. The $K_i$ values for competing compound binding to a single site were derived from $IC_{50}$ values with correction for radioligand and competing compound depletion as described previously (Linden, 1982).

Linden J (1982) Calculating the Dissociation Constant of an Unlabeled Compound From the Concentration Required to Displace Radiolabel Binding by 50%. *J Cycl Nucl Res* 8: 163-172.

Linden J, Patel A and Sadek S (1985) [$^{125}$I]Aminobenzyladenosine, a New Radioligand With Improved Specific Binding to Adenosine Receptors in Heart. *Circ Res* 56: 279-284.

Linden J, Taylor H E, Robeva A S, Tucker A L, Stehle J H, Rivkees S A, Fink J S and Reppert S M (1993) Molecular Cloning and Functional Expression of a Sheep $A_3$ Adenosine Receptor With Widespread Tissue Distribution. *Mol Pharmacol* 44: 524-532.

Luthin D R, Olsson R A, Thompson R D, Sawmiller D R and Linden J (1995) Characterization of Two Affinity States of Adenosine $A_{2A}$ Receptors With a New Radioligand, 2-[2-(4-Amino-3-[$^{125}$I]Iodophenyl)Ethylamino]Adenosine. *Mol Pharmacol* 47: 307-313.

Robeva A S, Woodard R, Luthin D R, Taylor H E and Linden J (1996) Double Tagging Recombinant $A_1$- and $A_{2A}$-Adenosine Receptors With Hexahistidine and the FLAG Epitope. Development of an Efficient Generic Protein Purification Procedure. *Biochem Pharmacol* 51: 545-555.

Chemiluminescence Methods: Luminol enhanced chemiluminescence, a measure of neutrophil oxidative activity, is dependent upon both superoxide production and mobilization of the granule enzyme myeloperoxidase. The light is emitted from unstable high-energy oxygen species such as hypochlorous acid and singlet oxygen generated by activated neutrophils.

Purified human neutrophils (2×106/ml) suspended in Hanks balanced salt solution containing 0.1% human serum albumin (HA), adenosine deaminase (1 U/mL) and rolipram (100 nM) were incubated (37 C) in a water bath for 15 min with or without rhTNF (10 U/ml). Following incubation 100 L aliquots of the PMN were transferred to wells (White walled clear bottom 96 well tissue culture plates Costar #3670; 2 wells/condition) containing 501 HA and luminol (final concentration 100M) with or without adenosine agonist (final agonist concentrations 0.01-1000 nM). The plate was incubated 5 min (37 C) and then fMLP (50 1 in HA; final concentration 1M) was added to all wells.

Peak chemiluminescence was determined with a Victor 1420 Multilabel Counter in the chemiluminescence mode using the Wallac Workstation software. Data are presented as peak chemiluminescence as percent of activity in the absence of an adenosine agonist. The EC50 was determined using PRISM software. All compounds were tested with PMNs from three separate donors. This data is reported in Table 1.

Effect of $A_{2A}$ Agonists on Neutrophil Oxidative Activity f-met-leu-phe (fMLP), luminol, superoxide dismutase, cytochrome C, fibrinogen, adenosine deaminase, and trypan blue were obtained from Sigma Chemical. Ficoll-hypaque was purchased from ICN (Aurora, Ohio), and Cardinal Scientific (Santa Fe, N. Mex.) and Accurate Chemicals and Scientific (Westerbury, N.Y.). endotoxin (lipopolysaccharide; *E. coli* K235) was from List Biologicals (Campbell, Calif.). Hanks balanced salt solution (HBSS), and limulus amebocyte lysate assay kit were from BioWittaker (Walkersville, Md.). Human serum albumin (HSA) was from Cutter Biological (Elkhart, Ind.). Recombinant human tumor necrosis factor-α was supplied by Dianippon Pharmaceutical Co. Ltd. (Osaka, Japan). ZM241385 (4-(2-[7-amino-2-(2-furyl)-[1,2,4]triazolo[2,3-a] [1,3,5]triazin-5-yl amino]ethyl)phenol) was a gift from Simon Poucher, Zeneca Pharmaceuticals, Cheshire, UK. Stock solutions (1 mM and 10 mM in DMSO) were made and stored at −20° C.

Human neutrophil preparation Purified neutrophils (98% neutrophils and >95% viable by trypan blue exclusion) containing <1 platelet per 5 neutrophils and <50 pg/ml endotoxin (limulus amebocyte lysate assay) were obtained from normal heparinized (10 U/ml) venous blood by a one step Ficoll-hypaque separation procedure (A. Ferrante et al., *J. Immunol. Meth.*, 36, 109 (1980)).

Release of inflammatory reactive oxygen species from primed and stimulated human neutrophils Chemiluminescence Luminol-enhanced chemiluminescence, a measure of neutrophil oxidative activity, is dependent upon both superoxide production and mobilization of the lysosomal granule enzyme myeloperoxidase. The light is emitted from unstable high-energy oxygen species generated by activated neutrophils. Purified neutrophils (5-10×10$^5$/ml) were incubated in Hanks balanced salt solution containing 0.1% human serum albumin (1 ml) with the tested $A_{2A}$ agonist with or without rolipram and with or without tumor necrosis factor α (1 U/ml) for 30 minutes at 37° C. in a shaking water bath. Then luminol ($1×10^{-4}$ M) enhanced f-met-leu-phe (1 mcM) stimulated chemiluminescence was read with a Chronolog® Photometer (Crono-log Corp., Havertown, Pa.) at 37° C. for 2-4 minutes. Chemiluminescence is reported as relative peak light emitted (=height of the curve) compared to samples with tumor necrosis factor-α and without agonist or rolipram.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A method for treating biological diseases comprising the administration of an effective amount of a suitable antibiotic agent, antifungal agent, or antiviral agent in conjunction with a compound of formula I or a pharmaceutically acceptable salt thereof,

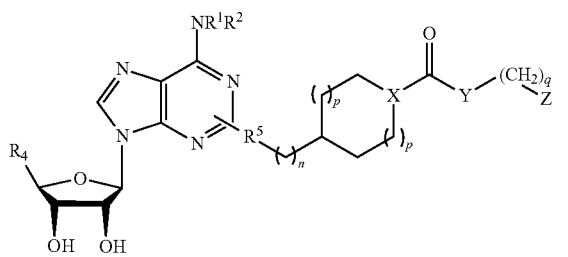

(I)

R¹ and R² independently are selected from the group consisting of H, (C₁-C₈)alky, (C₃-C₈)cycloalkyl, (C₃-C₈)cycloalkyl(C₁-C₈)alkylene, aryl, aryl(C₁-C₈)alkylene, heteroaryl, heteroaryl(C₁-C₈)alkylene-, diaryl(C₁-C₈) alkylene, and diheteroaryl(C₁-C₈)alkylene, wherein the aryl and heteroaryl rings are optionally substituted with 1-4 groups independently selected from fluoro, chloro, iodo, bromo, methyl, trifluoromethyl, and methoxy;

each R independently is selected from the group consisting of H, C₁-C₄ alkyl, cyclopropyl, cyclobutyl, and (CH₂)ₐ cyclopropyl;

X is CH or N, provided that when X is CH then Z cannot be substituted with halogen, C₁-C₆alkyl, hydroxyl, amino, or mono- or di-(C₁-C₆-alkyl)amino;

Y is selected from the group consisting of O, NR¹, —(OCH₂CH₂O)ₘCH₂—, and —(NR¹CH₂CH₂O)ₘCH₂—, provided that when Y is O or NR¹, then at least one substituent is present on Z;

Z is selected from the group consisting of 5-membered heteroaryl, 6-membered aryl, 6-membered heteroaryl, carbocyclic biaryl, and heterocyclic biaryl, wherein the point of attachment of Y to Z is a carbon atom on Z, wherein Z is substituted with 0-4 groups independently selected from the group consisting of F, Cl, Br, I, (C₁-C₄)alkyl, —(CH₂)ₐOR³, —(CH₂)ₐNR³R³, —NHOH, —NR³ NR³, nitro, —(CH₂)ₐCN, —(CH₂)ₐCO₂R³, —(CH₂)ₐCONR³R³, trifluoromethyl, and trifluoromethoxy;

alternatively, Y and Z together form an indolyl, indolinyl, isoindolinyl, tetrahydroisoquinolinyl, or tetrahydroquinolinyl moiety wherein the point of attachment is via the ring nitrogen and wherein said indolyl, indolinyl, isoindolinyl, tetrahydroisoquinolinyl, or tetrahydroquinolinyl moiety, which is substituted with 0-4 groups independently selected from the group consisting of F, Cl, Br, I, C₁-C₄alkyl, —(CH₂)ₐOR³, —(CH₂)ₐNR³R³, —NHOH, —NR³NR³R³, NO₂, —(CH₂)ₐCN, —(CH₂)ₐCO₂R³, —(CH₂)ₐCONR³R³, CF₃, and OCF₃;

R³ is independently selected from the group consisting of H, (C₁-C₆)alkyl, cycloalkyl, aryl, and heteroaryl;

R⁴ is selected from the group consisting of CH₂OR, C(O)NRR, and CO₂R;

a is selected from 0, 1, and 2;

m is selected from 1, 2, and 3;

n is selected from 0, 1, and 2;

each p independently is selected from 0, 1, and 2; and, q is selected from 0, 1, and 2.

2. The method of claim 1, wherein the compound is of formula (Ia) or a pharmaceutically acceptable salt thereof:

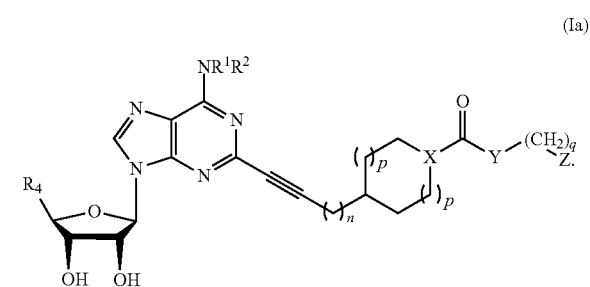

(Ia)

3. The method of claim 2, wherein the compound is of formula (Ib) or a pharmaceutically acceptable salt thereof:

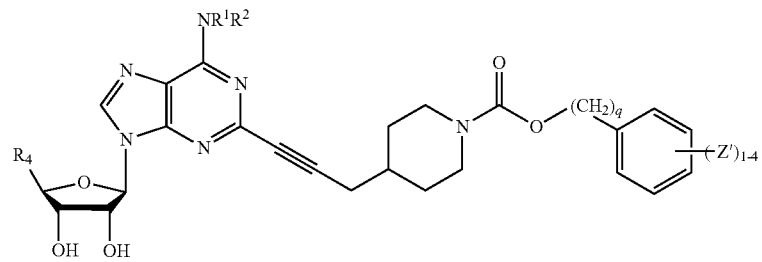

(Ib)

wherein:

each Z' is independently selected from the group consisting F, Cl, Br, I, C₁-C₄ alkyl, —(CH₂)ₐOR³, —(CH₂)ₐNR³R³, —NHOH, —NR³NR³R³, NO₂, —(CH₂)ₐCN, —(CH₂)ₐCO₂R³, —(CH₂)ₐCONR³R³, CF₃, and OCF₃.

4. The method of claim 3, wherein the compound is of formula (Ic) or a pharmaceutically acceptable salt thereof:

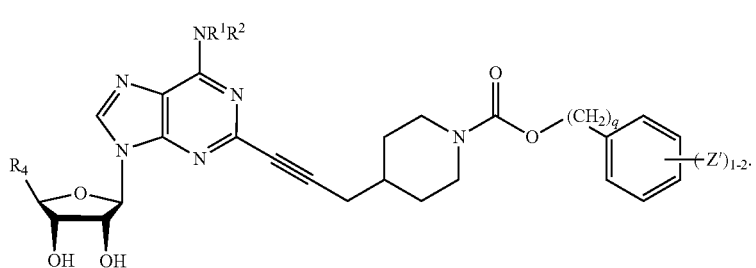

(Ic)

5. The method of claim 4, wherein Z' is selected from the group consisting of F, Cl, methyl, $OR^3$, $NO_2$, CN, $NR^3R^3$ and $CO_2R^3$.

6. The method of claim 5, wherein $R^3$ is methyl or hydrogen.

7. The method of claim 1, wherein the compound is selected from the group consisting of Compound Numbers 3, 5-31, and 33-57 shown in Table 1.

8. The method of claim 1, wherein the compound further includes a pharmaceutically acceptable carrier.

* * * * *